United States Patent [19]

Lochead et al.

[11] Patent Number: 5,447,943

[45] Date of Patent: * Sep. 5, 1995

[54] NOVEL BENZOPYRAN DERIVATIVES

[75] Inventors: Alistair W. Lochead, Charenton; Michel J. Navet, Bretigny-Sur-Orge; Peter E. Hicks, Saint-Remy-Les-Chevreuse, all of France

[73] Assignee: Syntex (U.S.A.) Inc., Palo Alto, Calif.

[*] Notice: The portion of the term of this patent subsequent to Oct. 5, 2010 has been disclaimed.

[21] Appl. No.: 96,583

[22] Filed: Jul. 22, 1993

Related U.S. Application Data

[63] Continuation-in-part of Ser. No. 751,491, Aug. 29, 1991, Pat. No. 5,250,547.

[51] Int. Cl.$^6$ .................. A61K 31/44; C07D 405/04
[52] U.S. Cl. ..................... 514/337; 546/269
[58] Field of Search .................. 546/269; 514/337

[56] References Cited

U.S. PATENT DOCUMENTS 5,021,432  6/1991  Yanamaka et al. ............... 514/337

FOREIGN PATENT DOCUMENTS 0375449  6/1990  European Pat. Off. .
WO89/10925  11/1989  WIPO .

OTHER PUBLICATIONS

Potassium Channel Modulators, by Robertson et al., J. Med. Chem., 33, 1529–1541 (1990).
Relaxant Activity of 4–Amidobenzopyrans, by Buckle et al., J. Med. Chem., 33, 3028–3034 (1990).
Structure–Activity Relationships of K+ Channel Openers, by Edwards et al., Trends in Pharmacological Sciences, 11, 417–422 (1990).

*Primary Examiner*—Jane Fan
*Attorney, Agent, or Firm*—Brian Lewis

[57] ABSTRACT

Compounds of the Formula:

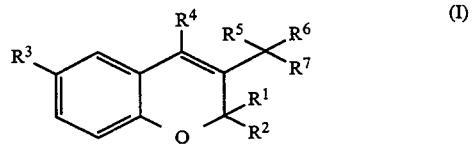

(I)

wherein:
$R^{1-7}$ are as defined in the specification. The compounds and salts exhibit useful pharmacological properties, including potassium channel activating properties and 5-lipoxygenase inhibiting properties, and in particular are useful as smooth muscle relaxants and bronchodilators.

16 Claims, No Drawings

NOVEL BENZOPYRAN DERIVATIVES

FIELD OF THE INVENTION

This is a Continuation-in-Part of U.S. patent application Ser. No. 07/751,491, filed Aug. 29, 1991, now U.S. Pat. No. 5,250,547, issued Oct. 5, 1993, the complete disclosure of which is hereby incorporated by reference.

This invention relates to benzopyran derivatives, and pharmaceutically acceptable salts thereof, which exhibit useful pharmacological properties, including potassium channel activating properties and 5-lipoxygenase inhibiting properties. Potassium channel activators have many useful properties, including the ability to relax smooth muscle and to act as bronchodilators. They are thus useful in treating a variety of disorders, including cardiovascular disorders, respiratory tract disorders, cerebrovasospasm, stroke, peripheral vascular occlusive disease, and gastro-intestinal disorders, uterine disorders and renal disorders alleviated by treatment with smooth muscle relaxants. Inhibitors of 5-lipoxygenase have many useful properties, including the treatment of pain, inflammatory and allergic conditions, the treatment of hyperproliferative diseases, ulcerative colitis and stroke.

The compounds of this invention are also useful in treating glaucoma, epilepsy, psycho-depressive conditions and baldness.

RELATED DISCLOSURES

The compounds of this invention are various benzopyran derivatives, useful for example as potassium channel activators and 5-lipoxygenase inhibitors. Compounds somewhat structurally related are described in European Patent Application Nos. 277,611, EP 277,612, EP 312,432, EP 339,562, EP 346,724, EP 375,449 and EP 410,208, *J. Med. Chem.*, Vol. 33, 1529–41 and 3028–34 (1990), and *Trends in Pharm. Science*, Vol. 11, 417–22 (1990).

SUMMARY OF THE INVENTION

One aspect of the invention concerns novel compounds represented by the formula:

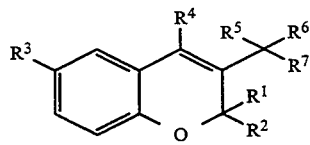

wherein:
  $R^1$ and $R^2$ are independently hydrogen or lower alkyl, or when taken together with the carbon to which they are attached are cycloalkyl of 3 to 8 carbon atoms;
  $R^3$ is hydrogen; halo; fluoro lower alkyl; cyano; or nitro;
  $R^4$ is

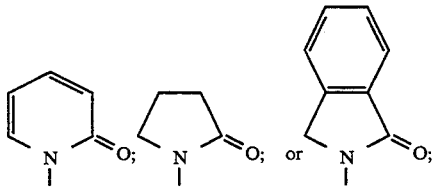

$R^5$ and $R^6$ are independently hydrogen or lower alkyl; and
$R^7$ is $-NR^8R^9$, wherein:
  $R^8$ is hydrogen; lower alkyl; lower alkoxy; hydroxy; or hydroxy lower alkyl; and
  $R^9$ is hydrogen; lower alkyl; hydroxy lower alkyl; $-SO_2R^{10}$; $-CO_2R^{10}$; $-C(O)NR^{11}R^{12}$; $-C(S)NR^{11}R^{12}$; or $-C(O)R^{12}$;
  wherein:
    $R^{10}$ is lower alkyl;
    $R^{11}$ is hydrogen or lower alkyl; and
    $R^{12}$ is hydrogen, lower alkyl, or fluoro lower alkyl;

with the proviso that $R^8$ and $R^9$ cannot both be hydrogen; and the pharmaceutically acceptable salts thereof, are useful in treating a mammal having a disease state which is alleviated by treatment with e.g. a potassium channel activator or a 5-lipoxygenase inhibitor.

In another aspect, the invention relates to pharmaceutical compositions containing a therapeutically effective amount of a compound of Formula (I), or a pharmaceutically acceptable salt thereof, in admixture with one or more pharmaceutically acceptable, non-toxic carriers.

In yet another aspect, the invention relates to a method for treating a mammal having a disease state which is alleviable by treatment with a compound of Formula (I), for example as a potassium channel activator or a 5-lipoxygenase inhibitor, especially where the disease state is hypertension or asthma, by administering to a mammal in need thereof a therapeutically effective amount of a compound of Formula (I), or a pharmaceutically acceptable salt thereof.

DETAILED DESCRIPTION OF THE INVENTION

Definitions

As used herein:

"Alkyl" means a branched or unbranched saturated hydrocarbon chain containing 1 to 8 carbon atoms, such as methyl, ethyl, propyl, tert-butyl, n-hexyl, n-octyl and the like.

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated.

"Lower alkoxy" means the group —O—(lower alkyl) wherein lower alkyl is as herein defined.

"Cycloalkyl" means a saturated monovalent monocyclic hydrocarbon radical containing 3–8 carbon atoms, such as cyclopropyl, cyclobutyl, cyclopentyl, cyclohexyl, cycloheptyl and cyclooctyl.

"Halo" means fluoro, chloro, bromo or iodo.

"Hydroxy lower alkyl" means a lower alkyl radical as defined above that is substituted by a hydroxy group, for example hydroxymethyl, 2-hydroxyethyl, 6-hydroxyhexyl, and the like.

"Fluoro lower alkyl" means a lower alkyl radical as defined above that is substituted by one or more fluorine atoms, e.g. fluoromethyl, difluoromethyl, trifluoromethyl, 2-fluoroethyl, pentafluoroethyl, 6-fluorohexyl, and the like.

"Phenyl" encompasses all possible isomeric phenyl radicals optionally monosubstituted or disubstituted with a substituent selected from the group consisting of lower alkyl, lower alkoxy, hydroxy, trifluoromethyl and halo.

"Phenyl lower alkyl" denotes phenyl as defined above attached to a lower alkyl group as defined above, for example benzyl, 1-phenylethyl, and the like.

"Strong base" as used herein denotes a base such as sodium ethoxide, sodium methoxide, potassium t-butoxide, potassium phenylate, sodium hydride, and the like.

The terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

R$^4$ is defined as:

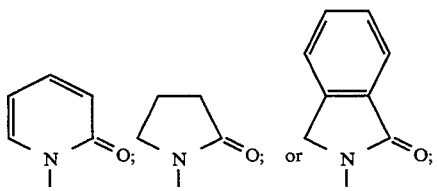

i.e. R$^4$H represents 2-oxo-1,2-dihydropyridine, 2-oxopyrrolidine, or 1-oxoisoindoline. Those skilled in the art will understand that various substitutions may be made on the pyridine, pyrrolidine and isoindoline ring systems, for example substitution of hydrogen by lower alkyl, lower alkoxy, halo, and the like, without departing from the true spirit and scope of the invention.

"Pharmaceutically acceptable salt" means those salts which retain the biological effectiveness and properties of the compounds of Formula (I), and which are not biologically or otherwise undesirable. Acid addition salts may be formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. In addition, the compounds of Formula (I) where R$^8$ is hydroxy and R$^9$ is —C(O)R$^{12}$ are capable of forming base addition salts. Such salts may be prepared from either inorganic or organic bases. Salts derived from inorganic bases include, but are not limited to, the sodium, potassium, lithium, ammonium, calcium, magnesium, ferrous, zinc, copper, manganous, aluminum, ferric, and manganic salts, and the like. Preferred inorganic salts are the ammonium, sodium, potassium, calcium, and magnesium salts. Salts derived from organic bases include, but are not limited to, salts of primary, secondary and tertiary amines, substituted amines including naturally-occuring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procains, hydrabamine, choline, betains, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline The compounds of this invention where R$^5$, R$^6$ and R$^7$ are different possess an asymmetric center, and can be produced as a racemic mixture or as individual stereoisomers. The individual stereoisomers may be obtained by resolving a racemic or non-racemic mixture of an intermediate at some appropriate stage of the synthesis, or by resolution of the compound of Formula (I). It is understood that the individual stereoisomers as well as racemic and non-racemic mixtures of stereoisomers are encompassed within the scope of the present invention.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl; "optionally followed by converting the free base to the acid addition salt" means that said conversion may or may not be carried out in order for the process described to fall within the invention, and the invention includes those processes wherein the free base is converted to the acid addition salt and those processes in which it is not.

The term "mammal" includes humans and all domestic and wild mammals, including, without limitation, cattle, horses, swine, sheep, goats, dogs, cats, rabbits, and the like.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e. arresting its development; or (iii) relieving the disease, i.e. causing regression of the disease.

The term "disease state alleviable by treatment with a potassium channel activator" as used herein is intended to cover all disease states which are generally acknowledged in the art to be usefully treated with potassium channel activators in general, and those disease states which have been found to be usefully treated by the specific potassium channel activators of our invention, the compounds of Formula (I). Such disease states include, but are not limited to, essential and pulmonary hypertension, congestive heart failure, angina, peripheral vascular occlusive disease, smooth muscle spasm, in particular, cerebro-vasospasm, cardiac arrhythmia, stroke, disorders of the respiratory tract, for example reversible airways obstruction and asthma. These derivatives are also useful in treating disorders associated with smooth muscle contractions of the gastro-intestinal tract, uterus or the urinary tract, including the ureter, and are also useful in the treatment of glaucoma, epilepsy, psycho-depressive conditions and baldness.

The term "disease state alleviable by treatment with a 5-lipoxygenase inhibitor" as used herein is intended to cover all disease states which are generally acknowledged in the art to be usefully treated with 5-lipoxygenase inhibitors. Such disease states include, but are not limited to, the treatment of pain, inflammatory and allergic conditions, the treatment of hyperproliferative diseases, ulcerative colitis and stroke.

The term "therapeutically effective amount" means that amount of a compound of Formula (I) which, when administered to a mammal in need thereof, is sufficient to effect treatment, as defined above, for those disease states treatable by a compound of Formula (I), examples of which are listed above. What amount constitutes a "therapeutically effective amount" will vary depending on the compound, the disease state and its severity, and the mammal to be treated, but may be determined routinely by one of ordinary skill in the art having regard to his own knowledge and to this disclosure.

The numbering system used in naming the intermediates and product compounds of the present invention is illustrated below, using a compound of Formula (I) as an example.

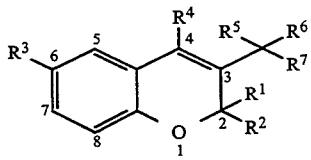

Following are examples of how representative compounds of Formula (I) are named:

The compound of Formula (I) wherein $R^1$ and $R^2$ are both methyl, $R^3$ is nitro, $R^4$ is 2-oxo-1,2-dihydropyridin-1-yl, $R^5$ and $R^6$ are both hydrogen, $R^8$ is hydroxy and $R^9$ is methyl is named:
6-nitro-2,2-dimethyl-3-(N-methyl-N-hydroxyamino)-methyl-4-(2-oxo-1,2-dihydropyridin-1-yl)-2H-1-benzopyran.

The compound of Formula (I) wherein $R^1$ and $R^2$ are both methyl, $R^3$ is trifluoromethyl, $R^4$ is 1-oxoisoindolin-2-yl, $R^5$ and $R^6$ are both hydrogen, $R^8$ is hydrogen and $R^9$ is —C(O)$R^{12}$, in which $R^{12}$ is methyl, is named:
6-trifluoromethyl-2,2-dimethyl-3-(acetamido)methyl-4-(1-oxoisoindolin-2-yl)-2H-1-benzopyran.

The compound of Formula (I) wherein $R^1$ and $R^2$ are both methyl, $R^3$ is pentafluoroethyl, $R^4$ is 2-oxo-1,2-dihydropyridin-1-yl, $R^5$ and $R^6$ are both hydrogen, $R^8$ is hydroxy and $R^9$ is —C(O)$R^{12}$, in which $R^{12}$ is methyl, is named:
6-pentafluoroethyl-2,2-dimethyl-3-(N-hydroxyacetamido)methyl-4-(2-oxo-1,2-dihydropyridin-1-yl)-2H-1-benzopyran.

Preferred Embodiments

Among the family of compounds of the present invention, one preferred category includes the compounds where $R^1$ and $R^2$ are both methyl and $R^6$ and $R^8$ are both hydrogen. Within this category a preferred group includes the compounds where $R^4$ is 2-oxo-1,2-dihydropyridin-1-yl. A preferred subgroup within this group includes compounds in which $R^3$ is hydrogen or halo, especially where $R^3$ is bromo or chloro. One preferred class within this subgroup includes compounds where $R^8$ is hydrogen and $R^9$ is —C(O)$R^{12}$. A second preferred class within this subgroup includes compounds where $R^8$ is hydroxy and $R^9$ is hydrogen, lower alkyl or —C(O)$R^{12}$, more especially where $R^{12}$ is hydrogen, methyl or trifluoromethyl. A third preferred class within this subgroup includes those compounds in which $R^8$ is lower alkoxy and $R^9$ is hydrogen.

A second preferred group includes the compounds where $R^4$ is 2-oxopyrrolidin-1-yl. One preferred subgroup within this group includes compounds where $R^8$ is hydrogen or hydroxy and $R^9$ is hydrogen, lower alkyl or —C(O)$R^{12}$.

A third preferred group includes the compounds where $R^4$ is 1-oxoisoindolin-2-yl. One preferred subgroup within this group includes compounds in which $R^8$ is hydrogen or hydroxy and $R^9$ is hydrogen, lower alkyl or —C(O)$R^{12}$.

A fourth preferred group includes the compounds where $R^4$ is 2-oxo-1,2-dihydropyridin-1-yl and $R^3$ is hydrogen or halo, especially where $R^1$ and $R^2$ are both methyl and $R^5$ and $R^6$ are both hydrogen. One preferred subgroup within this group includes compounds in which $R^8$ is hydroxy, and $R^9$ is hydrogen, lower alkyl or —C(O)$R^{12}$.

At present, the preferred compounds are:
6-nitro-2,2-dimethyl-3-(methoxyamino)methyl-4-(2-oxo-1,2-dihydropyridin-1-yl)-2H-1-benzopyran;
6-nitro-2,2-dimethyl-3-(formamido)methyl-4-(2-oxo-1,2-dihydropyridin-1-yl)-2H-1-benzopyran;
6-nitro-2,2-dimethyl-3-(acetamido)methyl-4-(2-oxo-1,2-dihydropyridin-1-yl)-2H-1-benzopyran;
6-nitro-2,2-dimethyl-3-(trifluoroacetamido)methyl-4-(2-oxo-1,2-dihydropyridin-1-yl)-2H-1-benzopyran;
6-nitro-2,2-dimethyl-3-(hydroxyamino)methyl-4-(2-oxo-1,2-dihydropyridin-1-yl)-2H-1-benzopyran;
6-nitro-2,2-dimethyl-3-(N-hydroxyacetamido)methyl-4-(2-oxo-1,2-dihydropyridin-1-yl)-2H-1-benzopyran;
6-cyano-2,2-dimethyl-3-(N-hydroxyacetamido)methyl-4-(2-oxo-1,2-dihydropyridin-1-yl)-2H-1-benzopyran;
6-trifluoromethyl-2,2-dimethyl-3-(formamido)methyl-4-(2-oxo-1,2-dihydropyridin-1-yl)-2H-1-benzopyran;
6-trifluoromethyl-2,2-dimethyl-3-(acetamido)methyl-4-(2-oxo-1,2-dihydropyridin-1-yl)-2H-1-benzopyran;
6-trifluoromethyl-2,2-dimethyl-3-(trifluoroacetamido)-methyl-4-(2-oxo-1,2-dihydropyridin-1-yl)-2H-1-benzopyran;
6-trifluoromethyl-2,2-dimethyl-3-(N-hydroxyacetamido)methyl-4-(2-oxo-1,2-dihydropyridin-1-yl)-2H-1-benzopyran; 6-pentafluoroethyl-2,2-dimethyl-3-(N-hydroxy-acetamido)methyl-4-(2-oxo-1,2-dihydropyridin-1-yl)-2H-1-benzopyran;
6-bromo-2,2-dimethyl-3-(N-hydroxy-acetamido)methyl-4-(2-oxo-1,2-dihydropyridin-1-yl)-2H-1-benzopyran;
6-chloro-2,2-dimethyl-3-(N-hydroxy-acetamido)methyl-4-(2-oxo-1,2-dihydropyridin-1-yl)-2H-1-benzopyran; and
6-bromo-2,2-dimethyl-3-(N-hydroxy-propionamido)-methyl-4-(2-oxo-1,2-dihydropyridin-1-yl)-2H-1-benzopyran.

METHODS OF PREPARATION

Preparation of Compounds of Formulae (14) and (15)

The compounds of Formula (I) are prepared from the intermediates of Formula (14) and (15), the preparation of which is illustrated in Reaction Schemes I and II.

Reaction Scheme I depicts the means by which various R₃ groups are introduced into the benzopyran nucleus.

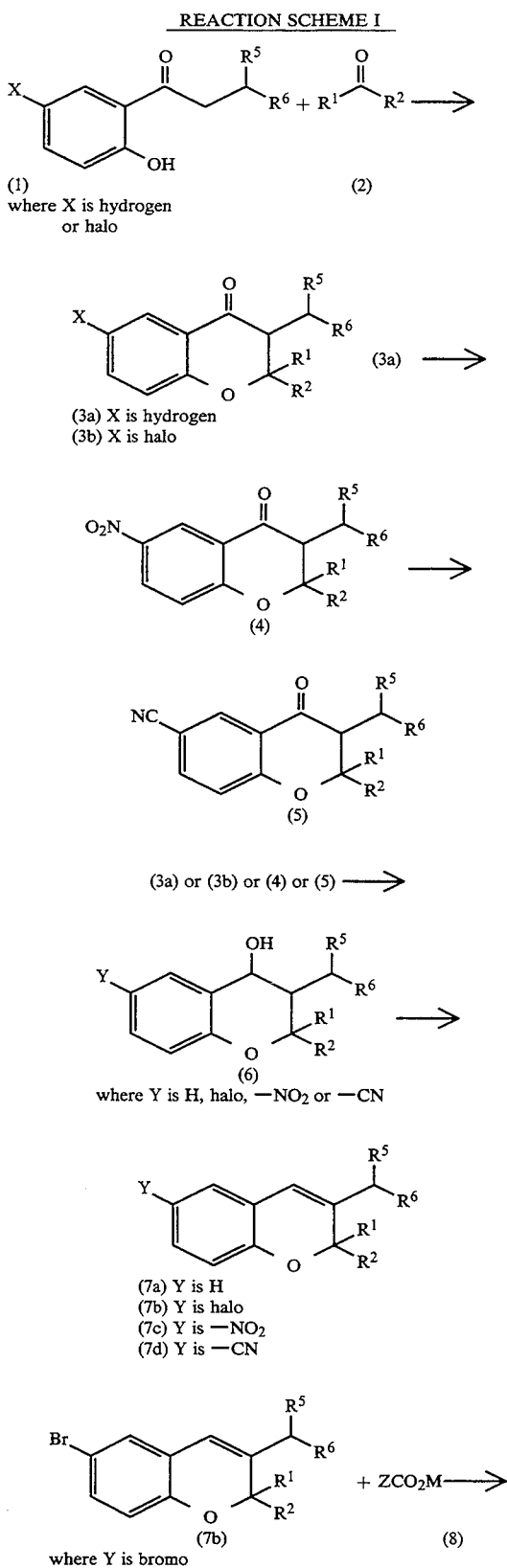

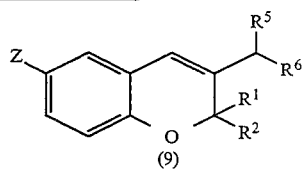

where Z is fluoro lower alkyl and M is sodium or potassium

Preparation of Compounds of Formula (3)

The compounds of Formula (1) are commercially available, from Aldrich Chemical Company inter alia, or may be prepared by the methods described in the chemical literature, for example by the method of Zalkow and Ghosal in *J. Org. Chem.*, Vol. 34, pp 1646–1650 (1969), or the method of Martin and Betoux, *Bull. Soc. Chim. France*, (46) pp 2079–2088 (1969). The compounds of Formula (2) are commercially available.

To prepare the compounds of Formula (3a), where X is hydrogen, and (3b), where X is halo, an appropriate compound of Formula (1) is reacted with about 1–3 molar equivalents, preferably about 1.5 molar equivalents, of a compound of Formula (2) in the presence of about 0.2 to 1 molar equivalents, preferably about 0.5 molar equivalents, of a secondary organic base (such as piperidine, morpholine, pyrrolidine and the like, preferably pyrrolidine).

The reaction is preferably carried out in an aromatic solvent (for example benzene, toluene, xylene, and the like, preferably toluene) at a temperature of about 60° C. to 100° C., preferably at about 85° C., for about 1–6 days, preferably about 3 days. When the reaction is substantially complete the 3,4-dihydro-1-benzopyran-4-one derivative, a compound of Formula (3), is isolated and purified by conventional means, preferably chromatography.

Preparation of Compounds of Formula (4)

The compounds of Formula (4) are prepared from the compounds of Formula (3a), where X is hydrogen. Typically an appropriate compound of Formula (3a) is dissolved in concentrated sulfuric acid at about 0° C., and an excess of a mixture of concentrated sulfuric acid and nitric acid (in about a 1:6 ratio) added, keeping the temperature at about 0°–5° C. The reaction is preferably carried out at a temperature of about 5° C., for about 1–8 hours, preferably about 3 hours. When the reaction is substantially complete the 6-nitro-3,4-dihydro-1-benzopyran-4-one derivative, a compound of Formula (4), is isolated and purified by conventional means, preferably filtration.

Preparation of Compounds of Formula (5)

The cyano compounds of Formula (5) are prepared from the nitro compounds of Formula (4) by standard literature procedures, i.e. the nitro group of the compound of Formula (4) is first reduced to the corresponding amine, which is then converted to a diazo derivative by reaction with a nitrite, followed by displacement of the diazo compound with cyanide to give the compound of Formula (5).

Typically, a compound of Formula (4) is hydrogenated with a suitable heterogeneous catalyst, for example rhodium on alumina, platinum oxide or preferably palladium on carbon, to the corresponding amine. For example, for every gram of a compound of Formula (4) dissolved in an inert solvent, preferably methanol, is added from 0.02 to 0.3 g, preferably about 0.1 g, of 10% palladium on carbon catalyst, and the mixture hydrogenated at a pressure of about 1–5 atmospheres, preferably about 1 atmosphere. The reaction is conducted at a temperature of about 20° to 60° C., preferably about 40°–50° C., until uptake of hydrogen ceases, usually about 4–6 hours.

When the reaction is substantially complete, the amine product is separated conventionally, dissolved in a water-miscible inert solvent, preferably ethanol, and added to an excess of an aqueous acidic solution, for example aqueous sulfuric acid or preferably aqueous hydrochloric acid (about 1M), and reacted with about 1–2 molar equivalents, preferably about 1.1 molar equivalents, of an alkali metal nitrite, preferably sodium nitrite. The reaction is carried out at a temperature of about −5° C. to 0° C., preferably at about 0° C., for about 15 minutes.

The diazo derivative thus produced is reacted with cyanide anions in aqueous solution. This aqueous solution preferably contains about 5–20 molar equivalents, preferably about 9 molar equivalents, of potassium cyanide together with a similar number of molar equivalents of cuprous cyanide. The reaction is carried out at a temperature of about 50° C. to 100° C., preferably at about 90° C., for about 1 hour. When the reaction is substantially complete, the 6-cyano-3,4-dihydro-1-benzopyran-4-one derivative, a compound of Formula (5), is isolated and purified by conventional means, preferably chromatography.

Preparation of Compounds of Formula (6)

The compounds of Formulae (3a), (3b), (4) or (5) are then reduced to the compounds of Formulae (6), where Y is hydrogen, halo, nitro or cyano, with a suitable reducing agent (for example lithium borohydride, lithium tri-t-butoxyaluminum hydride, sodium borohydride and the like, preferably sodium borohydride). In general, a solution or a suspension of a compound of Formulas (3a), (3b), (4) or (5) in a protic solvent, preferably methanol, is reacted with about 1 molar equivalent of sodium borohydride. The reaction is carried out at a temperature of about 15° C. to 30° C., preferably at about 25° C., for about 30 minutes to 6 hours, preferably about 2 hours. When the reaction is substantially complete, the 6-unsubstituted, 6-halo, 6-nitro or 6-cyano-4-hydroxy-3,4-dihydro-1-benzopyran derivative, a compound of Formula (6) where Y is hydrogen, halo, nitro or cyano, is separated and purified by conventional means.

Preparation of Compounds of Formulas (7a), (7b), (7c) and (7d)

A compound of Formula (6), where Y is hydrogen, halo, nitro or cyano, is then dehydrated by treatment with about 0.05–0.5 molar equivalents, preferably about 0.1 molar equivalents, of an acid catalyst, for example naphthalenesulfonic acid, preferably p-toluenesulfonic acid. The reaction is carried out by refluxing in a suitable solvent, for example benzene or preferably toluene, removing the water thus produced, for about 6–32 hours, preferably about 18 hours. When the reaction is substantially complete, the 6-unsubstituted, 6-halo, 6-nitro or 6-cyano-1-benzopyran derivative, a compound of Formula (7) where Y is hydrogen (7a), halo (7b), nitro (7c), or cyano (7d), is separated and purified by conventional means.

Preparation of Compounds of Formula (9)

Compounds of Formula (8) are commercially available, from Interchim for example, or are prepared according to the method described by Laganis and Chenard, *Tetrahedron Letters* 25(51), pp. 5831–5834 (1984).

The compounds of Formula (9) are those compounds where Z is fluoro lower alkyl; they are prepared from a compound of Formula (7b), i.e. where Y is halo, preferably bromo or iodo, most preferably iodo. An appropriate compound of Formula (7b) is reacted with about 1.5–5 molar equivalents, preferably about 3 molar equivalents, of a compound of Formula (8) in which M is sodium or preferably potassium and Z is fluoro lower alkyl. The reaction is carried out in the presence of about 1–4 molar equivalents, preferably about 2 molar equivalents, of a cuprous halide, preferably cuprous iodide, in an inert solvent mixture, comprising a polar solvent, preferably dimethylformamide, and an aromatic solvent, preferably toluene. The reaction is conducted at a temperature sufficient to distil off the aromatic solvent, and continued until the reaction temperature reaches about 130° C. to 170° C., preferably about 140° C., followed by heating at this temperature for about a further 2–10 hours, preferably about 4 hours. When the reaction is substantially complete, the 6-fluoro lower alkyl-1-benzopyran derivative, a compound of Formula (9), is separated and purified by conventional means, preferably chromatography.

Alternative Preparation of Compounds of Formulae (7)

Alternatively, the intermediate compounds of Formula (7) may be prepared according to Reaction Scheme IA.

REACTION SCHEME IA

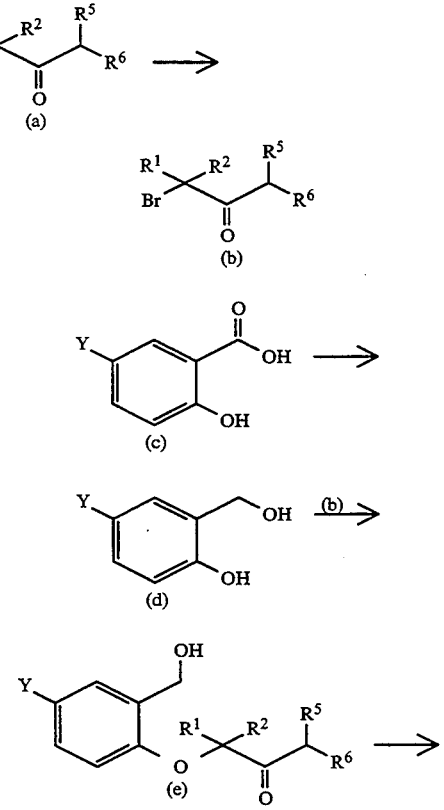

-continued
REACTION SCHEME IA

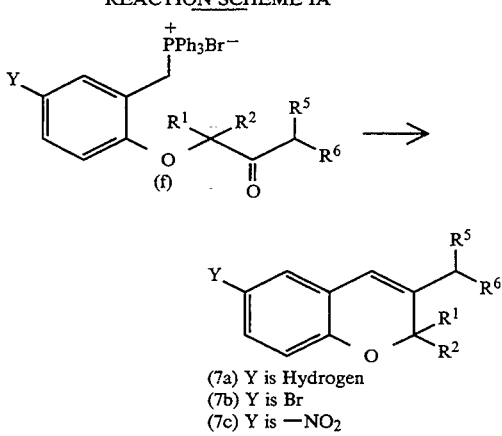

(7a) Y is Hydrogen
(7b) Y is Br
(7c) Y is —NO₂

Preparation of Compounds of Formula (b)

The compounds of Formula (a) are commercially available from Aldrich Chemical Company. The compounds of Formula (b) are prepared from a compound of Formula (a) by converting the alcohol to the corresponding brominated compound by conventional means, for example, reacting the alcohol with a brominating agent, such as phosphorous tribromide. Such a reaction may be carried out with or without an inert solvent, such as dichloromethane, toluene, at a temperature ranging from −10° C. to 20° C., preferably at 5° C. When the reaction is substantially complete, the α-bromopropanone derivative, a compound of Formula (b), is isolated and purified by conventional means.

Preparation of Compounds of Formula (d)

The compounds of Formula (c) are commercially available from Aldrich. The compounds of Formula (d) wherein Y is bromo are also commercially available. The preparation of the compounds of Formula (d) wherein Y is hydrogen, halo or nitro is carried out by reacting a compound of Formula (c) where Y is hydrogen, halo or nitro, with a reducing agent in an appropriate solvent at a temperature of between −5° C. and 80° C. for 1–5 hours, for example by reacting a compound of Formula (c) with borane-tetrahydrofuran complex in anhydrous tetrahydrofuran at 66° C. for 2 hours. When the reaction is substantially complete, the 2-hydroxybenzyl alcohol derivative of Formula (d) is isolated and purified by conventional means.

Preparation of Compounds of Formula (e)

The compounds of Formula (e) are prepared by reacting a compound of Formula (d) with about 1 molar equivalent of a compound of Formula (b) in the presence of a mild base, such as potassium carbonate in an inert solvent, such as acetone, ethanol, preferably methyl ethyl ketone. The reaction is carried out at a temperature of between 60°–90° C., preferably at 80° C., for 2–10 hours, preferably 6 hours. When the reaction is substantially complete, the 3-(2-hydroxymethylphenoxy)-2-propanone derivative, a compound of Formula (e), is isolated and purified by conventional means.

Preparation of Compounds of Formula (f)

The compounds of Formula (f) are prepared by reacting compounds of Formula (e) with triphenylphosphine hydrobromide in an inert solvent, such as toluene, preferably acetonitrile. The reaction is carried out at 80° C.–100° C., preferably at 90° C., for 1.5–4 hours, preferably for 2–3 hours. When the reaction is substantially complete, the benzyl triphenylphosphonium bromide derivative, a compound of Formula (f) is isolated and purified by conventional means.

Preparation of Compounds of Formula (7)

The compounds of Formula (7) are prepared by reacting a compound of Formula (f) with a strong base, such as an alkali metal alkoxide, prepared in-situ from an alkali metal, for example sodium or potassium, and absolute alcohol, preferably sodium ethoxide prepared from sodium and absolute ethanol. The reaction is carried out at 0° C. to 30° C., preferably 25° C., for 9 to 20 hours, preferably 12 hours. When the reaction is substantially complete, the 6-unsubstituted or 6-substituted-1-benzopyran derivative, a compound of Formula (7) where Y is hydrogen (7a), halo (7b), or nitro (7c), is separated and purified by conventional means.

Preparation of Compounds of Formula (9)

The preparation of compounds of Formula (9) from a compound of Formula (7b) is carried out according to the method described in Reaction Scheme I.

Preparation of Compounds of Formulae (14) and (15)

Reaction Schemes I and IA describe the means by which the intermediate compounds of Formulae (7a), (7b), (7c), (7d) and (9) are prepared. Reaction Scheme II below depicts the conversion of these intermediates to the compounds of Formulae (14) and (15).

REACTION SCHEME II

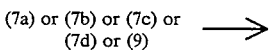

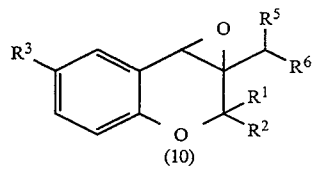

where $R^3$ is hydrogen, halo, fluoro lower alkyl, cyano, or nitro.

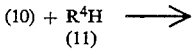

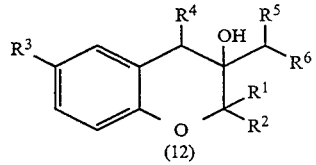

where $R^4$ is 2-oxo-1,2-dihydropyridin-1-yl, 2-oxopyrrolidin-1-yl or 1-oxoisoindolin-2-yl.

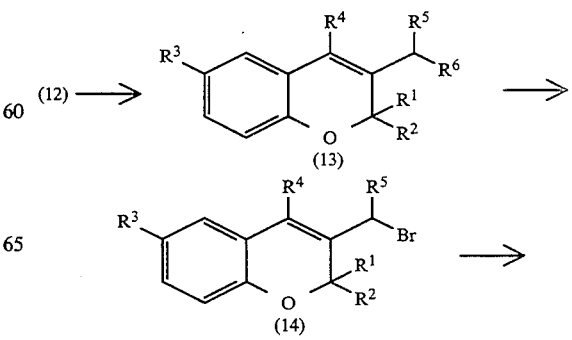

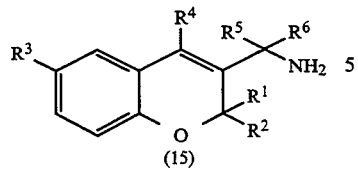

Preparation of Compounds of Formula (10)

To prepare the compounds of Formula (10), where $R^3$ is hydrogen, halo, fluoro lower alkyl, cyano, or nitro, an appropriate compound of Formulae (7a), (7b), (7c), (7d) or (9) is reacted with about 1–1.8 molar equivalents, preferably about 1.2 molar equivalents, of an epoxidizing agent, preferably m-chloroperbenzoic acid. The reaction is carried out in an inert solvent, preferably dichloromethane, at a temperature of about 0° C. to 30° C., preferably at about 25° C., for about 6–48 hours, preferably about 18 hours. When the reaction is substantially complete, the 3,4-epoxy-1-benzopyran derivative, a compound of Formula (10), is separated and purified by conventional means.

Preparation of Compounds of Formula (12)

To prepare the compounds of Formula (12), a compound of Formula (10) is reacted with about 1.5 to 4 molar equivalents, preferably about 2 molar equivalents, of an appropriate compound of Formula (11) (available from Aldrich Chemical Company), where $R^4H$ represents 2-oxo-1,2-dihydropyridine, 2-oxopyrrolidine, or 1-oxoisoindoline. The reaction is carried out in the presence of a catalytic amount of a strong quarternary organic base, preferably Triton B, in an inert solvent, preferably dioxane, at about the reflux temperature of the solvent, for about 6–48 hours, preferably about 20 hours. When the reaction is substantially complete, the 4-heterocyclic-3,4-dihydro-3-hydroxy-1-benzopyran derivative, a compound of Formula (12), is isolated and purified by conventional means.

Preparation of Compounds of Formula (13)

A compound of Formula (12) is then dehydrated by treatment with about 1–1.5 molar equivalents, preferably about 1 molar equivalent, of an alkali metal hydride, preferably sodium hydride. The reaction is carried out by refluxing in a suitable ethereal solvent (for example diethylether, dioxane, or preferably tetrahydrofuran), for about 6–32 hours, preferably about 16 hours. When the reaction is substantially complete, the 4-heterocyclic-1-benzopyran derivative, a compound of Formula (13), is separated and purified by conventional means.

Preparation of the Compounds of Formula (4)

A compound of Formula (13) is then brominated by treatment with about 1 molar equivalent of N-bromophthalimide, or preferably N-bromosuccinimide, in the presence of a catalytic amount of benzoyl peroxide. The reaction is carried out by refluxing in an inert solvent (for example dichloromethane, chloroform, or preferably carbon tetrachloride) for about 6–32 hours, preferably about 17 hours. When the reaction is substantially complete, the 4-heterocyclic-3-(bromoalkyl)-1-benzopyran derivative, a compound of Formula (14), is separated and purified by conventional means, preferably chromatography.

Preparation of the Compounds of Formula (15)

The bromo group of a compound of Formula (14) is then converted to an —NH₂ group to give a compound of Formula (15), by treatment with an excess of concentrated ammonium hydroxide. The reaction is carried out in a protic solvent (for example methanol, propanol, or preferably ethanol), for about 1–10 hours, preferably about 4 hours. When the reaction is substantially complete, the 4-heterocyclic-3-(aminoalkyl)-1-benzopyran derivative, a compound of Formula (15), is separated and purified by conventional means, preferably crystallization.

Alternative Preparation of Compounds of Formula (14) where $R^4$ is 2-oxo-1,2-dihydropyridin-1-yl Alternatively, the compounds of Formula (14) where $R^4$ is 2-oxo-1,2-dihydropyridin-1-yl may be prepared according to Reaction Scheme IIA. The precursor compound of Formula (g) wherein $R^3$ is hydrogen or halo and its preparation are disclosed in European Patent Publication No. 410,208, which is hereby incorporated by reference. The precursor compounds of Formula (g) wherein $R^3$ is nitro and cyano may also be prepared according to the method described in EP 410,208.

REACTION SCHEME IIA

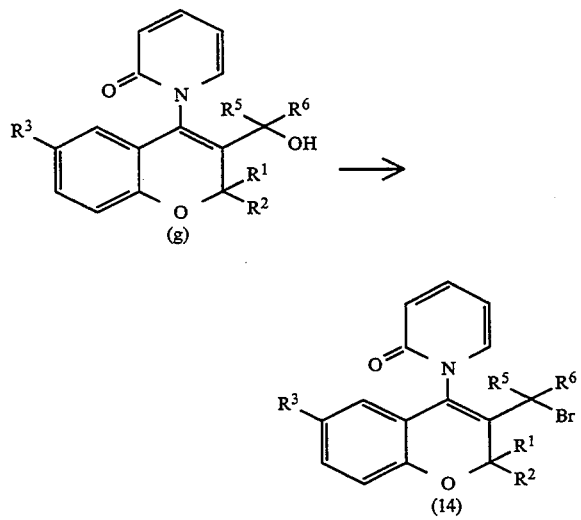

The preparation of the compound of Formula (14), wherein $R^3$ is hydrogen, halo, cyano or nitro, from the corresponding precursor compound of Formula (g) can be accomplished by conventional methods for the formation of alkyl bromides from a corresponding alcohol. The compound of Formula (g) may be reacted with a brominating agent in an inert solvent such as chloroform, dichloromethane, or toluene at a temperature ranging from 0° to 110° C. For example, the compound of Formula (g) may be reacted with phosphorous tribromide in toluene at 110° C. Such a reaction may take 1–10 hours, preferably 2 hours, to complete. When the reaction is substantially complete, the 4-heterocyclic-3-(bromoalkyl)-1-benzopyran derivative, a compound of Formula (14), is separated and purified by conventional means.

Compounds of Formula (I)

Compounds of Formula (I) may be prepared starting with the intermediates of Formulas (14) and (15). Preparation of Compounds of Formula (I) in which $R^8$ is lower alkyl, hydroxy, lower alkoxy or hydroxy lower alkyl and $R^9$ is hydrogen, lower alkyl or hydroxy lower alkyl The compounds of Formula (I) in which $R^8$ is lower alkyl, hydroxy, lower alkoxy or hydroxy lower alkyl and $R^9$ is hydrogen, lower alkyl or hydroxy lower alkyl may be divided for the sake of convenience into two groups, i.e. those compounds where $R^9$ is hydrogen and those where $R^9$ is lower alkyl or hydroxy lower alkyl.

a). The compounds of Formula (I) where $R^8$ is lower alkyl, hydroxy, lower alkoxy or hydroxy lower alkyl, and $R^9$ is hydrogen, are prepared from compounds of Formula (14) as shown in Reaction Scheme III. Because such compounds are used as starting materials in the synthesis of other compounds of Formula (I) (for example in Reaction Scheme IV), for the sake of clarity the compounds are identified as compounds of Formula (IA). They are prepared by reacting (14) with an amine of the formula $R^8NH_2$, where $R^8$ is lower alkyl, hydroxy, lower alkoxy or hydroxy lower alkyl.

b). The compounds of Formula (I) where $R^8$ is lower alkyl, hydroxy, lower alkoxy or hydroxy lower alkyl and $R^9$ is lower alkyl or hydroxy lower alkyl, are also prepared from compounds of Formula (14) as shown in Reaction Scheme III, by reacting (14) with an amine of the formula $R^8R^9NH$, where $R^8$ is lower alkyl, hydroxy, lower alkoxy or hydroxy lower alkyl and $R^9$ is lower alkyl or hydroxy lower alkyl.

REACTION SCHEME III

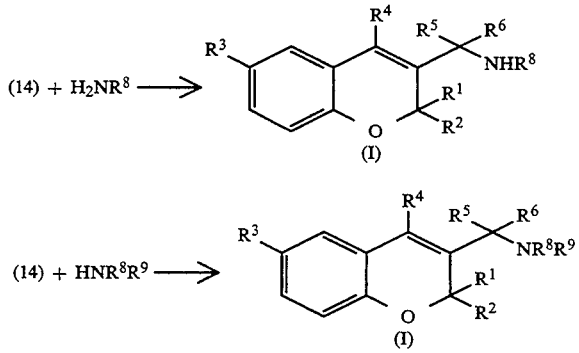

One method of preparing the compounds of Formula (I) or (IA) where $R^8$ is lower alkyl, hydroxy, lower alkoxy or hydroxy lower alkyl and $R^9$ is hydrogen, lower alkyl or hydroxy lower alkyl, is to react a compound of Formula (14) with about 1 to 4 molar equivalents, preferably about 1.1 molar equivalents, of an appropriate amine of formula $HNR^8R^9$ (for example, methylamine, dimethylamine, 2-hydroxyethylamine, and the like). The reaction is carried out in a protic solvent, preferably methanol, optionally in the presence of water, at a temperature of about 0° C. to 30° C., preferably at about 25° C., for about 1-10 hours, preferably about 4 hours. When the reaction is substantially complete, the 4-heterocyclic-3-(substituted aminoalkyl)-1-benzopyran derivative, a compound of Formula (I) or (IA), is separated and purified by conventional means, preferably crystallization. This method of preparation is preferred where $R^8$ is lower alkyl or hydroxy lower alkyl and $R^9$ is hydrogen, lower alkyl or hydroxy lower alkyl.

Alternatively, a compound of Formula (14) is reacted with about 1 molar equivalent of an appropriate amine of formula $HNR^8R^9$ in a protic solvent, preferably ethanol, at a temperature of about the reflux temperature of the solvent, for about 5 minutes to 2 hours, preferably about 30 minutes. When the reaction is substantially complete, the 4-heterocyclic-3-(substituted aminoalkyl)-1-benzopyran derivative, a compound of Formula (I) or (IA), is separated and purified by conventional means, preferably crystallization. This method of preparation is preferred where $R^8$ is hydroxy or lower alkoxy and $R^9$ is hydrogen or lower alkyl.

Preparation of Compounds of Formula (I) in which $R^8$ is hydrogen, lower alkyl, lower alkoxy, hydroxy, or hydroxy lower alkyl, and $R^9$ is $-SO_2R^{10}$, $-CO_2R^{10}$, $-C(O)NR^{11}R^{12}$, $-C(S)NR^{11}R^{12}$, or $-C(O)R^{12}$ The compounds of Formula (I), in which $R^8$ is hydrogen, lower alkyl, lower alkoxy, hydroxy, or hydroxy lower alkyl, and $R^9$ is $-SO_2R^{10}$, $-CO_2R^{10}$, $-C(O)NR^{11}R^{12}$, $-C(S)NR^{11}R^{12}$, or $-C(O)R^{12}$, in which $R^{10}$, $R^{11}$ and $R^{12}$ are as defined, are prepared as illustrated in Reaction Scheme IV below.

REACTION SCHEME IV

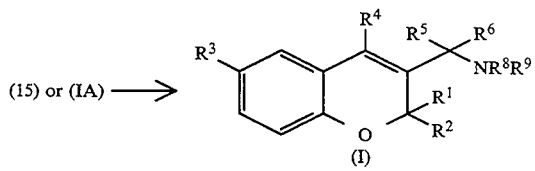

where $R^8$ is as defined and $R^9$ is $-SO_2R^{10}$, $-CO_2R^{10}$, $-C(O)NR^{11}R^{12}$, $-C(S)NR^{11}R^{12}$, or $-C(O)R^{12}$.

A. Compounds of Formula (I) where $R^9$ is $-C(O)R^{12}$, where $R^{12}$ is hydrogen To prepare the compounds of Formula (I) where $R^8$ is as defined above and $R^9$ is $-C(O)R^{12}$, where $R^{12}$ is hydrogen, an appropriate compound of Formula (15) or (IA) is reacted with a large excess of a lower alkyl formate as a solvent, preferably methyl formate, at reflux temperature, for about 10 hours to 3 days, preferably about 27 hours. When the reaction is substantially complete, the 4-heterocyclic-3-formamidoalkyl-1-benzopyran derivative, a compound of Formula (I) where $R^8$ is as defined above and $R^9$ is $-CHO$, is isolated and purified by conventional means, preferably crystallization.

B. Compounds of Formula (I) where $R^9$ is $-C(O)R^{12}$
(1) Where $R^{12}$ is lower alkyl or fluoro lower alkyl To prepare compounds of Formula (I) where $R^8$ is as defined and $R^9$ is $-C(O)R^{12}$, where $R^{12}$ is lower alkyl or fluoro lower alkyl, an appropriate compound of Formula (15) or (IA) is reacted with about 1 to 2 molar equivalents, preferably about 1.2 molar equivalents, of an acylating agent, preferably an acyl anhydride of Formula $(R^{12}CO)_2O$, where $R^{12}$ is lower alkyl or fluoro lower alkyl, in the presence of about 1 to 1.5 molar equivalents, preferably about 1.2 molar equivalents, of a tertiary base, preferably triethylamine. The reaction is carried out in an inert solvent, preferably dichloromethane, preferably at about 25° C. where $R^8$ is lower alkyl, lower alkoxy or hydroxy lower alkyl, and preferably at about 0° C. where $R^8$ is hydroxy. The reaction is carried out for about 1-10 hours, preferably about 4 hours where $R^{12}$ is fluoro lower alkyl and preferably about 8 hours where $R^{12}$ is lower alkyl. When the reaction is substantially complete, the 4-heterocyclic-3-(amido)alkyl-1-benzopyran derivative, a compound of Formula (I) where $R^8$ is as defined and $R^9$ is $-C(O)R^{12}$, where $R^{12}$ is lower alkyl or fluoro lower alkyl, is isolated and purified by conventional means, preferably crystallization.

(2) Where $R^{12}$ is lower alkyl

An alternative preparation of compounds of Formula (I) where $R^8$ is as defined and $R^9$ is —C(O)$R^{12}$, where $R^{12}$ is lower alkyl, starts as for B(1) with an appropriate compound of Formula (15) or (IA), which is reacted with about 1 to 2 molar equivalents, preferably about 1.2 molar equivalents, of an acylating agent, preferably an acyl halide of formula $R^{12}$COCl or $R^{12}$COBr, where $R^{12}$ is lower alkyl, in the presence of about 1 to 1.5 molar equivalents, preferably about 1.2 molar equivalents, of a tertiary base, preferably triethylamine. The reaction is carried out in an inert solvent, preferably dichloromethane, preferably at about 25° C. where $R^8$ is lower alkyl, lower alkoxy or hydroxy lower alkyl, and preferably at about 0° C. where $R^8$ is hydroxy. The reaction is carried out for about 1–10 hours, preferably about 4 hours. When the reaction is substantially complete, the 4-heterocyclic-3-(alkylamido)alkyl-1-benzopyran derivative, a compound of Formula (I) where $R^8$ is as defined and $R^8$ is —C(O)$R^{12}$, where $R^{12}$ is lower alkyl, is isolated and purified by conventional means, preferably crystallization.

C. Compounds of Formula (I) where $R^9$ is —CO$_2R^{10}$

To prepare compounds of Formula (I) where $R^8$ is as defined and $R^9$ is —CO$_2R^{10}$, where $R^{10}$ is lower alkyl, an appropriate compound of Formula (15) or (IA) is reacted about with about 1 to 2 molar equivalents, preferably about 1.2 molar equivalents, of a lower alkyl chloroformate of the formula ClCO$_2R^{10}$, in the presence of about 1 to 1.5 molar equivalents, preferably about 1.2 molar equivalents, of a tertiary base, preferably triethylamine. The reaction is carried out in an inert solvent, preferably dichloromethane, at about 0° C. to 30° C., preferably about 2 hours. When the reaction is substantially complete, the 4-heterocyclic-3-(carbamoyl)alkyl-1-benzopyran derivative, a compound of Formula (I) where $R^8$ is as defined and $R^9$ is —CO$_2R^{10}$, where $R^{10}$ is lower alkyl, is isolated and purified by conventional means, preferably crystallization or chromatography.

D. Compounds of Formula (I) where $R^9$ is —C(O)NR$^{11}R^{12}$

To prepare compounds of Formula (I) where $R^8$ is as defined above and $R^9$ is —C(O)NR$^{11}R^{12}$, where $R^{11}$ is hydrogen and $R^{12}$ is lower alkyl or fluoro lower alkyl, an appropriate compound of Formula (15) or (IA) is reacted with an isocyanate of the formula $R^{12}$NCO (e.g. ethyl isocyanate). The reaction is carried out in an inert solvent, preferably dichloromethane, at a temperature of about 0° C. to about 30° C., preferably at about 25° C., for about 1 to 5 hours, preferably about 2 hours. When the reaction is substantially complete, the 4-heterocyclic-3-(ureido)alkyl-1-benzopyran derivative, a compound of Formula (I) where $R^8$ is as defined and $R^9$ is —C(O)NR$^{11}R^{12}$, where $R^{11}$ is hydrogen and $R^{12}$ is lower alkyl or fluoro lower alkyl, is isolated and purified by conventional means, preferably chromatography.

Alternatively, to prepare compounds of Formula (I) where $R^8$ is as defined above and $R^9$ is —C(O)NR$^{11}R^{12}$, where $R^{11}$ and $R^{12}$ are both hydrogen, an appropriate compound of Formula (15) or (IA) is reacted with a trialkylsilylisocyanate, preferably trimethylsilyl isocyanate. The reaction is carried out in an inert solvent, preferably tetrahydrofuran, under nitrogen, at a temperature of about 0° C. to about 30° C., preferably at about 25° C., for about 10 to 18 hours, preferably about 12 hours. When the reaction is substantially complete, the 4-heterocyclic-3-(ureido)alkyl-1-benzopyran derivative, a compound of Formula (I) where $R^8$ is as defined and $R^9$ is —C(O)NR$^{11}R^{12}$, where $R^{11}$ is hydrogen and $R^{12}$ is hydrogen, is isolated and purified by conventional means, preferably chromatography.

Alternatively, to prepare compounds where $R^{11}$ is not hydrogen an appropriate compound of Formula (15) or (IA) is reacted with a compound of the formula WC(O)NR$^{11}R^{12}$, where W is chloro or bromo (e.g. dimethylcarbamoyl chloride). The reaction is carried out in the presence of about 1 to 1.5 molar equivalents, preferably about 1.2 molar equivalents, of a tertiary base, in an inert solvent, at about 0° C. to 30° C., for about 1–5 hours.

E. Compounds of Formula (I) where $R^9$ is —C(S)NR$^{11}R^{12}$

To prepare compounds of Formula (I) where $R^8$ is as defined above and $R^9$ is —C(S)NR$^{11}R^{12}$, where $R^{11}$ is hydrogen and $R^{12}$ is lower alkyl or fluoro lower alkyl, an appropriate compound of Formula (15) or (IA) is reacted with an isothiocyanate of the formula $R^{12}$NCS (e.g. methyl isothiocyanate). The reaction is carried out in an inert solvent, preferably dichloromethane, at a temperature of about 0° C. to about 30° C., preferably at about 25° C., for about 10 hours to about 3 days, preferably about 26 hours. When the reaction is substantially complete, the 4-heterocyclic-3-(thioureido)alkyl-1-benzopyran derivative, a compound of Formula (I) where $R^8$ is as defined and $R^9$ is —C(S)NR$^{11}R^{12}$, where $R^{11}$ is hydrogen and $R^{12}$ is lower alkyl or fluoro lower alkyl, is isolated and purified by conventional means, preferably chromatography.

Alternatively, to prepare compounds of Formula (I) where $R^8$ is as defined above and $R^9$ is —C(S)NR$^{11}R^{12}$, where $R^{11}$ and $R^{12}$ are both hydrogen, an appropriate compound of Formula (15) or (IA) is reacted with a trialkylsilyl isothiocyanate, preferably trimethylsilyl isothiocyanate. The reaction is carried out in an inert solvent, preferably tetrahydrofuran, at a temperature of about 0° C. to about 30° C., preferably at about 25° C., for about 1 to 4 hours, preferably about 2 hours. When the reaction is substantially complete, the 4-heterocyclic-3-(thioureido)alkyl-1-benzopyran derivative, a compound of Formula (I) where $R^8$ is as defined and $R^9$ is —C(S)NR$^{11}R^{12}$, where $R^{11}$ is hydrogen and $R^{12}$ is hydrogen, is isolated and purified by conventional means.

Alternatively, to prepare compounds where $R^{11}$ is not hydrogen an appropriate compound of Formula (15) or (IA) is reacted with a compound of the formula WC(S)NR$^{11}R^{12}$, where W is chloro or bromo. The reaction is carried out in the presence of about 1 to 1.5 molar equivalents, preferably about 1.2 molar equivalents, of a tertiary base, in an inert solvent, at about 0° C. to 30° C., for about 1–5 hours.

F. Compounds of Formula (I) where $R^9$ is —SO$_2R^{10}$

To prepare compounds of Formula (I) where $R^8$ is as defined above and $R^9$ is —SO$_2R^{10}$, where $R^{10}$ is lower alkyl, an appropriate compound of Formula (15) or (IA) is reacted with about 1 to 1.5 molar equivalents, preferably about 1 molar equivalent, of a lower alkyl sulfonyl halide of the formula $R^{10}$SO$_2$Cl or $R^{10}$SO$_2$Br. The reaction is carried out in the presence of about 1 to 1.5 molar equivalents, preferably about 1.1 molar equivalents, of a tertiary base, preferably triethylamine, in an inert solvent, preferably dichloromethane. The reaction is conducted at a temperature of about 0° C. to 30° C., preferably at about 25° C., for about 1–10 hours, preferably about 4 hours. When the reaction is substantially complete, the 4-heterocyclic-3-(sulfonamido)alkyl-1-benzopyran derivative, a compound of Formula (I) where $R^8$ is as defined and $R^9$ is $-SO_2R^{10}$, where $R^{10}$ is lower alkyl, is isolated and purified by conventional means.

Alternative Preparation of Compounds of Formula (I)

Reaction Schemes (I) to (IV) above illustrate the preparation of compounds of Formula (I) using a sequence that comprises preparing substituted benzopyrans (7) and (9), converting them to 3,4-epoxy derivatives (10), reacting (10) with $R^4H$ to introduce the $R^4$ moiety at the 4-position, dehydrating the 3,4-dihydro compounds (12) thus produced back to benzopyrans (13), followed by selectively brominating the 3-alkyl moiety. The bromo compounds (14) thus produced may then be converted to the various compounds of Formula (I).

It should be understood that the above sequence of reaction steps can be changed to achieve the same result. That is, the substituted compounds (7) or (9) can first be brominated to give compounds of Formula (16), which are then converted to the compounds of Formula (I) by methods analogous to those used in Reaction Schemes II, III and IV, as shown in Reaction Scheme V below:

REACTION SCHEME V

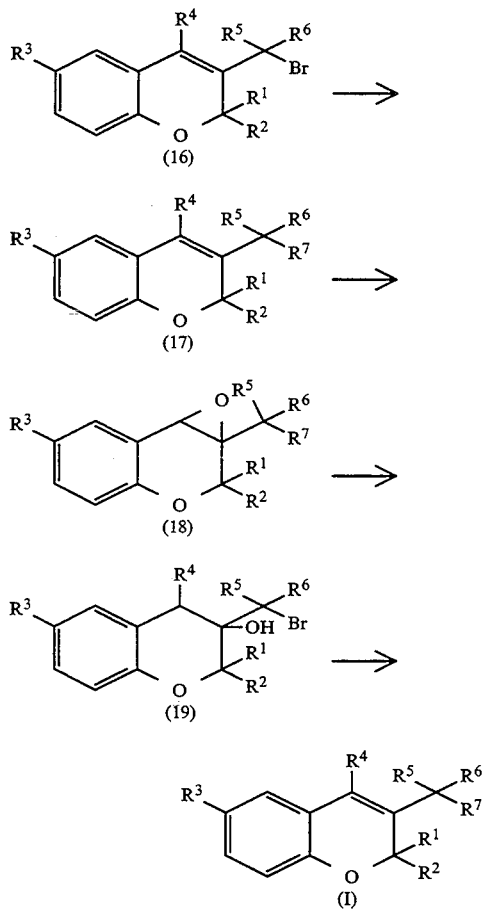

Each reaction step of Reaction Scheme V is carried out in the same manner as shown in Reaction Schemes II, III and IV. For example, the first step of Reaction Scheme V is the bromination of a 3-alkyl group to give a compound of the Formula (16). The reaction conditions correspond to those used in Reaction Scheme II, step 4. Conversion of the bromo group of (16) to $-NR^8R^9$ may be accomplished by any of the procedures shown in Reaction Schemes III and IV. Step 3 of Reaction Scheme V is an epoxidation of a double bond. The reaction conditions correspond to those used in Reaction Scheme II, step 1.

It should be noted that, upon treatment of the compound of Formula (18) with 2-oxopyrrolidine or 1-oxoisoindoline, the 3-hydroxy compound of Formula (19) thus formed dehydrates spontaneously to give the desired compound of Formula (I), i.e. no alkali metal hydride treatment is necessary. However, with regard to reaction of (18) with 2-oxo-1,2-dihydropyridine, the 3-hydroxy derivative of Formula (19) is stable, and requires dehydration as shown in Reaction Scheme II.

It should also be noted that for the compound of Formula (17) in which $R^8$ is hydroxy (i.e. $R^7$ is $-NR^8R^9$), the hydroxy group should first be protected by conversion to, for example, a benzyl ether, a benzoyl derivative, a tetrahydropyranyl ether, and the like, by methods well known to those skilled in the art. This protecting group is then removed as a final step.

Purification of Compounds of Formula (I) and Intermediates

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Examples hereinbelow. However, other equivalent separation or isolation procedures could, of course, also be used.

The salt products are also isolated by conventional means. For example, the reaction mixtures may be evaporated to a dryness, and the salts can be further purified by conventional methods such as those listed above.

Salts of Compounds of Formula (I)

Acid Addition Salts

The compounds of Formula (I) may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at 0°–50° C. The resulting salt precipitates spontaneously or may be brought out of solution with a less polar solvent.

The acid addition salts of the compounds of Formula (I) may be converted to the corresponding free bases by treatment with at least a stoichiometric amount of a suitable base such as sodium or potassium hydroxide, potassium carbonate, sodium bicarbonate, ammonia, and the like.

Base Addition Salts

The compounds of this invention where $R^8$ is hydroxy and $R^9$ is —C(O)$R^{12}$ can form base addition salts, which may be prepared from either inorganic or organic bases. Salts derived from inorganic bases include, but are not limited to, the sodium, potassium, lithium, ammonium, calcium, magnesium, ferrous, zinc, copper, manganous, aluminum, ferric, and manganic salts, and the like. Preferred inorganic salts are the ammonium, sodium, potassium, calcium, and magnesium salts. Salts derived from organic bases include, but are not limited to, salts of primary, secondary and tertiary amines, substituted amines including naturally-occuring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procains, hydrabamine, choline, betains, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline. Typically, the compound of Formula (I) where $R^8$ is hydroxy and $R^9$ is —C(O)$R^{12}$ is dissolved in an inert organic solvent such as diethyl ether, ethyl acetate, chloroform, ethanol or methanol and the like, and the base added in a suitable solvent. The temperature is maintained at 0°–50° C. The resulting salt precipitates spontaneously or may be brought out of solution with a less polar solvent.

In summary, the compounds of the present invention are made by the procedures outlined below:

1. A process for preparing compounds of the Formula (I), wherein:

$R^1$ and $R^2$ are independently hydrogen or lower alkyl, or when taken together with the carbon to which they are attached are cycloalkyl of 3 to 8 carbon atoms;

$R^3$ is hydrogen; halo; fluoro lower alkyl; cyano; or nitro;

$R^4$ is

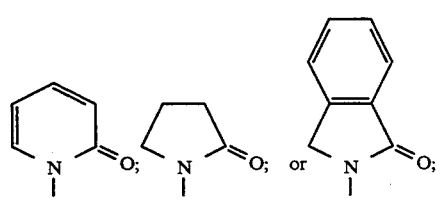

$R^5$ and $R^6$ are independently hydrogen or lower alkyl; and $R^7$ is —NR$^8$R$^9$; wherein:

$R^8$ is lower alkyl; lower alkoxy; hydroxy; or hydroxy lower alkyl; and;

$R^9$ is hydrogen; lower alkyl; hydroxy lower alkyl;

comprises:

(a) reacting a compound of the formula:

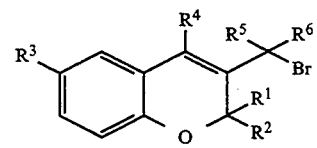

with an amine derivative of the formula HNR$^8$R$^9$, where $R^8$ and $R^9$ are as defined above; or (b) reacting the free base of the compound of Formula (I) with an acid to give a pharmaceutically acceptable acid addition salt; or (c) reacting an acid addition salt of the compound of Formula (I) with a base to give the corresponding free base; or (d) converting an acid addition salt of the compound of Formula (I) to another pharmaceutically acceptable acid addition salt of Formula (I).

2. Alternatively, a process for preparing compounds of the Formula (I), wherein $R^1$, $R^2$, $R^3$, $R^4$, $R^5$, $R^6$, $R^7$ and $R^8$ are as defined; and $R^9$ is —C(O)$R^{12}$, where $R^{12}$ is hydrogen;

comprises reacting a compound of the formula:

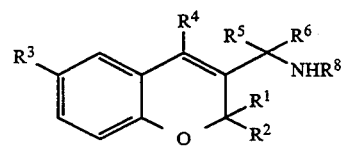

with a lower alkyl formate.

3. Alternatively, a process for preparing compounds of the Formula (I), wherein $R^1$, $R^2$, $R^3$, $R^4$, $R^5$, $R^6$, $R^7$ and $R^8$ are as defined; and $R^9$ is —SO$_2$R$^{10}$; —CO$_2$R$^{10}$; —C(O)NR$^{11}$R$^{12}$; —C(S)NR$^{11}$R$^{12}$; or —C(O)R$^{12}$; wherein $R^{10}$ and $R^{11}$ are lower alkyl; and $R^{12}$ is lower alkyl, or fluoro lower alkyl;

comprises reacting a compound of the formula:

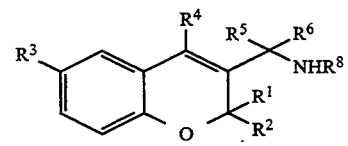

with a compound of the formula WSO$_2$R$^{10}$, WCO$_2$R$^{10}$, WCOR$^{12}$, (R$^{12}$CO)$_2$O, WC(O)NR$^{11}$R$^{12}$ or WC(S)NR$^{11}$R$^{12}$, where W is chloro or bromo and R$^{10}$, R$^{11}$ and R$^{12}$ are as defined above.

4. Alternatively, a process for preparing compounds of Formula (I), wherein $R^1$, $R^2$, $R^3$, $R^4$, $R^5$, $R^6$, $R^7$ and $R^8$ are as defined; and $R^9$ is —C(O)NHR$^{12}$ or —C(S)NHR$^{12}$; wherein $R^{12}$ is lower alkyl or fluoro lower alkyl;

comprises reacting a compound of the formula:

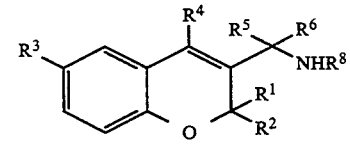

with a compound of the formula R$^{12}$NCO or R$^{12}$NCS.

5. Alternatively, a process for preparing compounds of Formula (I), wherein $R^1$, $R^2$, $R^3$, $R^4$, $R^5$, $R^6$, $R^7$ and $R^8$ are as defined; and $R^9$ is —C(O)NHR$^{12}$ or —C(S)NHR$^{12}$; wherein $R^{12}$ is hydrogen;

comprises reacting a compound of the formula:

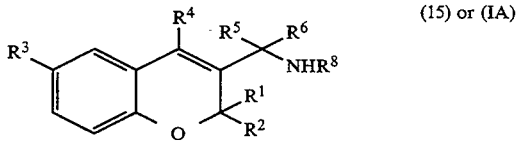

(15) or (IA)

with a trialkylsilyl isocyanate or a trialkylsilyl isothiocyanate.

6. Alternatively, a process for preparing compounds of Formula (I), wherein $R^1$, $R^2$, $R^3$, $R^4$, $R^5$, $R^6$, $R^7$, $R^8$ and $R^9$ are as defined;

comprises reacting a compound of the formula:

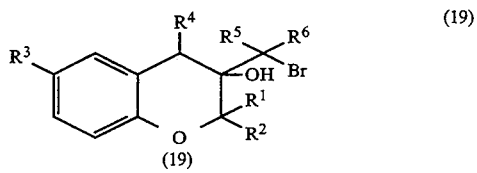

(19)

with an alkaline metal hydride.

Utility and Administration

A. General Utility

The compounds of the present invention exhibit useful pharmacological properties in mammals, including potassium channel activating properties. Consequently the compounds of the present invention have important pharmacological effects on a variety of tissues, including smooth and cardiac muscle. See, for example, *J. Med. Chem.*, Vol. 33, pp 1529-1541 (1990), *Drugs*, Vol. 40, pp 785-791 (1990), *Trends in Pharmacological Sciences*, Vol. 11, pp 417-422 (1990).

For example, the compounds of Formula (I) demonstrate the ability to relax smooth muscle and are therefore useful in the treatment of mammals where the use of smooth muscle relaxants is indicated, and are particularly useful in the treatment of essential and pulmonary hypertension, congestive heart failure, angina, peripheral vascular occlusive disease, coronary and cerebral vasospasms, smooth muscle spasm and stroke.

These derivatives are also useful in treating disorders associated with smooth muscle contractions of the gastro-intestinal tract, uterus or the urinary tract, including the ureter. Such disorders include, but are not limited to, irritable bowel syndrome, premature labor, dysmenorrhea, incontinence, renal failure, urinary retention, renal colic and disorders associated with the passage of kidney stones.

These derivatives also exhibit bronchodilating activity and are therefore useful in treating disorders of the respiratory tract. Such disorders include, but are not limited to, reversible airways obstruction and asthma.

As potassium channel activators, the compounds are also useful in treating cardiac arrhythmia, myocardial infarction, cardiac ischaemic disease and angina.

The compounds are also useful in the treatment of glaucoma, central nervous system disorders, such as epilepsy and psycho-depressive conditions; and in treating baldness. Other pathologies linked to ageing, ischemia, inflammation or oedema (for example of the brain), to proliferative diseases at organ or skin level, and to metabolic diseases associated with obesity and glycoregulation disorders can be treated or prevented by treatment with the compounds of the invention.

The compounds of the present invention also exhibit 5-lipoxygenase inhibiting properties, and consequently have important pharmacological effects. See, for example, *Comprehensive Medicinal Chemistry*, Vol. 2, pp. 147-173 (1990), *Annual Reports in Medicinal Chemistry*, Vol. 17, pp. 203-217 (1982), *Annual Reports in Medicinal Chemistry*, Vol. 24, pp.61-70 and pp. 71-79 (1990), *Advances in Prostaglandin thromboxane and leukotriene research*, Vol. 21, pt a-b, pp. 109-112 (1990), *Drugs of the Future*, Vol. 16, pp. 547-558 (1991), *Journal of Ocular Pharmacology*, Vol. 4 (1), pp. 43-49 (1988).

The compounds of Formula (I) are therefore useful in the treatment of pain and inflammatory conditions including treatment of rheumatoid arthritis, osteoarthritis, bursitis, tendonitis, gout, and eye inflammation caused for example by ocular hypertension leading to glaucoma.

As 5-lipoxygenase inhibitors they are also useful in treating allergic chronic obstructive lung diseases e.g. asthma, bronchitis, emphysema, collapsed lung, and pulmonary hypertonia.

The compounds are also useful in treating hyperproliferative disorders such as psoriasis.

The compounds are also useful in the treatment of ulcerative colitis and stroke.

B. Testing

The compounds of Formula (I) exhibit potassium channel activating properties, which may be determined by a variety of in vitro assays known to those skilled in the art; see, for example, *J. Pharm. Exp. Ther.*, Vol. 248, pp 1261-1268 (1989), or a modification thereof.

The smooth muscle relaxant properties of these compounds may be determined by in vitro and/or in vivo assays. For example see the in vitro assay described in Taylor S. G., et al., *Brit. J. Pharmacol.*, Vol. 94, pp. 853-863 (1988), or a modification thereof.

The antihypertensive activity of the compounds may be determined in conscious spontaneous hypertensive rats prepared with indwelling arterial catheter by the invivo assay described in Popovic V. and Popovic P., *J. Applied. Physiol.*, Vol. 15, pp. 727-728 (1960), or a modification thereof.

The compounds of Formula (I) also exhibit bronchodilating properties. This property may be determined in guinea pigs by the in vivo assay described in Dixon W. E. and Brodie T. G., *J. of Physiol.*, Vol. 29, pp. 97-173 (1903), or a modification thereof.

The anti-glaucoma properties of these compounds may be determined in rabbits by the in-vivo assay described in L. D. Waterbury, *Investigative Ophthalmology and Visual Science*, Vol. 31, pp. 2560-2567 (1990), or a modification thereof.

The compounds of Formula (I) also exhibit selective peripheral vasodilator properties, which may be determined in rats by the in-vivo assay described in *Naunyn-Schmiedeberg's Arch. Pharmacol.*, Vol. 337, pp. 341-346 (1988).

The compounds of Formula (I) also exhibit 5-lipoxygenase inhibiting properties, which may be determined in human blood by the in-vito assay described in Example 28, as is well accepted in the art (see Radmark et al., *Febs Letters*, Vol. 110(2), pp 213–215 (1980).

C. General Administration

In applying the compounds of this invention to treatment of the above conditions, any pharmaceutically acceptable mode of administration can be used, either alone or in combination with other pharmaceutically acceptable excipients, including solid, semi-solid liquid, nebulized or aerosol dosage forms, such as, for example, tablets, capsules, powders, liquids, suspensions, suppositories, aerosols or the like, or in sustained or controlled release dosage forms for the prolonged administration of the compound at a predetermined rate, preferably in unit dosage forms suitable for single administration of precise dosages. The compositions will typically include a conventional pharmaceutical carrier or excipient and an active compound of Formula (I) or the pharmaceutically acceptable salts thereof. In addition, these compositions may include other medicinal agents, pharmaceutical agents, carriers, adjuvants, etc., e.g. antihypertensive agents such as angiotensin converting enzyme (ACE) inhibitors, beta-blocking agents and diuretics; bronchodilating agents and antiasthmatics; steroids; antiinflammatories; and non-steroidal antiinflammatories (NSAIDs).

The amount of active compound administered will, of course, be dependent on the subject and disease state being treated, the severity of the affliction, the manner of administration and the judgment of the prescribing physician. However, an effective dosage is in the range of about 0.00003 mg to about 20 mg/kg of body weight, preferably about 0.0003 mg to 2 mg/kg. For an average 70 kg human, this would amount to about 0.002–1400 mg per day, or preferably 0.02–140 mg/day.

For solid compositions, conventional non-toxic solid carriers include, for example, pharmaceutical grades of mannitol, lactose, starch, magnesium stearate, talcum, cellulose derivatives, glucose, sucrose, magnesium carbonate, polyvinyl pyyrolidone, saturated polyglycolysed glycerides, glycerol esters of mixtures of saturated vegetable fatty acids, and the like, may be used. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of non-toxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active ingredient (compounds of Formula (I)) in the range of 0.005% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, glucose, sucrose, magnesium carbonate, and the like. Such compositions take the form of solutions, suspensions, tablets, capsules, powders, sustained release formulations and the like. Such compositions may contain 0.01%–95% active ingredient, preferably 0.1–50%.

For a solid dosage form, the solution or suspension, in for example propylene carbonate, vegetable oils or triglycerides, is preferably encapsulated in a gelatin capsule. Such diester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing compounds of Formula (I) or their salts in vegetable oils, glycols, triglycerides, propylene glycol esters (e.g. propylene carbibate) and the like, and encapsulating these solution or suspension in hard or soft gelatin capsule shells.

Other useful formulations include those set forth in U.S. Pat. Nos. Re. 28,819 and 4,358,603.

The formulation can be administered in a single unit dosage form for continuous treatment or in a single unit dosage form ad libitum when relief of symptoms is specifically required.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2–2% of the active agent in solution.

Nasal administration is generally characterized by inhalation of the compounds of Formula (I) alone or in combination with other pharmaceutically acceptable excipients.

Formulations of compounds of Formula (I) may also be administered to the respiratory tract as an aerosol or solution for a nebulizer, or as a microfine powder for insufflation, alone or in combination with an inert carrier such as lactose, for the treatment of reversible airways obstruction and asthma. In such a case, the particles of the formulation have diameters of less than 50 microns, preferably less than 10 microns.

Pharmaceutical compositions suitable for the treatment of glaucoma may be prepared by mixing the active compound with a non-toxic pharmaceutical organic carrier, or with a pharmaceutically acceptable inorganic carrier. Typical of such pharmaceutically acceptable carriers are, for example, water, mixtures of water and water-miscible solvents such as lower alkanols or vegetable oils, glycerol, polyalkylene glycols, hydroxyethyl cellulose, ethyl oleate, carboxymethyl cellulose, polyvinylpyyrolidone, other polymers water miscible such as cellulose derivatives (methylcellulose, carboxymethylcellulose alkaline derivative, hydroxymethylcellulose, hydroxyethylcellulose) and other conventionally employed acceptable carriers. The pharmaceutical composition may also contain non-toxic auxiliary substances such as emulsifying, preserving, wetting, bodying agents and the like, as for example, polyethylene glycols 200, 300, 400, and 600; carbowaxes 1,000, 1,500, 4,000, 6,000 and 10,000; a polyanionic polymer, e.g. a carboxyvinylpolymer having a molecular weight of from about 4,000 to about 6,000,000; antibacterial components such as quaternary ammonium compounds, phenylmercuric salts known to have cold sterilizing properties and which are non-injurious in use; thimerosol, methyl and propylparaben, benzylic alcohol, phenylethanol; buffering ingredients and isotonic agents such as alkali metal chloride, borate, acetate, gluconate buffers; antioxidant agents such as sodium metabisulfite, butylated hydroxyanisol, butylated hydroxytoluene and other conventional ingredients such as sorbitan monolaurate, triethanolamine oleate, polyoxyethylene sorbitan monopalmitate, dioctyl alkali metal sulfosuccinate, monothioglycerol, ethylenediamine tetraacetic and the like.

The following Preparations and Examples illustrate the invention but are not intended to limit its scope.

PREPARATION 1

Preparation of Compounds of Formula (3)

A. Preparation of Formula (3) where X is hydrogen, $R^1$ and $R^2$ are methyl, and $R^5$ and $R^6$ are hydrogen A solution of 2-hydroxypropiophenone (500 ml, 3.64 mol), acetone (400 ml), and pyrrolidine (150 ml, 1.8 mol) in toluene (1000 ml) was heated at 85° C. for 66 hours. The cooled solution was then washed successively with water, aqueous hydrochloric acid and aqueous sodium hydroxide solution. The toluene layer was separated and the solvent removed under reduced pressure. The residue was chromatographed on silica gel, eluting with dichloromethane/heptane (50/50), to give 81 g of 2,2,3-trimethyl-3,4-dihydro-2H-1-benzopyran-4-one as an oil, a compound of Formula (3a); $^1$H NMR (CDCl$_3$): $\delta$1.3 (d,3H), 1.4 (s,3H), 1.6 (s,3H), 2.5–3.0 (q,1H), 6.8–8.1 (m,4H).

B. Preparation of Formula (3) where X is bromine, $R^1$ and $R^2$ are methyl, and $R^5$ and $R^6$ are hydrogen Similarly, replacing 2-hydroxypropiophenone with 2-hydroxy-5-bromo-propiophenone and following the procedure of Preparation 1A above, the following compound of Formula (3) was obtained:

6-bromo-2,2,3-trimethyl-3,4-dihydro-2H-1-benzopyran-4-one as an oil, a compound of Formula (3b); $^1$H NMR (CDCl$_3$): $\delta$1.2 (d,3H), 1.3 (s,3H), 1.5 (s,3H), 2.7 (q,1H), 6.8 (d,1H), 7.5 (d,1H), 7.9 (s,1H).

PREPARATION 2

Preparation of Compounds of Formula (4)

Preparation of Formula (4) where $R^1$ and $R^2$ are methyl, and $R^5$ and $R^6$ are hydrogen To a solution of 2,2,3-trimethyl-3,4-dihydro-2H-1-benzopyran-4-one (81 g, 0.426 mol) in concentrated sulfuric acid (695 ml) at 0° C. was added a solution containing concentrated sulfuric acid (30 ml) and nitric acid (65%, 175 ml) while maintaining the temperature below 5° C. After stirring for three hours at 5° C., the mixture was added to ice/water and the crude product recovered by filtration. This product was dried and washed with diisopropyl ether to give 44 g of 6-nitro-2,2,3-trimethyl-3,4-dihydro-2H-1-benzopyran-4-one, m.p. 78° C.

PREPARATION 3

Preparation of Compounds of Formula (5)

Preparation of Formula (5) where $R^1$ and $R^2$ are methyl, and $R^5$ and $R^6$ are hydrogen A. A mixture of of 6-nitro-2,2,3-trimethyl-3,4-dihydro-2H-1-benzopyran-4-one (23.5 g, 0.1 mol) and 10% palladium on carbon (2 g) in methanol was stirred under an atmosphere of hydrogen at 40°–50° C. for five hours at atmospheric pressure. The solution was then filtered, and the solvent removed from the filtrate under reduced pressure to give 21 g of 6-amino-2,2,3-trimethyl-3,4-dihydro-2H-1-benzopyran-4-one as an oil. B. To a mixture of water (293 ml) and concentrated hydrochloric acid (25.7 ml) at 0° C. was added a solution of 6-amino-2,2,3-trimethyl-3,4-dihydro-2H-1-benzopyran-4-one (20.5 g, 0.1 mol) in ethanol (140 ml). A solution of sodium nitrite (7.6 g, 0.11 mol) in water (90 ml) was then added, such that the temperature did not rise above 0° C. After fifteen minutes at 0° C., the reaction mixture was poured into a solution containing potassium cyanide (58.6 g, 0.90 mol) and cuprous cyanide (80.61 g, 0.90 mol) in water at 90° C., whilst maintaining the temperature of the reaction above 70° C. The resulting mixture was heated at 90° C. for one hour and then cooled to 20° C., extracted with ethyl acetate and the extract washed with water. The organic layer was separated and the solvent removed under reduced pressure. The residue was chromatographed on silica gel, eluting with dichloromethane/acetone (99/1) to give 16.58 g of 6-cyano-2,2,3-trimethyl-3,4-dihydro-2H-1-benzopyran-4-one, $^1$H NMR (CDCl$_3$): $\delta$1.2 (d, 3H), 1.30 (s, 3H), 1.5 (s, 3H), 2.8 (q, 1H), 7.0 (d, 1H), 7.70 (d, 1H), 8.1 (s, 1H).

PREPARATION 4

Preparation of Compounds of Formula (6)

A. Preparation of Formula (6) where Y is nitro, $R^1$ and $R^2$ are methyl, and $R^5$ and $R^6$ are hydrogen A suspension of 6-nitro-2,2,3-trimethyl-3,4-dihydro-2H-1-benzopyran-4-one (40 g, 0.170 mol) in methanol (400 ml) was treated with sodium borohydride (6.4 g, 0.170 mol) at room temperature. After stirring for two hours the solvent was evaporated under reduced pressure, and the residue treated with a mixture of water and dichloromethane. After stirring the organic phase was separated and evaporated under reduced pressure to give 42.2 g of 6-nitro-2,2,3-trimethyl-4-hydroxy-3,4-dihydro-2H-1-benzopyran, as an oil, $^1$H NMR (CDCl$_3$): $\delta$1.05 (d, 3H), 1.4 (s, 3H), 1.45 (s, 3H), 2.0–2.2 (m, 2H), 4.4 and 4.9 (multiplets cis and trans, 1H), 6.85 (m, 1H), 8.05 (m, 1H), 8.4 (m, 1H).

B. Preparation of Formula (6) where Y is bromo or cyano, $R^1$ and $R^2$ are methyl, and $R^5$ and $R^6$ are hydrogen Similarly, replacing 6-nitro-2,2,3-trimethyl-3,4-dihydro-2H-1-benzopyran-4-one with the 6-cyano analog of Formula (5) or the 6-bromo analog of Formula (3b), and following the procedure of Preparation 4A above, the following compounds of Formula (6) were obtained:
6-cyano-2,2,3-trimethyl-4-hydroxy-3,4-dihydro-2H-1-benzopyran;
6-bromo-2,2,3-trimethyl-4-hydroxy-3,4-dihydro-2H-1-benzopyran, as an oil, $^1$H NMR (CDCl$_3$): δ1.0 (d,3H), 1.3 (s,6H), 2.0 (m,1H), 4.8 (d,1H), 6.7 (d,1H), 7.25 (d,1H), 7.5 (s,1H).

PREPARATION 5

Preparation of Compounds of Formula (7)
A. Preparation of Formula (7) where Y is nitro, $R^1$ and $R^2$ are methyl, and $R^5$ and $R^6$ are hydrogen A solution of 6-nitro-2,2,3-trimethyl-4-hydroxy-3,4-dihydro-2H-1-benzopyran (31.1 g, 0.131 mol) and p-toluenesulfonic acid (2.5 g, 0.013 mol) in toluene (875 ml) was refluxed for 18 hours, removing water with a Dean and Stark water separator. The cooled solution was washed with aqueous sodium bicarbonate solution and the organic phase separated. Solvent was removed under reduced pressure to give 30 g of 6-nitro-2,2,3-trimethyl-2H-1-benzopyran as an oil, $^1$H NMR (CDCl$_3$): δ1.45 (s, 6H), 1.9 (s, 3H), 6.15 (s, 1H), 6.8 (d, 1H), 7.8 (s, 1H), 8.0 (d, 1H).

B. Preparation of Formula (7) where Y is bromo or cyano, $R^1$ and $R^2$ are methyl, and $R^5$ and $R^6$ are hydrogen Similarly, replacing 6-nitro-2,2,3-trimethyl-4-hydroxy-3,4-dihydro-2H-1-benzopyran with the compound of Formula (6) where Y is bromo or cyano, and following the procedure of Preparation 5A above, the following compounds of Formula (7) were prepared:
6-cyano-2,2,3-trimethyl-2H-1-benzopyran, as an oil;
6-bromo-2,2,3-trimethyl-2H-1-benzopyran, as an oil, $^1$H NMR (CDCl$_3$): δ1.4 (s,6H) 1.8 (s,3H), 6.0 (s,1H), 6.6 (d,1H), 7.0 (s,1H), 7.1 (d,1H).

PREPARATION 6

Preparation of Compounds of Formula (b)
Preparation of Formula (b) where $R^1$ and $R^2$ are methyl, and $R^5$ and $R^6$ are hydrogen To 10.5 ml (10.2 g, 0.1 mol) of 3-hydroxy-3-methyl-2-butanone at −5° C. was added dropwise phosphorus tribromide (3.75 ml, 0.04 mol). After one hour of stirring at room temperature, the mixture was cooled and treated with water and diethyl ether. The organics were separated, washed with water, then dried and evaporated to obtain 12.04 g (73%) of crude 3-bromo-3-methyl-2-butanone as an oil, $^1$H NMR (CDCl$_3$): δ1.9 (s,3H), 2.45 (s,3H).

PREPARATION 7

Preparation of Compounds of Formula (d)
Preparation of Formula (d) Where Y is iodo To a solution of 5-iodosalicylic acid (1 g, 0.378 mol) in anhydrous tetrahydrofuran (4 ml) at 0° C. was added dropwise borane-tetrahydrofuran complex (1.0M solution in tetrahydrofuran, 11.4 ml). After fifteen minutes at room temperature, the mixture was heated at reflux for two hours. Water and ethyl acetate were added to the cooled solution, the organic phase separated and evaporated to give crude product. The residue was washed with pentane to afford 0.8 g (84.21%) of 2-hydroxy-5-iodo-benzyl alcohol, m.p. 125° C.

PREPARATION 8

Preparation of Compounds of Formula (e)
A. Preparation of Formula (e) where Y is iodo, $R^1$ and $R^2$ are methyl, and $R^5$ and $R^6$ are hydrogen A mixture containing 2-hydroxy-5-iodobenzyl alcohol (0.63 g, 0.00252 mol), 3-bromo-3-methyl-2-butanone (0.42 g, 0.00254 mol) and potassium carbonate (0.42 g, 0.00377 mol) in methyl ethyl ketone (7 ml) was heated at reflux for three hours. Then a further equivalent of 3-bromo-3-methyl-2-butanone (0.42 g, 0.00254 mol) was added. After heating at reflux for three hours, the cooled mixture was washed successively with water and aqueous sodium hydroxide solution, then extracted with ethyl acetate. The organic layer was evaporated to afford 0.88 g (100%) of crude 3-(2-hydroxymethyl-4-iodophenoxy)-3-methyl-2-butanone.

B. Preparation of Formula (e) where Y is bromo, $R^1$ and $R^2$ are methyl, and $R^5$ and $R^6$ are hydrogen Similarly, replacing 2-hydroxy-5-iodobenzyl alcohol with 2-hydroxy-5-bromobenzyl alcohol, and following the procedure of Preparation 8A above, the following compound of Formula (e) was prepared:
3-(2-hydroxymethyl-4-bromophenoxy)-3-methyl-2-butanone, as an oil, $^1$NMR (CDCl$_3$): δ1.5 (s, 6H), 2.2 (s, 1H), 2.25 (s, 3H), 4.7 (d, 2H), 6.4 (d, 1H), 7.25 (m, 1H), 7.5 (d, 1H).

PREPARATION 9

Preparation of Compounds of Formula (f)
A. Preparation of Formula (f) where Y is iodo, $R^1$ and $R^2$ are methyl, and $R^5$ and $R^6$ are hydrogen A mixture containing crude 3-(2-hydroxymethyl-4-iodophenoxy)-3-methyl-2-butanone (0.84 g, 0.00252 mol) and triphenylphosphine hydrobromide (0.86 g, 0.00252 mol) in acetonitrile (5 ml) was heated at 90° C. for 2.5 hours. After evaporation of the solvent, the crude solid product was washed with ether and dissolved in ethanol (3 ml). Hot isopropyl ether (8 ml) was added until a light precipitate formed, and the solution was left at room temperature overnight. The crystalline product was recovered by filtration to yield 0.77 g (50%) of 2-(1-methyl-2-oxo-propyloxy)-5-iodobenzyltriphenylphosphonium bromide, m.p. 230° C.

B. Preparation of Formula (f) where Y is bromo, $R^1$ and $R^2$ are methyl, and $R^5$ and $R^6$ are hydrogen Similarly, replacing 3-(2-hydroxymethyl-4-iodophenoxy)-3-methyl-2-butanone with 3-(2-hydroxymethyl-4-bromophenoxy)-3-methyl-2-butanone, and following the procedure of Preparation 9A above, the following compound of Formula (f) was prepared:
2-(1-methyl-2-oxo-propyloxy)-5-bromobenzyltriphenylphosphonium bromide, m.p. 240° C.

PREPARATION 10

Alternative Preparation of Compounds of Formula (7)
A. Preparation of Formula (7) where Y is iodo, $R^1$ and $R^2$ are methyl, and $R^5$ and $R^6$ are hydrogen To a suspension of 2-(1-methyl-2-oxo-propyloxy)-5-iodobenzyltriphenylphosphonium bromide (0.71 g, 0.00108 mol) in absolute ethanol (3 ml) was added dropwise at room temperature a solution of sodium (0.025 g) in absolute ethanol (1 ml). After twelve hours at room temperature, diethyl ether and water were added. The organic phase was separated, dried and evaporated. The residue was chromatographed on silica gel, eluting with a mixture of dichloromethane/heptane (50/50) to give 0.29 g (85%) of 6-iodo-2,2,3-trimethyl-1(2H)-benzopyran, as an oil, $^1$NMR (CDCl$_3$): δ1.4 (s, 6H), 1.8 (s, 3H), 6.0 (s, 1H), 6.55 (d, 1H), 7.2 (d, 1H), 7.35 (d, 1H).

B. Preparation of Formula (7) where Y is bromo, R$^1$ and R$^2$ are methyl, and R$^5$ and R$^6$ are hydrogen Similarly, replacing 2-(1-methyl-2-oxo-propyloxy)-5-iodobenzyltriphenylphosphonium bromide with 2-(1-methyl-2-oxo-propyloxy)-5-bromo-benzyltriphenylphosphonium bromide, and following the procedure of Preparation 10A above, the following compound of Formula (7) was prepared:

6-bromo-2,2,3-trimethyl-1(2H) -benzopyran, as an oil, $^1$H NMR (CDCl$_3$): δ1.4 (s,6H), 1.8 (s,3H), 6.0 (s,1H), 6.6 (d,1H), 7.0 (s,1H), 7.1 (d,1H).

PREPARATION 11

Preparation of Compounds of Formula (9)

A. Preparation of Formula (9) where Z is trifluoromethyl, R$^1$ and R$^2$ are methyl, and R$^5$ and R$^6$ are hydrogen A suspension containing 6-bromo-2,2,3-trimethyl-2H-1-benzopyran (38.0 g, 0.15 mol), potassium trifluoroacetate (62.0 g, 0.408 mol) and cuprous iodide (57.0 g, 0.30 mol) in dimethylformamide (530 ml) and toluene (225 ml) was heated under nitrogen until a total of 70 ml of toluene was collected by distillation. Toluene was distilled off until the temperature of the reaction mixture reached 149° C. After a further four hours at this temperature the mixture was cooled to room temperature, water and diethyl ether were added, and the organic phase separated and evaporated under reduced pressure. The residue was chromatographed on silica gel, eluting with heptane to give 18.82 g of 6-trifluoromethyl-2,2,3-trimethyl-2H-1-benzopyran as an oil, ms 242 (M+).

Similarly, replacing 6-bromo-2,2,3-trimethyl-2H-1-benzopyran with 6-iodo-2,2,3-trimethyl-2H-1-benzopyran, and following the same procedure as described in the preceding paragraph, 6-trifluoromethyl-2,2,3-trimethyl-2H-1-benzopyran was obtained in 94% yield.

B. Preparation of Formula (9) where Z is pentafluoroethyl, R$^1$ and R$^2$ are methyl, and R$^5$ and R$^6$ are hydrogen Similarly, replacing potassium trifluoroacetate with potassium pentafluoroacetate, and following the procedure of Preparation 11A above, the following compound of Formula (9) was prepared:

6-pentafluoroethyl-2,2,3-trimethyl-2H-1-benzopyran as an oil, ms 292 (M+).

PREPARATION 12

Preparation of compounds of Formula (10)

A. Preparation of Formula (10) where R$^3$ is nitro, R$^1$ and R$^2$ are methyl, and R$^5$ and R$^6$ are hydrogen To a solution of 6-nitro-2,2,3-trimethyl-2H-1-benzopyran (10.0 g, 0.0457 mol) in dichloromethane (200 ml) at 0° C. was added m-chloroperbenzoic acid (13.5 g, 70%, 0.0548 mol). After stirring for eighteen hours at room temperature the mixture was washed successively with water, aqueous sodium hydrogen carbonate, water and then aqueous sodium hydroxide solution. The organic phase was separated and evaporated under reduced pressure to give 9.96 g (93%) of 6-nitro-2,2,3-trimethyl-3,4-dihydro-3,4-epoxy-2H-1-benzopyran, $^1$H NMR (CDCl$_3$): δ1.3 (s,3H), 1.55 (s,3H), 1.60 (s,3H), 3.8 (s,1H), 6.9 (d,1H), 8.15 (d,1H), 8.30 (s,1H).

B. Preparation of Formula (10) where R$^3$ is cyano or trifluoromethyl, R$^1$ and R$^2$ are methyl, and R$^5$ and R$^6$ are hydrogen Similarly, replacing 6-nitro-2,2,3-trimethyl-2H-1-benzopyran with compounds of Formula (7) or (9), obtained, for example, as shown in Preparations 5 and 11, and following the procedure of Preparation 12A above, the following compounds of Formula (10) were prepared:

6-cyano-2,2,3-trimethyl-3,4-dihydro-3,4-epoxy-2H-1-benzopyran, m.p. 122° C.;

6-trifluoromethyl-2,2,3-trimethyl-3,4-dihydro-3,4-epoxy-2H-1-benzopyran, as an oil, $^1$H NMR (CDCl$_3$): δ1.3 (s,3H), 1.55 (s,3H), 1.6 (s,3H), 3.75 (s,1H), 6.85 (d, 1H), 7.4–7.6 (m,2H); and 6-pentafluoroethyl-2,2,3-trimethyl-3,4-dihydro-3,4-epoxy-2H-1-benzopyran, mp 50° C.

PREPARATION 13

Preparation of Compounds of Formula (12)

A. Preparation of Formula (12) where R$^3$ is nitro, R$^4$ is 2-oxo-1,2-dihydro-pyridin-1-yl, R$^1$ and R$^2$ are methyl, and R$^5$ and R$^6$ are hydrogen A solution of 6-nitro-2,2,3-trimethyl-3,4-dihydro-3,4-epoxy-2H-1-benzopyran (9.93 g, 0.0422 mol), 2(1H)-pyridinone (8.04 g, 0.0845 mol) and Triton B (40% in ethanol, 2.5 ml) in dioxan (100 ml) was heated at reflux for twenty hours. Water and ethyl acetate were added to the cooled solution, the organic phase separated and the solvent removed under reduced pressure. The residue was washed with diethyl ether and pentane, to give 3.53 g of 6-nitro-2,2,3-trimethyl-4-(2-oxo-1,2-dihydropyridin-1-yl)-3,4-dihydro-3-hydroxy-2H-1-benzopyran, m.p. 214° C.

B. Preparation of Formula (12) where R$^3$ is cyano, trifluoromethyl or pentafluoroethyl, R$^4$ is 2-oxo-1,2-dihydropyridin-1-yl, R$^1$ and R$^2$ are methyl, and R$^5$ and R$^6$ are hydrogen Similarly, replacing 6-nitro-2,2,3-trimethyl-3,4-dihydro-3,4-epoxy-2H-1-benzopyran with compounds of Formula (10), obtained, for example, as shown in Preparation 12, and following the procedure of Preparation 13A above, the following compounds of Formula (12) were obtained:

6-cyano-2,2,3-trimethyl-4-(2-oxo-1,2-dihydropyridin-1-yl)-3,4-dihydro-3-hydroxy-2H-1-benzopyran, $^1$H NMR (CDCl$_3$): δ1.10 (s,3H), 1.5 (s,3H), 4.6 (br.s,1H), 6.3 (m,1H), 6.6 (s,1H), 6.8 (d,1H), 7.0 (d,1H), 7.4–7.6 (m,4H);

6-trifluoromethyl-2,2,3-trimethyl-4-(2-oxo-1,2-dihydropyridin-1-yl)-3,4-dihydro-3-hydroxy-2H-1-benzopyran, m.p. 178° C.; and 6-pentafluoroethyl-2,2,3-trimethyl-4-(2-oxo-1,2-dihydropyridin-1-yl)-3,4-dihydro-3-hydroxy-2H-1-benzopyran, as an oil, ms 403 (M+).

C. Preparation of Formula (12) where R$^1$ and R$^2$ are methyl, and R$^5$ and R$^6$ are hydrogen, varying R$^3$ and R$^4$ Similarly, optionally replacing 6-nitro-2,2,3-trimethyl-3,4-dihydro-3,4-epoxy-2H-1-benzopyran with compounds of Formula (10), obtained, for example, as shown in Preparation 12, and replacing 2(1H)-pyridinone (2-oxo-1,2-dihydropyridine) with 2-oxo-pyrrolidine or 1-oxo-isoindoline, and following the procedure of Preparation 13A above, the following compounds of Formula (12) are obtained:

6-nitro-2,2,3-trimethyl-4-(2-oxopyrrolidin-1-yl)-3,4-dihydro-3-hydroxy-2H-1-benzopyran;

6-cyano-2,2,3-trimethyl-4-(2-oxopyrrolidin-1-yl)-3,4-dihydro-3-hydroxy-2H-1-benzopyran;

6-trifluoromethyl-2,2,3-trimethyl-4-(2-oxopyrrolidin-1-yl)-3,4-dihydro-3-hydroxy-2H-1-benzopyran;

6-pentafluoroethyl-2,2,3-trimethyl-4-(2-oxopyrrolidin-1-yl)-3,4-dihydro-3-hydroxy-2H-1-benzopyran;

6-nitro-2,2,3-trimethyl-4-(1-oxoisoindolin-2-yl)-3,4-dihydro-3-hydroxy-2H-1-benzopyran;

6-cyano-2,2,3-trimethyl-4-(1-oxoisoindolin-2-yl)-3,4-dihydro-3-hydroxy-2H-1-benzopyran;

6-trifluoromethyl-2,2,3-trimethyl-4-(1-oxoisoindolin-2-yl)-3,4-dihydro-3-hydroxy-2H-1-benzopyran; and 6-pentafluoroethyl-2,2,3-trimethyl-4-(1-oxoisoindolin-2-yl)-3,4-dihydro-3-hydroxy-2H-1-benzopyran.

PREPARATION 14

Preparation of compounds of Formula (13)

A. preparation of Formula (13) where $R^3$ is nitro, $R^4$ is 2-oxo-1,2-dihydropyridin-1-yl, $R^1$ and $R^2$ are methyl, and $R^5$ and $R^6$ are hydrogen A. A solution of 6-nitro-2,2,3-trimethyl-4-(2-oxo-1,2-dihydropyridin-1-yl)-3,4-dihydro-3-hydroxy-2H-1-benzopyran (3.53 g, 0.0107 mol) in tetrahydrofuran (150 ml) was treated with sodium hydride (80%, 0.32 g). The mixture was heated at reflux for sixteen hours. Water and ethyl acetate were added to the cooled solution and the organic layer separated, dried and evaporated under reduced pressure to afford 1.62 g of 6-nitro-2,2,3-trimethyl-4-(2-oxo-1,2-dihydropyridin-1-yl)-2H-1-benzopyran, m.p. 200° C.

B. Preparation of Formula (13) where $R^3$ is cyano, trifluoromethyl or pentafluoroethyl, $R^4$ is 2-oxo-1,2-dihydropyridin-1-yl, $R^1$ and $R^2$ are methyl, and $R^5$ and $R^6$ are hydrogen Similarly, replacing 6-nitro-2,2,3-trimethyl-4-(2-oxo-1,2-dihydropyridin-1-yl)-3,4,dihydro-3-hydroxy-2H-1-benzopyran with other compounds of Formula (12), obtained, for example, as shown in Preparation 13, and following the procedure of Preparation 14A above, the following compounds of Formula (13) were obtained:

6-cyano-2,2,3-trimethyl-4-(2-oxo-1,2-dihydropyridin-1-yl)-2H-1-benzopyran, m.p. 213° C.;

6-trifluoromethyl-2,2,3-trimethyl-4-(2-oxo-1,2-dihydropyridin-1-yl)-2H-1-benzopyran, m.p. 130° C.; and 6-pentafluoroethyl-2,2,3-trimethyl-4-(2-oxo-1,2-dihydropyridin-1-yl)-2H-1-benzopyran, m.p. 125° C.

C. Preparation of Formula (13) where $R^1$ and $R^2$ are methyl, and $R^5$ and $R^6$ are hydrogen, varying $R^3$ and $R^4$ Similarly, optionally replacing 6-nitro-2,2,3-trimethyl-3,4-dihydro-3,4-epoxy-2H-1-benzopyran with other compounds of Formula (12), obtained, for example, as shown in Preparation 13, and replacing 2(1H)-pyridinone (2-oxo-1,2-dihydropyridine) with 2-oxo-pyrrolidine or 1-oxo-isoindoline, and following the procedure of Preparation 14A above, the following compounds of Formula (13) are obtained:

6-nitro-2,2,3-trimethyl-4-(2-oxopyrrolidin-1-yl)-2H-1-benzopyran;

6-cyano-2,2,3-trimethyl-4-(2-oxopyrrolidin-1-yl)-2H-1-benzopyran;

6-trifluoromethyl-2,2,3-trimethyl-4-(2-oxopyrrolidin-1-yl)-2H-1-benzopyran;

6-pentafluoroethyl-2,2,3-trimethyl-4-(2-oxopyrrolidin-1-yl)-2H-1-benzopyran;

6-nitro-2,2,3-trimethyl-4-(1-oxoisoindolin-2-yl)-2H-1-benzopyran;

6-cyano-2,2,3-trimethyl-4-(1-oxoisoindolin-2-yl)-2H-1-benzopyran;

6-trifluoromethyl-2,2,3-trimethyl-4-(1-oxoisoindolin-2-yl)-2H-1-benzopyran; and 6-pentafluoroethyl-2,2,3-trimethyl-4-(1-oxoisoindolin-2-yl)-2H-1-benzopyran.

PREPARATION 15

Preparation of Compounds of Formula (14)

A. Preparation of Formula (14) where $R^3$ is nitro, $R^4$ is 2-oxo-1,2-dihydropyridin-1-yl, $R^1$ and $R^2$ are methyl, and $R^5$ and $R^6$ are hydrogen A suspension of 6-nitro-2,2,3-trimethyl-4-(2-oxo-1,2-dihydropyridin-1-yl)-2H-1-benzopyran (1.62 g, 0.0052 mol) in carbon tetrachloride (10 ml) containing benzoyl peroxide (20 mg) was heated to 60° C. N-bromosuccinimide (0.92 g, 0.0052 mol) was added and the mixture heated at reflux for seventeen hours. The cooled solution was treated with dichloromethane and aqueous ferrous sulfate solution, the organic phase was separated and evaporated under reduced pressure. The residue was chromatographed on silica gel, eluting with dichloromethane/acetone (92.5/7.5). The product was washed with diethyl ether/pentane to give 1.49 g of 6-nitro-2,2-dimethyl-3-bromomethyl-4-(2-oxo-1,2-dihydropyridin-1-yl)-2H-1-benzopyran, m.p. 221° C.

B. Preparation of Formula (14) where $R^3$ is cyano, trifluoromethyl or pentafluoroethyl, $R^4$ is 2-oxo-1,2-dihydropyridin-1-yl, $R^1$ and $R^2$ are methyl, and $R^5$ and $R^6$ are hydrogen Similarly, replacing 6-nitro-2,2,3-trimethyl-4-(2-oxo-1,2-dihydropyridin-1-yl)-2H-1-benzopyran with other compounds of Formula (13), obtained, for example, as shown in Preparation 14, and following the procedure of Preparation 15A above, the following compounds of Formula (13) were obtained:

6-cyano-2,2-dimethyl-3-bromomethyl-4-(2-oxo-1,2-dihydropyridin-1-yl)-2H-1-benzopyran; m.p. 180° C.;

6-trifluoromethyl-2,2-dimethyl-3-bromomethyl-4-(2-oxo-1,2-dihydropyridin-1-yl)-2H-1-benzopyran, m.p. 130° C.; and 6-pentafluoroethyl-2,2-dimethyl-3-bromomethyl-4-(2-oxo-1,2-dihydropyridin-1-yl)-2H-1-benzopyran, m.p. 112° C.

C. Preparation of Formula (14) where $R^1$ and $R^2$ are methyl, and $R^5$ and $R^6$ are hydrogen, varying $R^3$ and $R^4$ Similarly, optionally replacing 6-nitro-2,2,3-trimethyl-3,4-dihydro-3,4-epoxy-2H-1-benzopyran with other compounds of Formula (13), obtained, for example, as shown in Preparation 14, and replacing 2(1H)-pyridinone (2-oxo-1,2-dihydropyridine) with 2-oxo-pyrrolidine or 1-oxo-isoindoline, and following the procedure of Preparation 15A above, the following compounds of Formula (14) are obtained:

6-nitro-2,2-dimethyl-3-bromomethyl-4-(2-oxopyrrolidin-1-yl)-2H-1-benzopyran;

6-cyano-2,2-dimethyl-3-bromomethyl-4-(2-oxopyrrolidin-1-yl)-2H-1-benzopyran;

6-trifluoromethyl-2,2-dimethyl-3-bromomethyl-4-(2-oxopyrrolidin-1-yl)-2H-1-benzopyran;

6-pentafluoroethyl-2,2-dimethyl-3-bromomethyl-4-(2-oxopyrrolidin-1-yl)-2H-1-benzopyran;

6-nitro-2,2-dimethyl-3-bromomethyl-4-(1-oxoisoindolin-2-yl)-2H-1-benzopyran;

6-cyano-2,2-dimethyl-3-bromomethyl-4-(1-oxoisoindolin-2-yl)-2H-1-benzopyran;

6-trifluoromethyl-2,2-dimethyl-3-bromomethyl-4-(1-oxoisoindolin-2-yl)-2H-1-benzopyran; and 6-pentafluoroethyl-2,2-dimethyl-3-bromomethyl-4-(1-oxoisoindolin-2-yl)-2H-1-benzopyran.

PREPARATION 16

Alternative preparation of Compounds of Formula (14)

A. Preparation of Formula (14) where $R^3$ is bromo, $R^1$ and $R^2$ are methyl, $R^5$ and $R^6$ are hydrogen and $R^4$ is 2-oxo-1,2-dihydropyridin-1-yl 6-bromo-2,2-dimethyl-3-hydroxymethyl-4-(2-oxo-1,2-dihydropyridin-1-yl)-2H-1-benzopyran (9.0 g, 0.0248 mol) was suspended in toluene (150 ml). Phosphorus tribromide (0.94 ml, 2.69 g, 0.0099 mol) was added and the mixture heated at reflux for two hours. The cooled solution was treated with water and ethyl acetate, the organic phase separated and washed three times with aqueous sodium chloride solution, and then dried and evaporated under reduced pressure. The residue was triturated with pentane and dried to afford 9.94 g of 6-bromo-2,2-dimethyl-3-bromomethyl-4-(2-oxo-1,2-dihydropyridin-1-yl)-2H-1-benzopyran, m.p. 175° C.

B. Preparation of Formula (14) where $R^3$ is chloro or hydrogen, $R^1$ and $R^2$ are methyl, $R^5$ and $R^6$ are hydrogen and $R^4$ is 2-oxo-1,2-dihydropyridin-1-yl Similarly, replacing 6-bromo-2,2-dimethyl-3-hydroxymethyl-4-(2-oxo-1,2-dihydropyridin-1-yl)-2H-1-benzopyran with other compounds of Formula (26), and following the procedure of Preparation 16A above, the following compounds of Formula (14) were obtained:

6-chloro-2,2-dimethyl-3-bromomethyl-4-(2-oxo-1,2-dihydropyridin-1-yl)-2H-1-benzopyran, m.p. 164° C.; and 2,2-dimethyl-3-bromomethyl-4-(2-oxo-1,2-dihydropyridin-1-yl)-2H-1-benzopyran, m.p. 160° C.

PREPARATION 17

Preparation of Compounds of Formula (15)

A. Preparation of Formula (15) where $R^3$ is nitro, $R^4$ is 2-oxo-1,2-dihydropyridin-1-yl, $R^1$ and $R^2$ are methyl, and $R^5$ and $R^6$ are hydrogen A solution of 6-nitro-2,2-dimethyl-3-bromomethyl-4-(2-oxo-1,2-dihydropyridin-1-yl)-2H-1-benzopyran (0.1 g, 0.255 mmol) in ethanol (2 ml) containing concentrated aqueous ammonium hydroxide solution (2 ml) was stirred at room temperature for four hours. The solvent was evaporated and the residue treated with ethanolic hydrochloric acid (2 ml) with heating. Crystallization was induced by addition of diethyl ether, giving 0.07 g of 6-nitro-2,2-dimethyl-3-aminomethyl-4-(2-oxo-1,2-dihydropyridin-1-yl)-2H-1-benzopyran as a hydrochloride salt, m.p. 231° C.

B. Preparation of Formula (15) where $R^3$ is cyano, trifluoromethyl or pentafluoroethyl, $R^4$ is 2-oxo-1,2-dihydropyridin-1-yl, $R^1$ and $R^2$ are methyl, and $R^5$ and $R^6$ are hydrogen Similarly, replacing 6-nitro-2,2-dimethyl-3-bromomethyl-4-(2-oxo-1,2-dihydropyridin-1-yl)-2H-1-benzopyran with other compounds of Formula (14), obtained, for example, as shown in Preparation 15, and following the procedure of Preparation 17A above, the following compounds of Formula (14) were obtained:

6-cyano-2,2-dimethyl-3-aminomethyl-4-(2-oxo-1,2-dihydropyridin-1-yl)-2H-1-benzopyran, m.p. 175° C.;

6-trifluoromethyl-2,2-dimethyl-3-aminomethyl-4-(2-oxo-1,2-dihydropyridin-1-yl)-2H-1-benzopyran, m.p. 128° C.; and 6-pentafluoroethyl-2,2-dimethyl-3-aminomethyl-4-(2-oxo-1,2-dihydropyridin-1-yl)-2H-1-benzopyran, m.p. 128° C.

C. Preparation of Formula (15) where $R^1$ and $R^2$ are methyl, and $R^5$ and $R^6$ are hydrogen, varying $R^3$ and $R^4$ Similarly, optionally replacing 6-nitro-2,2-dimethyl-3-bromomethyl-4-(2-oxo-1,2-dihydropyridin-1-yl)-2H-1-benzopyran with other compounds of Formula (14), obtained, for example, as shown in Preparation 15, and replacing 2(1H)-pyridinone (2-oxo-1,2-dihydropyridine) with 2-oxo-pyrrolidine or 1-oxoisoindoline, and following the procedure of Preparation 17A above, the following compounds of Formula (15) are obtained:

6-nitro-2,2-dimethyl-3-aminomethyl-4-(2-oxopyrrolidin-1-yl)-2H-1-benzopyran;

6-cyano-2,2-dimethyl-3-aminomethyl-4-(2-oxopyrrolidin-1-yl)-2H-1-benzopyran;

6-trifluoromethyl-2,2-dimethyl-3-aminomethyl-4-(2-oxopyrrolidin-1-yl)-2H-1-benzopyran;

6-pentafluoroethyl-2,2-dimethyl-3-aminomethyl-4-(2-oxopyrrolidin-1-yl)-2H-1-benzopyran;

6-nitro-2,2-dimethyl-3-aminomethyl-4-(1-oxoisoindolin-2-yl)-2H-1-benzopyran;

6-cyano-2,2-dimethyl-3-aminomethyl-4-(1-oxoisoindolin-2-yl)-2H-1-benzopyran;

6-trifluoromethyl-2,2-dimethyl-3-aminomethyl-4-(1-oxoisoindolin-2-yl)-2H-1-benzopyran; and 6-pentafluoroethyl-2,2-dimethyl-3-aminomethyl-4-(1-oxoisoindolin-2-yl)-2H-1-benzopyran.

PREPARATION 18

Preparation of Compounds of Formula (16)

A. Preparation of Formula (16) where $R^3$ is nitro, $R^1$ and $R^2$ are methyl, and $R^5$ and $R^6$ are hydrogen A solution of 6-nitro-2,2,3-trimethyl-2H-1-benzopyran (33.0 g, 0.151 mol) and benzoyl peroxide (0.020 g) in carbon tetrachloride (330 ml) were heated to 50° C. and N-bromo succinimide (26.8 g, 0.15 mol) was added. The mixture was heated at reflux for eighteen hours and then water and aqueous ferrous sulfate were added. The organic phase was separated and evaporated under reduced pressure, and the residue washed with pentane to give 40.45 g of 6-nitro-2,2-dimethyl-3-bromomethyl-2H-1-benzopyran, m.p. 107° C.

B. Preparation of Formula (16) where $R^3$ is cyano, trifluoromethyl or pentafluoroethyl, $R^1$ and $R^2$ are methyl, and $R^5$ and $R^6$ are hydrogen Similarly, replacing 6-nitro-2,2,3-trimethyl-2H-1-benzopyran with compounds of Formula (7) or (9), obtained, for example, as shown in Preparations 5 and 11, and following the procedure of Preparation 18A above, the following compounds of Formula (16) are prepared:

6-cyano-2,2-dimethyl-3-bromomethyl-2H-1-benzopyran;

6-trifluoromethyl-2,2-dimethyl-3-bromomethyl-2H-1-benzopyran; and 6-pentafluoroethyl-2,2-dimethyl-3-bromomethyl-2H-1-benzopyran.

PREPARATION 19

Preparation of Compounds of Formula (17)

A. Preparation of Formula (17) where $R^3$ is nitro, $R^1$ and $R^2$ are methyl, $R^5$ and $R^6$ are hydrogen, and $R^7$ is trifluoroacetamido 2,2,2-trifluoroacetamide (0.53 g, 4.7 mmol) in dimethylformamide (2 ml) was added dropwise to a suspension of sodium hydride (80%, 1.4 g, 4.7 mmol) in dimethylformamide (2 ml). After one hour at room temperature 6-nitro-2,2-dimethyl-3-bromomethyl-2H-1-benzopyran (1.4 g, 4.7 mmol) was added and the mixture heated at 70° C. for eighteen hours. Water and ethyl acetate were added to the cooled solution and the organic phase separated and evaporated to give 0.51 g of 6-nitro-2,2-dimethyl-3-(trifluoroacetamido)methyl-2H-1-benzopyran, $^1$NMR (CDCl$_3$): δ1.5 (s, 6H), 4.15 (d, 2H), 6.25 (s, 1H), 6.85 (d, 1H), 6.9 (br.s), 1H), 7.85 (s, 1H), 8.05 (d, 1H).

B. Preparation of Formula (17) where R$^1$ and R$^2$ are methyl, R$^5$ and R$^6$ are hydrogen, and R$^7$ is trifluoroacetamido, varying R$^3$ Similarly, replacing 6-nitro-2,2-dimethyl-3-bromomethyl-2H-1-benzopyran with an appropriate compound of Formula (16), obtained, for example, as shown in Preparation 18, and following the procedure of Preparation 19A above, the following compounds of Formula (17) are prepared:
6-cyano-2,2-dimethyl-3-(trifluoroacetamido)methyl-2H-1-benzopyran;
6-trifluoromethyl-2,2-dimethyl-3-(trifluoroacetamido)methyl-2H-1-benzopyran; and
6-pentafluoroethyl-2,2-dimethyl-3-(trifluoroacetamido)methyl-2H-1-benzopyran.

PREPARATION 20

Preparation of Compounds of Formula (18)
A. Preparation of Formula (18) where R$^3$ is nitro, R$^1$ and R$^2$ are methyl, R$^5$ and R$^6$ are hydrogen, and R$^7$ is trifluoroacetamido A solution of 6-nitro-2,2-dimethyl-3-(trifluoroacetamido)methyl-2H-1-benzopyran (0.5 g, 1.52 mmol) in dichloromethane (10 ml) at 0° C. was treated with m-chloroperbenzoic acid (70%, 0.45 g, 1.52 mmol). After stirring for sixteen hours at room temperature, water and sodium hydrogen carbonate were added and the organic phase separated and evaporated under reduced pressure. The residue was chromatographed on silica gel, eluting with dichloromethane/acetone (95/5), to give 0.43 g of 6-nitro-2,2-dimethyl-3-(trifluoroacetamido)methyl-3,4-dihydro-3,4-epoxy-2H-1-benzopyran $^1$NMR (CDCl$_3$): δ1.4 (s, 3H), 1.6 (s, 3H), 3.7 (dd,1H), 3.85 (s, 1H), 4.15 (dd, 1H), 6.70 (br.s, 1H), 6.95 (d, 1H), 8.2 (d, 1H), 8.30 (s, 1H).

B. Preparation of Formula (18) where R$^1$ and R$^2$ are methyl, R$^5$ and R$^6$ are hydrogen, and R$^7$ is trifluoroacetamido, varying R$^3$ B. Similarly, replacing 6-nitro-2,2-dimethyl-3-(trifluoroacetamido)methyl-2H-1-benzopyran with an appropriate compound of Formula (17), obtained, for example, as shown in Preparation 19, and following the procedure of Preparation 20A above, the following compounds of Formula (18) are prepared:
6-cyano-2,2-dimethyl-3-(trifluoroacetamido)methyl-3,4-dihydro-3,4-epoxy-2H-1-benzopyran;
6-trifluoromethyl-2,2-dimethyl-3-(trifluoroacetamido)methyl-3,4-dihydro-3,4-epoxy-2H-1-benzopyran; and
6-pentafluoroethyl-2,2-dimethyl-3-(trifluoroacetamido)methyl-3,4-dihydro-3,4-epoxy-2H-1-benzopyran.

PREPARATION 21

Preparation of Compounds of Formula (19)
A. Preparation of Formula (19) where R$^3$ is nitro, R$^1$ and R$^2$ are methyl, R$^5$ and R$^6$ are hydrogen, R$^4$ is 2-oxo-1,2-dihydropyridin-1-yl, and R$^7$ is trifluoroacetamido A mixture of 6-nitro-2,2-dimethyl-3-(trifluoroacetamido)methyl-3,4-dihydro-3,4-epoxy-2H-1-benzopyran (0.4 g, 1.16 mmol), 2(1H)-pyridinone (0.22 g, 2.32 mmol) and Triton B (0.05 ml) in dioxane (3 ml) was heated at reflux for nineteen hours. Water and ethyl acetate were added, and the organic phase separated and evaporated under reduced pressure. The residue was chromatographed on silica gel, eluting with dichloromethane/acetone (95/5), to give 0.1 g of 6-nitro-2,2-dimethyl-3-(trifluoroacetamido)methyl-3,4-dihydro-3-hydroxy-4-(2-oxo-1,2-dihydropyridin-1-yl)-2H-1-benzopyran, m.p. 158° C.

B. Preparation of Formula (19) where R$^1$ and R$^2$ are methyl, R$^5$ and R$^6$ are hydrogen, R$^4$ is 2-oxo-1,2-dihydropyridin-1-yl, and R$^7$ is trifluoroacetamido, varying R$^3$ Similarly, replacing 6-nitro-2,2-dimethyl-3-(trifluoroacetamido)methyl-3,4-dihydro-3,4-epoxy-2H-1-benzopyran with an appropriate compound of Formula (18), obtained, for example, as shown in Preparation 20, and following the procedure of Preparation 21A above, the following compounds of Formula (19) are prepared:
6-cyano-2,2-dimethyl-3-(trifluoroacetamido)methyl-3,4-dihydro-3-hydroxy-4-(2-oxo-1,2-dihydropyridin-1-yl)-2H-1-benzopyran;
6-trifluoromethyl-2,2-dimethyl-3-(trifluoroacetamido)methyl-3,4-dihydro-3-hydroxy-4-(2-oxo-1,2-dihydropyridin-1-yl)-2H-1-benzopyran; and
6-pentafluoroethyl-2,2-dimethyl-3-(trifluoroacetamido)methyl-3,4-dihydro-3-hydroxy-4-(2-oxo-1,2-dihydropyridin-1-yl)-2H-1-benzopyran.

EXAMPLE 1

Preparation of Compounds of Formula (I) and (IA) wherein R$^8$ is Lower Alkyl or Hydroxy Lower Alkyl and R$^9$ is Hydrogen, Lower Alkyl or Hydroxy Lower Alkyl A. Preparation of Formula (IA) where R$^3$ is nitro, R$^1$ and R$^2$ are methyl, R$^5$ and R$^6$ are hydrogen, R$^4$ is 2-oxo-1,2-dihydropyridin-1-yl, R$^8$ is methyl and R$^9$ is hydrogen A solution of 6-nitro-2,2-dimethyl-3-bromomethyl-4-(2-oxo-1,2-dihydropyridin-1-yl)-2H-1-benzopyran (0.5 g, 1.27 mmol) and methylamine (40% in water, 1.1 ml, 1.397 mmol) in methanol (12 ml) was stirred at room temperature during four hours. The solvents were evaporated under reduced pressure, and water and ethyl acetate added to the residue. After stirring, the organic phase was separated and evaporated under reduced pressure. The residue was dissolved in diethyl ether and precipitated with pentane, to give 0.31 g of 6-nitro-2,2-dimethyl-3-(methylamino)methyl-4-(2-oxo-1,2-dihydropyridin-1-yl)-2H-1-benzopyran, m.p. 128° C.

B. Preparation of Formula (I) where R$^3$ is nitro, R$^1$ and R$^2$ are methyl, R$^5$ and R$^6$ are hydrogen, R$^4$ is 2-oxo-1,2-dihydropyridin-1-yl, varying R$^8$ and R$^9$ Similarly, replacing methylamine with dimethylamine and 2-hydroxyethylamine respectively, and following the procedure of Example 1A above, the following compounds of Formula (I) were prepared:
6-nitro-2,2-dimethyl-3-(dimethylamino)methyl-4-(2-oxo-1,2-dihydropyridin-1-yl)-2H-1-benzopyran, m.p. 222° C.; and
6-nitro-2,2-dimethyl-3-(2-hydroxyethylamino)methyl-4-(2-oxo-1,2-dihydropyridin-1-yl)-2H-1-benzopyran, m.p. 225° C.

C. preparation of Formula (I) where R$^1$ and R$^2$ are methyl, R$^5$ and R$^6$ are hydrogen, varying R$^3$, R$^4$, R$^8$ and R$^9$ Similarly, optionally replacing 6-nitro-2,2-dimethyl-3-bromomethyl-4-(2-oxo-1,2-dihydropyridin-1-yl)-2H-1-benzopyran with an appropriate compound of Formula (14) prepared, for example, as shown in Preparation 15, and optionally replacing methylamine with an amine of formula HNR$^8$R$^9$, where R$^8$ is lower alkyl or hydroxy lower alkyl and R$^9$ is hydrogen, lower alkyl or hydroxy lower alkyl, and following the procedure of Example 1A above, the following compounds of Formula (I) where R$^8$ is lower alkyl or hydroxy lower alkyl and R$^9$ is hydrogen, lower alkyl or hydroxy lower alkyl are prepared:

6-nitro-2,2-dimethyl-3-(ethylamino)methyl-4-(2-oxo-1,2-dihydropyridin-1-yl)-2H-1-benzopyran;
6-nitro-2,2-dimethyl-3-(diethylamino)methyl-4-(2-oxo-1,2-dihydropyridin-1-yl)-2H-1-benzopyran;
6-nitro-2,2-dimethyl-3-(N-methyl-N-(2-hydroxyethyl)amino)methyl-4-(2-oxo-1,2-dihydropyridin-1-yl)-2H-1-benzopyran;
6-cyano-2,2-dimethyl-3-(methylamino)methyl-4-(2-oxo-1,2-dihydropyridin-1-yl)-2H-1-benzopyran;
6-cyano-2,2-dimethyl-3-(dimethylamino)methyl-4-(2-oxo-1,2-dihydropyridin-1-yl)-2H-1-benzopyran;
6-cyano-2,2-dimethyl-3-(2-hydroxyethylamino)methyl-4-(2-oxo-1,2-dihydropyridin-1-yl)-2H-1-benzopyran;
6-cyano-2,2-dimethyl-3-(ethylamino)methyl-4-(2-oxo-1,2-dihydropyridin-1-yl)-2H-1-benzopyran;
6-cyano-2,2-dimethyl-3-(diethylamino)methyl-4-(2-oxo-1,2-dihydropyridin-1-yl)-2H-1-benzopyran;
6-cyano-2,2-dimethyl-3-(N-methyl-N-(2-hydroxyethyl)amino)methyl-4-(2-oxo-1,2-dihydropyridin-1-yl)-2H-1-benzopyran;
6-trifluoromethyl-2,2-dimethyl-3-(methylamino)methyl-4-(2-oxo-1,2-dihydropyridin-1-yl)-2H-1-benzopyran;
6-trifluoromethyl-2,2-dimethyl-3-(dimethylamino)methyl-4-(2-oxo-1,2-dihydropyridin-1-yl)-2H-1-benzopyran;
6-trifluoromethyl-2,2-dimethyl-3-(2-hydroxyethylamino)methyl-4-(2-oxo-1,2-dihydropyridin-1-yl)-2H-1-benzopyran;
6-trifluoromethyl-2,2-dimethyl-3-(ethylamino)methyl-4-(2-oxo-1,2-dihydropyridin-1-yl)-2H-1-benzopyran;
6-trifluoromethyl-2,2-dimethyl-3-(diethylamino)methyl-4-(2-oxo-1,2-dihydropyridin-1-yl)-2H-1-benzopyran;
6-trifluoromethyl-2,2-dimethyl-3-(N-methyl-N-(2-hydroxyethyl)amino)methyl-4-(2-oxo-1,2-dihydropyridin-1-yl)-2H-1-benzopyran;
6-pentafluoroethyl-2,2-dimethyl-3-(methylamino)methyl-4-(2-oxo-1,2-dihydropyridin-1-yl)-2H-1-benzopyran;
6-pentafluoroethyl-2,2-dimethyl-3-(dimethylamino)methyl-4-(2-oxo-1,2-dihydropyridin-1-yl)-2H-1-benzopyran;
6-pentafluoroethyl-2,2-dimethyl-3-(2-hydroxyethylamino)methyl-4-(2-oxo-1,2-dihydropyridin-1-yl)-2H-1-benzopyran;
6-pentafluoroethyl-2,2-dimethyl-3-(ethylamino)methyl-4-(2-oxo-1,2-dihydropyridin-1-yl)-2H-1-benzopyran;
6-pentafluoroethyl-2,2-dimethyl-3-(diethylamino)methyl-4-(2-oxo-1,2-dihydropyridin-1-yl)-2H-1-benzopyran;
6-pentafluoroethyl-2,2-dimethyl-3-(N-methyl-N-(2-hydroxyethyl)amino)methyl-4-(2-oxo-1,2-dihydropyridin-1-yl)-2H-1-benzopyran;
6-nitro-2,2-dimethyl-3-(methylamino)methyl-4-(2-oxopyrrolidin-1-yl)-2H-1-benzopyran;
6-nitro-2,2-dimethyl-3-(dimethylamino)methyl-4-(2-oxopyrrolidin-1-yl)-2H-1-benzopyran;
6-nitro-2,2-dimethyl-3-(2-hydroxyethylamino)methyl-4-(2-oxopyrrolidin-1-yl)-2H-1-benzopyran;
6-nitro-2,2-dimethyl-3-(ethylamino)methyl-4-(2-oxopyrrolidin-1-yl)-2H-1-benzopyran;
6-nitro-2,2-dimethyl-3-(diethylamino)methyl-4-(2-oxopyrrolidin-1-yl)-2H-1-benzopyran;
6-nitro-2,2-dimethyl-3-(N-methyl-N-(2-hydroxyethyl)amino)methyl-4-(2-oxopyrrolidin-1-yl)-2H-1-benzopyran;
6-cyano-2,2-dimethyl-3-(methylamino)methyl-4-(2-oxopyrrolidin-1-yl)-2H-1-benzopyran;
6-cyano-2,2-dimethyl-3-(dimethylamino)methyl-4-(2-oxopyrrolidin-1-yl)-2H-1-benzopyran;
6-cyano-2,2-dimethyl-3-(2-hydroxyethylamino)methyl-4-(2-oxopyrrolidin-1-yl)-2H-1-benzopyran;
6-cyano-2,2-dimethyl-3-(ethylamino)methyl-4-(2-oxopyrrolidin-1-yl)-2H-1-benzopyran;
6-cyano-2,2-dimethyl-3-(diethylamino)methyl-4-(2-oxopyrrolidin-1-yl)-2H-1-benzopyran;
6-cyano-2,2-dimethyl-3-(N-methyl-N-(2-hydroxyethyl)amino)methyl-4-(2-oxopyrrolidin-1-yl)-2H-1-benzopyran;
6-trifluoromethyl-2,2-dimethyl-3-(methylamino)methyl-4-(2-oxo-pyrrolidin-1-yl)-2H-1-benzopyran;
6-trifluoromethyl-2,2-dimethyl-3-(dimethylamino)methyl-4-(2-oxopyrrolidin-1-yl)-2H-1-benzopyran;
6-trifluoromethyl-2,2-dimethyl-3-(2-hydroxyethylamino)methyl-4-(2-oxopyrrolidin-1-yl)-2H-1-benzopyran;
6-trifluoromethyl-2,2-dimethyl-3-(ethylamino)methyl-4-(2-oxopyrrolidin-1-yl)-2H-1-benzopyran;
6-trifluoromethyl-2,2-dimethyl-3-(diethylamino)methyl-4-(2-oxopyrrolidin-1-yl)-2H-1-benzopyran;
6-trifluoromethyl-2,2-dimethyl-3-(N-methyl-N-(2-hydroxyethyl)amino)methyl-4-(2-oxopyrrolidin-1-yl)-2H-1-benzopyran;
6-pentafluoroethyl-2,2-dimethyl-3-(methylamino)methyl-4-(2-oxopyrrolidin-1-yl)-2H-1-benzopyran;
6-pentafluoroethyl-2,2-dimethyl-3-(dimethylamino)methyl-4-(2-oxopyrrolidin-1-yl)-2H-1-benzopyran;
6-pentafluoroethyl-2,2-dimethyl-3-(2-hydroxyethylamino)methyl-4-(2-oxopyrrolidin-1-yl)-2H-1-benzopyran;
6-pentafluoroethyl-2,2-dimethyl-3-(ethylamino)methyl-4-(2-oxopyrrolidin-1-yl)-2H-1-benzopyran;
6-pentafluoroethyl-2,2-dimethyl-3-(diethylamino)methyl-4-(2-oxopyrrolidin-1-yl)-2H-1-benzopyran;
6-pentafluoroethyl-2,2-dimethyl-3-(N-methyl-N-(2-hydroxyethyl)amino)methyl-4-(2-oxopyrrolidin-1-yl)-2H-1-benzopyran;
6-nitro-2,2-dimethyl-3-(methylamino)methyl-4-(1-oxoisoindolin-2-yl)-2H-1-benzopyran;
6-nitro-2,2-dimethyl-3-(dimethylamino)methyl-4-(1-oxoisoindolin-2-yl)-2H-1-benzopyran;
6-nitro-2,2-dimethyl-3-(2-hydroxyethylamino)methyl-4-(1-oxo-isoindolin-2-yl)-2H-1-benzopyran;
6-nitro-2,2-dimethyl-3-(ethylamino)methyl-4-(1-oxoisoindolin-2-yl)-2H-1-benzopyran;
6-nitro-2,2-dimethyl-3-(diethylamino)methyl-4-(1-oxoisoindolin-2-yl)-2H-1-benzopyran;
6-nitro-2,2-dimethyl-3-(N-methyl-N-(2-hydroxyethyl)amino)methyl-4-(1-oxo-isoindolin-2-yl)-2H-1-benzopyran;
6-cyano-2,2-dimethyl-3-(methylamino)methyl-4-(1-oxoisoindolin-2-yl)-2H-1-benzopyran;
6-cyano-2,2-dimethyl-3-(dimethylamino)methyl-4-(1-oxoisoindolin-2-yl)-2H-1-benzopyran;
6-cyano-2,2-dimethyl-3-(2-hydroxyethylamino)methyl-4-(1-oxo-isoindolin-2-yl)-2H-1-benzopyran;

6-cyano-2,2-dimethyl-3-(ethylamino)methyl-4-(1-oxoisoindolin-2-yl)-2H-1-benzopyran;

6-cyano-2,2-dimethyl-3-(diethylamino)methyl-4-(1-oxoisoindolin-2-yl)-2H-1-benzopyran;

6-cyano-2,2-dimethyl-3-(N-methyl-N-(2-hydroxyethyl)amino)methyl-4-(1-oxo-isoindolin-2-yl)-2H-1-benzopyran;

6-trifluoromethyl-2,2-dimethyl-3-(methylamino)methyl-4-(1-oxo-isoindolin-2-yl)-2H-1-benzopyran;

6-trifluoromethyl-2,2-dimethyl-3-(dimethylamino)methyl-4-(1-oxo-isoindolin-2-yl)-2H-1-benzopyran;

6-trifluoromethyl-2,2-dimethyl-3-(2-hydroxyethylamino)methyl-4-(1-oxo-isoindolin-2-yl)-2H-1-benzopyran;

6-trifluoromethyl-2,2-dimethyl-3-(ethylamino)methyl-4-(1-oxo-isoindolin-2-yl)-2H-1-benzopyran;

6-trifluoromethyl-2,2-dimethyl-3-(diethylamino)methyl-4-(1-oxo-isoindolin-2-yl)-2H-1-benzopyran;

6-trifluoromethyl-2,2-dimethyl-3-(N-methyl-N-(2-hydroxyethyl)amino)methyl-4-(1-oxo-isoindolin-2-yl)-2H-1-benzopyran;

6-pentafluoroethyl-2,2-dimethyl-3-(methylamino)methyl-4-(1-oxo-isoindolin-2-yl)-2H-1-benzopyran;

6-pentafluoroethyl-2,2-dimethyl-3-(dimethylamino)methyl-4-(1-oxo-isoindolin-2-yl)-2H-1-benzopyran;

6-pentafluoroethyl-2,2-dimethyl-3-(2-hydroxyethylamino)methyl-4-(1-oxo-isoindolin-2-yl)-2H-1-benzopyran;

6-pentafluoroethyl-2,2-dimethyl-3-(ethylamino)methyl-4-(1-oxo-isoindolin-2-yl)-2H-1-benzopyran;

6-pentafluoroethyl-2,2-dimethyl-3-(diethylamino)methyl-4-(1-oxo-isoindolin-2-yl)-2H-1-benzopyran; and 6-pentafluoroethyl-2,2-dimethyl-3-(N-methyl-N-(2-hydroxyethyl)amino)methyl-4-(1-oxo-isoindolin-2-yl)-2H-1-benzopyran.

EXAMPLE 2

Preparation of Compounds of Formula (I) and (IA) wherein $R^8$ is Hydroxy or Lower Alkoxy and $R^9$ is Hydrogen or Lower Alkyl A. Preparation of Formula (I) where $R^3$ is nitro, $R^1$ and $R^2$ are methyl, $R^5$ and $R^6$ are hydrogen, $R^4$ is 2-oxo-1,2-dihydropyridin-1-yl, $R^8$ is hydroxy and $R^9$ is methyl A mixture of 6-nitro-2,2-dimethyl-3-bromomethyl-4-(2-oxo-1,2-dihydropyridin-1-yl)-2H-1-benzopyran (0.30 g, 7.7 mmol), N-methylhydroxylamine hydrochloride (0.64 g, 7.7 mmol) and potassium carbonate (0.97 g, 7.7 mmol) in ethanol (10 ml) was heated at reflux for 30 minutes. Water was added and the mixture extracted with dichloromethane. The organic phase was separated and the solvent evaporated under reduced pressure. The residue was washed with diethyl ether, affording 0.19 g of 6-nitro-2,2-dimethyl-3-(N-methyl-N-hydroxyamino)methyl-4-(2-oxo-1,2-dihydropyridin-1-yl)-2H-1-benzopyran, m.p. 159° C.

B. Preparation of Formula (I) where $R^1$ and $R^2$ are methyl, $R^5$ and $R^6$ are hydrogen, and $R^4$ is 2-oxo-1,2-dihydropyridin-1-yl, varying $R^3$, $R^8$ and $R^9$ Similarly, optionally replacing 6-nitro-2,2-dimethyl-3-bromomethyl-4-(2-oxo-1,2-dihydropyridin-1-yl)-2H-1-benzopyran with an appropriate compound of Formula (14), prepared, for example, as shown in Preparation 15 or in Preparation 16, and optionally replacing N-methylhydroxylamine hydrochloride with an amine of formula $HNR^8R^9$, where $R^8$ is hydroxy or lower alkoxy and $R^9$ is hydrogen or lower alkyl, and following the procedure of Example 2A above, the following compounds of Formula (I) were prepared:

6-nitro-2,2-dimethyl-3-(hydroxyamino)methyl-4-(2-oxo-1,2-dihydropyridin-1-yl)-2H-1-benzopyran, m.p. >250° C.;

6-nitro-2,2-dimethyl-3-(methoxyamino)methyl-4-(2-oxo-1,2-dihydropyridin-1-yl)-2H-1-benzopyran, m.p. 196° C.;

6-cyano-2,2-dimethyl-3-(N-methyl-N-hydroxyamino)methyl-4-(2-oxo-1,2-dihydropyridin-1-yl)-2H-1-benzopyran, m.p. 165° C.;

6-trifluoromethyl-2,2-dimethyl-3-(hydroxyamino)methyl-4-(2-oxo-1,2-dihydropyridin-1-yl)-2H-1-benzopyran, m.p. 90° C.;

6-trifluoromethyl-2,2-dimethyl-3-(methoxyamino)methyl-4-(2-oxo-1,2-dihydropyridin-1-yl)-2H-1-benzopyran, m.p. 160° C.;

6-trifluoromethyl-2,2-dimethyl-3-(N-methylhydroxyamino)methyl-4-(2-oxo-1,2-dihydropyridin-1-yl)-2H-1-benzopyran, m.p. 145° C.; and 6-pentafluoroethyl-2,2-dimethyl-3-(hydroxyamino)methyl-4-(2-oxo-1,2-dihydropyridin-1-yl)-2H-1-benzopyran, as an oil $^1$NMR (CDCl$_3$) δ1.6 (s, 2H), 1.6 (s, 2H), 3.6 (s, 2H), 5.35 (br.s, 2H), 6.3–7.6 (m, 7H).

6-bromo-2,2-dimethyl-3-(hydroxyamino)methyl-4-(2-oxo-1,2-dihydropyridin-1-yl)-2H-1-benzopyran, m.p. 170° C.;

6-chloro-2,2-dimethyl-3-(hydroxyamino)methyl-4-(2-oxo-1,2-dihydropyridin-1-yl)-2H-1-benzopyran, m.p. 113° C.; and 2,2-dimethyl-3-(hydroxyamino)methyl-4-(2-oxo-1,2-dihydropyridin-1-yl)-2H-1-benzopyran, m.p. 106° C.

C. Preparation of Formula (I) where $R^1$ and $R^2$ are methyl and $R^5$ and $R^6$ are hydrogen, varying $R^3$, $R^4$, $R^8$ and $R^9$ Similarly, optionally replacing 6-nitro-2,2-dimethyl-3-bromomethyl-4-(2-oxo-1,2-dihydropyridin-1-yl)-2H-1-benzopyran with an appropriate compound of Formula (14), prepared, for example, as shown in Preparation 15, and optionally replacing N-methylhydroxylamine hydrochloride with an amine of formula $HNR^8R^9$, where $R^8$ is hydroxy or lower alkoxy and $R^9$ is hydrogen or lower alkyl, and following the procedure of Example 2A above, the following compounds of Formula (I) are prepared:

6-nitro-2,2-dimethyl-3-(ethoxyamino)methyl-4-(2-oxo-1,2-dihydropyridin-1-yl)-2H-1-benzopyran;

6-nitro-2,2-dimethyl-3-(N-methyl-N-methoxyamino)methyl-4-(2-oxo-1,2-dihydropyridin-1-yl)-2H-1-benzopyran;

6-nitro-2,2-dimethyl-3-(N-ethyl-N-hydroxyamino)methyl-4-(2-oxo-1,2-dihydropyridin-1-yl)-2H-1-benzopyran;

6-cyano-2,2-dimethyl-3-(hydroxyamino)methyl-4-(2-oxo-1,2-dihydropyridin-1-yl)-2H-1-benzopyran;

6-cyano-2,2-dimethyl-3-(methoxyamino)methyl-4-(2-oxo-1,2-dihydropyridin-1-yl)-2H-1-benzopyran;

6-cyano-2,2-dimethyl-3-(ethoxyamino)methyl-4-(2-oxo-1,2-dihydropyridin-1-yl)-2H-1-benzopyran;

6-cyano-2,2-dimethyl-3-(N-methyl-N-methoxyamino)methyl-4-(2-oxo-1,2-dihydropyridin-1-yl)-2H-1-benzopyran;

6-cyano-2,2-dimethyl-3-(N-ethyl-N-hydroxyamino)methyl-4-(2-oxo-1,2-dihydropyridin-1-yl)-2H-1-benzopyran;

6-trifluoromethyl-2,2-dimethyl-3-(ethoxyamino)methyl-4-(2-oxo-1,2-dihydropyridin-1-yl)-2H-1-benzopyran;

6-trifluoromethyl-2,2-dimethyl-3-(N-methyl-N-methoxyamino)methyl-4-(2-oxo-1,2-dihydropyridin-1-yl)-2H-1-benzopyran;

6-trifluoromethyl-2,2-dimethyl-3-(N-ethyl-N-hydroxyamino)methyl-4-(2-oxo-1,2-dihydropyridin-1-yl)-2H-1-benzopyran;

6-pentafluoroethyl-2,2-dimethyl-3-(N-methyl-N-hydroxyamino)methyl-4-(2-oxo-1,2-dihydropyridin-1-yl)-2H-1-benzopyran;

6-pentafluoroethyl-2,2-dimethyl-3-(methoxyamino)methyl-4-(2-oxo-1,2-dihydropyridin-1-yl)-2H-1-benzopyran;

6-pentafluoroethyl-2,2-dimethyl-3-(ethoxyamino)methyl-4-(2-oxo-1,2-dihydropyridin-1-yl)-2H-1-benzopyran;

6-pentafluoroethyl-2,2-dimethyl-3-(N-methyl-N-methoxyamino)methyl-4-(2-oxo-1,2-dihydropyridin-1-yl)-2H-1-benzopyran;

6-pentafluoroethyl-2,2-dimethyl-3-(N-ethyl-N-hydroxyamino)methyl-4-(2-oxo-1,2-dihydropyridin-1-yl)-2H-1-benzopyran;

6-nitro-2,2-dimethyl-3-(N-methyl-N-hydroxyamino)methyl-4-(2-oxopyrrolidin-1-yl)-2H-1-benzopyran;

6-nitro-2,2-dimethyl-3-(hydroxyamino)methyl-4-(2-oxopyrrolidin-1-yl)-2H-1-benzopyran;

6-nitro-2,2-dimethyl-3-(methoxyamino)methyl-4-(2-oxopyrrolidin-1-yl)-2H-1-benzopyran;

6-nitro-2,2-dimethyl-3-(ethoxyamino)methyl-4-(2-oxopyrrolidin-1-yl)-2H-1-benzopyran;

6-nitro-2,2-dimethyl-3-(N-methyl-N-methoxyamino)methyl-4-(2-oxopyrrolidin-1-yl)-2H-1-benzopyran;

6-nitro-2,2-dimethyl-3-(N-ethyl-N-hydroxyamino)methyl-4-(2-oxopyrrolidin-1-yl)-2H-1-benzopyran;

6-cyano-2,2-dimethyl-3-(N-methyl-N-hydroxyamino)methyl-4-(2-oxopyrrolidin-1-yl)-2H-1-benzopyran;

6-cyano-2,2-dimethyl-3-(hydroxyamino)methyl-4-(2-oxopyrrolidin-1-yl)-2H-1-benzopyran;

6-cyano-2,2-dimethyl-3-(methoxyamino)methyl-4-(2-oxopyrrolidin-1-yl)-2H-1-benzopyran;

6-cyano-2,2-dimethyl-3-(ethoxyamino)methyl-4-(2-oxopyrrolidin-1-yl)-2H-1-benzopyran;

6-cyano-2,2-dimethyl-3-(N-methyl-N-methoxyamino)methyl-4-(2-oxopyrrolidin-1-yl)-2H-1-benzopyran;

6-cyano-2,2-dimethyl-3-(N-ethyl-N-hydroxyamino)methyl-4-(2-oxopyrrolidin-1-yl)-2H-1-benzopyran;

6-trifluoromethyl-2,2-dimethyl-3-(N-methyl-N-hydroxyamino)methyl-4-(2-oxopyrrolidin-1-yl)-2H-1-benzopyran;

6-trifluoromethyl-2,2-dimethyl-3-(hydroxyamino)methyl-4-(2-oxopyrrolidin-1-yl)-2H-1-benzopyran;

6-trifluoromethyl-2,2-dimethyl-3-(methoxyamino)methyl-4-(2-oxopyrrolidin-1-yl)-2H-1-benzopyran;

6-trifluoromethyl-2,2-dimethyl-3-(ethoxyamino)methyl-4-(2-oxopyrrolidin-1-yl)-2H-1-benzopyran;

6-trifluoromethyl-2,2-dimethyl-3-(N-methyl-N-methoxyamino)methyl-4-(2-oxopyrrolidin-1-yl)-2H-1-benzopyran;

6-trifluoromethyl-2,2-dimethyl-3-(N-ethyl-N-hydroxyamino)methyl-4-(2-oxopyrrolidin-1-yl)-2H-1-benzopyran;

6-pentafluoroethyl-2,2-dimethyl-3-(N-methyl-N-hydroxyamino)methyl-4-(2-oxopyrrolidin-1-yl)-2H-1-benzopyran;

6-pentafluoroethyl-2,2-dimethyl-3-(hydroxyamino)methyl-4-(2-oxopyrrolidin-1-yl)-2H-1-benzopyran;

6-pentafluoroethyl-2,2-dimethyl-3-(methoxyamino)methyl-4-(2-oxopyrrolidin-1-yl)-2H-1-benzopyran;

6-pentafluoroethyl-2,2-dimethyl-3-(N-methyl-N-hydroxyamino)methyl-4-(2-oxopyrrolidin-1-yl)-2H-1-benzopyran;

6-pentafluoroethyl-2,2-dimethyl-3-(methoxyamino)methyl-4-(2-oxopyrrolidin-1-yl)-2H-1-benzopyran;

6-pentafluoroethyl-2,2-dimethyl-3-(ethoxyamino)methyl-4-(2-oxopyrrolidin-1-yl)-2H-1-benzopyran;

6-pentafluoroethyl-2,2-dimethyl-3-(N-methyl-N-methoxyamino)methyl-4-(2-oxopyrrolidin-1-yl)-2H-1-benzopyran;

6-pentafluoroethyl-2,2-dimethyl-3-(N-ethyl-N-hydroxyamino)methyl-4-(2-oxopyrrolidin-1-yl)-2H-1-benzopyran;

6-nitro-2,2-dimethyl-3-(N-methyl-N-hydroxyamino)methyl-4-(1-oxo-isoindolin-2-yl)-2H-1-benzopyran;

6-nitro-2,2-dimethyl-3-(hydroxyamino)methyl-4-(1-oxoisoindolin-2-yl)-2H-1-benzopyran;

6-nitro-2,2-dimethyl-3-(methoxyamino)methyl-4-(1-oxoisoindolin-2-yl)-2H-1-benzopyran;

6-nitro-2,2-dimethyl-3-(ethoxyamino)methyl-4-(1-oxoisoindolin-2-yl)-2H-1-benzopyran;

6-nitro-2,2-dimethyl-3-(N-methyl-N-methoxyamino)methyl-4-(1-oxo-isoindolin-2-yl)-2H-1-benzopyran;

6-nitro-2,2-dimethyl-3-(N-ethyl-N-hydroxyamino)methyl-4-(1-oxo-isoindolin-2-yl)-2H-1-benzopyran;

6-cyano-2,2-dimethyl-3-(N-methyl-N-hydroxyamino)methyl-4-(1-oxo-isoindolin-2-yl)-2H-1-benzopyran;

6-cyano-2,2-dimethyl-3-(hydroxyamino)methyl-4-(1-oxoisoindolin-2-yl)-2H-1-benzopyran;

6-cyano-2,2-dimethyl-3-(methoxyamino)methyl-4-(1-oxoisoindolin-2-yl)-2H-1-benzopyran;

6-cyano-2,2-dimethyl-3-(ethoxyamino)methyl-4-(1-oxoisoindolin-2-yl)-2H-1-benzopyran;

6-cyano-2,2-dimethyl-3-(N-methyl-N-methoxyamino)methyl-4-(1-oxo-isoindolin-2-yl)-2H-1-benzopyran;

6-cyano-2,2-dimethyl-3-(N-ethyl-N-hydroxyamino)methyl-4-(1-oxo-isoindolin-2-yl)-2H-1-benzopyran;

6-trifluoromethyl-2,2-dimethyl-3-(N-methyl-N-hydroxyamino)methyl-4-(1-oxo-isoindolin-2-yl)-2H-1-benzopyran;

6-trifluoromethyl-2,2-dimethyl-3-(hydroxyamino)methyl-4-(1-oxo-isoindolin-2-yl)-2H-1-benzopyran;

6-trifluoromethyl-2,2-dimethyl-3-(methoxyamino)methyl-4-(1-oxo-isoindolin-2-yl)-2H-1-benzopyran;

6-trifluoromethyl-2,2-dimethyl-3-(ethoxyamino)methyl-4-(1-oxo-isoindolin-2-yl)-2H-1-benzopyran;

6-trifluoromethyl-2,2-dimethyl-3-(N-methyl-N-methoxyamino)methyl-4-(1-oxo-isoindolin-2-yl)-2H-1-benzopyran;

6-trifluoromethyl-2,2-dimethyl-3-(N-ethyl-N-hydroxyamino)methyl-4-(1-oxo-isoindolin-2-yl)-2H-1-benzopyran;

6-pentafluoroethyl-2,2-dimethyl-3-(N-methyl-N-hydroxyamino)methyl-4-(1-oxo-isoindolin-2-yl)-2H-1-benzopyran;

6-pentafluoroethyl-2,2-dimethyl-3-(hydroxyamino)methyl-4-(1-oxo-isoindolin-2-y)-2H-1-benzopyran;

6-pentafluoroethyl-2,2-dimethyl-3-(methoxyamino)methyl-4-(1-oxo-isoindolin-2-yl)-2H-1-benzopyran;

6-pentafluoroethyl-2,2-dimethyl-3-(N-methyl-N-hydroxyamino)methyl-4-(1-oxo-isoindolin-2-yl)-2H-1-benzopyran;

6-pentafluoroethyl-2,2-dimethyl-3-(methoxyamino)methyl-4-(1-oxo-isoindolin-2-yl)-2H-1-benzopyran.

6-pentafluoroethyl-2,2-dimethyl-3-(ethoxyamino)methyl-4-(1-oxo-isoindolin-2-yl)-2H-1-benzopyran;

6-pentafluoroethyl-2,2-dimethyl-3-(N-methyl-N-methoxyamino)methyl-4-(1-oxo-isoindolin-2-yl)-2H-1-benzopyran; and 6-pentafluoroethyl-2,2-dimethyl-3-(N-ethyl-N-hydroxyamino)methyl-4-(1-oxo-isoindolin-2-yl)-2H-1-benzopyran.

EXAMPLE 3

Preparation of Compounds of Formula (I) wherein $R^9$ is $COR^{12}$, in which $R^{12}$ is hydrogen A. Preparation of Formula (I) where $R^3$ is nitro, $R^1$ and $R^2$ are methyl, $R^5$ and $R^6$ are hydrogen, $R^4$ is 2-oxo-1,2-dihydropyridin-1-yl, $R^8$ is hydrogen and $R^9$ is $COR^{12}$, where $R^{12}$ is hydrogen A solution of 6-nitro-2,2-dimethyl-3-aminomethyl-4-(2-oxo-1,2-dihydropyridin-1-yl)-2H-1-benzopyran (0.5 g, 1.53 mmol) in methyl formate (10 ml) was heated at reflux for twenty seven hours. The solvent was evaporated under reduced pressure and the residue washed with diethyl ether, to give 0.42 g of 6-nitro-2,2-dimethyl-3-(formamido)methyl-4-(2-oxo-1,2-dihydropyridin-1-yl)-2H-1-benzopyran, m.p. 170° C.

B. Preparation of Formula (I) where $R^1$ and $R^2$ are methyl, $R^5$ and $R^6$ are hydrogen, $R^4$ is 2-oxo-1,2-dihydropyridin-1-yl, $R^8$ is hydrogen and $R^9$ is $COR^{12}$, in which $R^{12}$ is hydrogen, varying $R^3$ Similarly, replacing 6-nitro-2,2-dimethyl-3-aminomethyl-4-(2-oxo-1,2-dihydropyridin-1-yl)-2H-1-benzopyran with an appropriate compound of Formula (15), prepared, for example, as shown in Preparation 17, and following the procedure of Example 3A above, the following compounds of Formula (I) were prepared:

6-cyano-2,2-dimethyl-3-(formamido)methyl-4-(2-oxo-1,2-dihydropyridin-1-yl)-2H-1-benzopyran, m.p. 165° C.; and 6-trifluoromethyl-2,2-dimethyl-3-(formamido)methyl-4-(2-oxo-1,2-dihydropyridin-1-yl)-2H-1-benzopyran, m.p. 169° C.

C. Preparation of Formula (I) where $R^1$ and $R^2$ are methyl, $R^5$ and $R^6$ are hydrogen $R^9$ is $COR^{12}$, in which $R^{12}$ is hydrogen, varying $R^3$, $R^4$ and $R^8$ Similarly, optionally replacing 6-nitro-2,2-dimethyl-3-aminomethyl-4-(2-oxo-1,2-dihydropyridin-1-yl)-2H-1-benzopyran with an appropriate compound of Formula (15) or Formula (IA), prepared, for example, as shown in Preparation 17 or Examples 1 and 2, and following the procedure of Example 3A above, the following compounds of Formula (I) are prepared:

6-nitro-2,2-dimethyl-3-(N-methylformamido)methyl-4-(2-oxo-1,2-dihydropyridin-1-yl)-2H-1-benzopyran;

6-nitro-2,2-dimethyl-3-(N-hydroxyformamido)methyl-4-(2-oxo-1,2-dihydropyridin-1-yl)-2H-1-benzopyran;

6-nitro-2,2-dimethyl-3-(N-methoxyformamido)methyl-4-(2-oxo-1,2-dihydropyridin-1-yl)-2H-1-benzopyran;

6-cyano-2,2-dimethyl-3-(N-methylformamido)methyl-4-(2-oxo-1,2-dihydropyridin-1-yl)-2H-1-benzopyran;

6-cyano-2,2-dimethyl-3-(N-hydroxyformamido)methyl-4-(2-oxo-1,2-dihydropyridin-1-yl)-2H-1-benzopyran;

6-cyano-2,2-dimethyl-3-(N-methoxyformamido)methyl-4-(2-oxo-1,2-dihydropyridin-1-yl)-2H-1-benzopyran;

6-trifluoromethyl-2,2-dimethyl-3-(N-methylformamido)methyl-4-(2-oxo-1,2-dihydropyridin-1-yl)-2H-1-benzopyran;

6-trifluoromethyl-2,2-dimethyl-3-(N-hydroxyformamido)methyl-4-(2-oxo-1,2-dihydropyridin-1-yl)-2H-1-benzopyran;

6-trifluoromethyl-2,2-dimethyl-3-(N-methoxyformamido)methyl-4-(2-oxo-1,2-dihydropyridin-1-yl)-2H-1-benzopyran;

6-pentafluoroethyl-2,2-dimethyl-3-(formamido)methyl-4-(2-oxo-1,2-dihydropyridin-1-yl)-2H-1-benzopyran;

6-pentafluoroethyl-2,2-dimethyl-3-(N-methylformamido)methyl-4-(2-oxo-1,2-dihydropyridin-1-yl)-2H-1-benzopyran;

6-pentafluoroethyl-2,2-dimethyl-3-(N-hydroxyformamido)methyl-4-(2-oxo-1,2-dihydropyridin-1-yl)-2H-1-benzopyran; 6-pentafluoroethyl-2,2-dimethyl-3-(N-methoxyformamido)-methyl-4-(2-oxo-1,2-dihydropyridin-1-yl)-2H-1-benzopyran;

6-nitro-2,2-dimethyl-3-(N-methylformamido)methyl-4-(2-oxopyrrolidin-1-yl)-2H-1-benzopyran;

6-nitro-2,2-dimethyl-3-(N-hydroxyformamido)methyl-4-(2-oxopyrrolidin-1-yl)-2H-1-benzopyran;

6-nitro-2,2-dimethyl-3-(N-methoxyformamido)methyl-4-(2-oxopyrrolidin-1-yl)-2H-1-benzopyran;

6-cyano-2,2-dimethyl-3-(N-methylformamido)methyl-4-(2-oxopyrrolidin-1-yl)-2H-1-benzopyran;

6-cyano-2,2-dimethyl-3-(N-hydroxyformamido)methyl-4-(2-oxopyrrolidin-1-yl)-2H-1-benzopyran;

6-cyano-2,2-dimethyl-3-(N-methoxyformamido)methyl-4-(2-oxopyrrolidin-1-yl)-2H-1-benzopyran;

6-trifluoromethyl-2,2-dimethyl-3-(N-methylformamido)methyl-4-(2-oxopyrrolidin-1-yl)-2H-1-benzopyran;

6-trifluoromethyl-2,2-dimethyl-3-(N-hydroxyformamido)methyl-4-(2-oxopyrrolidin-1-yl)-2H-1-benzopyran;

6-trifluoromethyl-2,2-dimethyl-3-(N-methoxyformamido)methyl-4-(2-oxopyrrolidin-1-yl)-2H-1-benzopyran;

6-pentafluoroethyl-2,2-dimethyl-3-(formamido)methyl-4-(2-oxopyrrolidin-1-yl)-2H-1-benzopyran;

6-pentafluoroethyl-2,2-dimethyl-3-(N-methylformamido)methyl-4-(2-oxopyrrolidin-1-yl)-2H-1-benzopyran;

6-pentafluoroethyl-2,2-dimethyl-3-(N-hydroxyformamido)methyl-4-(2-oxopyrrolidin-1-yl)-2H-1-benzopyran;

6-pentafluoroethyl-2,2-dimethyl-3-(N-methoxyformamido)methyl-4-(2-oxopyrrolidin-1-yl)-2H-1-benzopyran.

6-nitro-2,2-dimethyl-3-(N-methylformamido)methyl-4-(1-oxo-isoindolin-2-yl)-2H-1-benzopyran;

6-nitro-2,2-dimethyl-3-(N-hydroxyformamido)methyl-4-(1-oxo-isoindolin-2-yl)-2H-1-benzopyran;

6-nitro-2,2-dimethyl-3-(N-methoxyformamido)methyl-4-(1-oxo-isoindolin-2-yl)-2H-1-benzopyran;

6-cyano-2,2-dimethyl-3-(N-methylformamido)methyl-4-(1-oxo-isoindolin-2-yl)-2H-1-benzopyran;

6-cyano-2,2-dimethyl-3-(N-hydroxyformamido)methyl-4-(1-oxo-isoindolin-2-yl)-2H-1-benzopyran;

6-cyano-2,2-dimethyl-3-(N-methoxyformamido)methyl-4-(1-oxo-isoindolin-2-yl)-2H-1-benzopyran;

6-trifluoromethyl-2,2-dimethyl-3-(N-methylformamido)methyl-4-(1-oxo-isoindolin-2-yl)-2H-1-benzopyran;

6-trifluoromethyl-2,2-dimethyl-3-(N-hydroxyformamido)methyl-4-(1-oxo-isoindolin-2-yl)-2H-1-benzopyran;

6-trifluoromethyl-2,2-dimethyl-3-(N-methoxyformamido)methyl-4-(1-oxo-isoindolin-2-yl)-2H-1-benzopyran;

6-pentafluoroethyl-2,2-dimethyl-3-(formamido)methyl-4-(1-oxo-isoindolin-2-yl)-2H-1-benzopyran;

6-pentafluoroethyl-2,2-dimethyl-3-(N-methylfor-
mamido)methyl-4-(1-oxo-isoindolin-2-yl)-2H-1-ben-
zopyran;
6-pentafluoroethyl-2,2-dimethyl-3-(N-hydroxyfor-
mamido)methyl-4-(1-oxo-isoindolin-2-yl)-2H-1-ben-
zopyran; and
6-pentafluoroethyl-2,2-dimethyl-3-(N-methoxyfor-
mamido)methyl-4-(1-oxo-isoindolin-2-yl)-2H-1-ben-
zopyran.

EXAMPLE 4

Preparation of Compounds of Formula (I) wherein $R^8$ is hydrogen, lower alkyl or lower alkoxy and $R^9$ is $COR^{12}$, where $R^{12}$ is lower alkyl or fluoro lower alkyl A. Preparation of Formula (I) where $R^3$ is nitro, $R^1$ and $R^2$ are methyl, $R^5$ and $R^6$ are hydrogen, $R^4$ is 2-oxo-1,2-dihydropyridin-1-yl, $R^8$ is hydrogen and $R^9$ is $COR^{12}$, where $R^{12}$ is trifluoromethyl A solution of 6-nitro-2,2-dimethyl-3-aminomethyl-4-(2-oxo-1,2-dihydropyridin-1-yl)-2H-1-benzopyran (0.5 g, 1.53 mmol) and triethylamine (0.25 ml, 1.8 mmol) in dichloromethane (20 ml) at 0° C. was treated with trifluoroacetic anhydride (0.26 ml, 1.8 mmol), and the mixture stirred at room temperature for four hours. Water was added and the organic phase separated and evaporated. The residue was triturated with diethyl ether to give 0.53 g of 6-nitro-2,2-dimethyl-3-(trifluoroacetamido)-4-(2-oxo-1,2-dihydropyridin-1-yl)-2H-1-benzopyran, m.p. 189° C.

B. Preparation of Formula (I) where $R^1$ and $R^2$ are methyl, $R^5$ and $R^6$ are hydrogen, $R^4$ is 2-oxo-1,2-dihydropyridin-1-yl, and $R^9$ is $COR^{12}$, where $R^{12}$ is trifluoroacetyl, varying $R^3$, $R^8$ and $R^{12}$ In a similar manner, but optionally replacing 6-nitro-2,2-dimethyl-3-aminomethyl-4-(2-oxo-1,2-dihydropyridin-1-yl)-2H-1-benzopyran with an appropriate compound of Formula (15) or Formula (IA), prepared, for example, as shown in Preparation 17 or Examples 1 and 2, and following the procedure of Example 4A above, the following compounds of Formula (I) were prepared:
6-nitro-2,2-dimethyl-3-(N-methyltrifluoroacetamidomethyl)-4-(2-oxo-1,2-dihydropyridin-1-yl)-2H-1-benzopyran, m.p. 178° C.;
6-cyano-2,2-dimethyl-3-(trifluoroacetamido)methyl-4-(2-oxo-1,2-dihydropyridin-1-yl)-2H-1-benzopyran, m.p. 190° C.; and
6-trifluoromethyl-2,2-dimethyl-3-(trifluoroacetamido)methyl-4-(2-oxo-1,2-dihydropyridin-1-yl)-2H-1-benzopyran, m.p. 168° C.

C. Preparation of Formula (I) where $R^1$ and $R^2$ are methyl, $R^5$ and $R^6$ are hydrogen, and $R^9$ is $COR^{12}$, varying $R^3$, $R^4$, $R^8$ and $R^{12}$ In a similar manner, but optionally replacing 6-nitro-2,2-dimethyl-3-aminomethyl-4-(2-oxo-1,2-dihydropyridin-1-yl)-2H-1-benzopyran with an appropriate compound of Formula (15) or Formula (IA), prepared, for example, as shown in Preparation 17 or Examples 1 and 2, and optionally replacing trifluoroacetic anhydride with other anhydrides of the Formula $(R^{12}CO)_2O$, where $R^{12}$ is lower alkyl or fluoro lower alkyl, or an appropriate acyl halide of formula $R^{12}COCl$ or $R^{12}COBr$, where $R^{12}$ is lower alkyl, and following the procedure of Example 4A above, the following compounds of Formula (I) are prepared:
6-nitro-2,2-dimethyl-3-(acetamido)methyl-4-(2-oxo-1,2-dihydropyridin-1-yl)-2H-1-benzopyran;
6-nitro-2,2-dimethyl-3-(propanamido)methyl-4-(2-oxo-1,2-dihydropyridin-1-yl)-2H-1-benzopyran;
6-nitro-2,2-dimethyl-3-(isobutanamido)methyl-4-(2-oxo-1,2-dihydropyridin-1-yl)-2H-1-benzopyran;
6-cyano-2,2-dimethyl-3-(acetamido)methyl-4-(2-oxo-1,2-dihydropyridin-1-yl)-2H-1-benzopyran;
6-nitro-2,2-dimethyl-3-(pentafluoropropionamido)-methyl-4-(2-oxo-1,2-dihydropyridin-1-yl)-2H-1-benzopyran;
6-cyano-2,2-dimethyl-3-(N-methyltrifluoroacetamido)-methyl-4-(2-oxo-1,2-dihydropyridin-1-yl)-2H-1-benzopyran;
6-cyano-2,2-dimethyl-3-(pentafluoropropionamido)-methyl-4-(2-oxo-1,2-dihydropyridin-1-yl)-2H-1-benzopyran;
6-trifluoromethyl-2,2-dimethyl-3-(acetamido)methyl-4-(2-oxo-1,2-dihydropyridin-1-yl)-2H-1-benzopyran;
6-trifluoromethyl-2,2-dimethyl-3-(N-methyltrifluoroacetamido)methyl-4-(2-oxo-1,2-dihydropyridin-1-yl)-2H-1-benzopyran;
6-trifluoromethyl-2,2-dimethyl-3-(pentafluoropropionamido)methyl-4-(2-oxo-1,2-dihydropyridin-1-yl)-2H-1-benzopyran;
6-pentafluoroethyl-2,2-dimethyl-3-(acetamido)methyl-4-(2-oxo-1,2-dihydropyridin-1-yl)-2H-1-benzopyran;
6-pentafluoroethyl-2,2-dimethyl-3-(N-methyltrifluoroacetamido)methyl-4-(2-oxo-1,2-dihydropyridin-1-yl)-2H-1-benzopyran;
6-pentafluoroethyl-2,2-dimethyl-3-(pentafluoropropionamido)methyl-4-(2-oxo-1,2-dihydropyridin-1-yl)-2H-1-benzopyran;
6-nitro-2,2-dimethyl-3-(acetamido)methyl-4-(2-oxopyrrolidin-1-yl)-2H-1-benzopyran;
6-nitro-2,2-dimethyl-3-(trifluoroacetamido)methyl-4-(2-oxopyrrolidin-1-yl)-2H-1-benzopyran;
6-nitro-2,2-dimethyl-3-(N-methyltrifluoroacetamido)-methyl-4-(2-oxopyrrolidin-1-yl)-2H-1-benzopyran;
6-nitro-2,2-dimethyl-3-(pentafluoropropionamido)-methyl-4-(2-oxopyrrolidin-1-yl)-2H-1-benzopyran;
6-cyano-2,2-dimethyl-3-(acetamido)methyl-4-(2-oxopyrrolidin-1-yl)-2H-1-benzopyran;
6-cyano-2,2-dimethyl-3-(trifluoroacetamido)methyl-4-(2-oxopyrrolidin-1-yl)-2H-1-benzopyran;
6-cyano-2,2-dimethyl-3-(N-methyltrifluoroacetamido)-methyl-4-(2-oxopyrrolidin-1-yl)-2H-1-benzopyran;
6-cyano-2,2-dimethyl-3-(pentafluoropropionamido)-methyl-4-(2-oxopyrrolidin-1-yl)-2H-1-benzopyran;
6-trifluoromethyl-2,2-dimethyl-3-(acetamido)methyl-4-(2-oxopyrrolidin-1-yl)-2H-1-benzopyran;
6-trifluoromethyl-2,2-dimethyl-3-(trifluoroacetamido)methyl-4-(2-oxopyrrolidin-1-yl)-2H-1-benzopyran;
6-trifluoromethyl-2,2-dimethyl-3-(N-methyltrifluoroacetamido)methyl-4-(2-oxopyrrolidin-1-yl)-2H-1-benzopyran;
6-trifluoromethyl-2,2-dimethyl-3-(pentafluoropropionamido)methyl-4-(2-oxopyrrolidin-1-yl)-2H-1-benzopyran;
6-pentafluoroethyl-2,2-dimethyl-3-(acetamido)methyl-4-(2-oxopyrrolidin-1-yl)-2H-1-benzopyran;
6-pentafluoroethyl-2,2-dimethyl-3-(trifluoroacetamido)methyl-4-(2-oxopyrrolidin-1-yl)-2H-1-benzopyran;
6-pentafluoroethyl-2,2-dimethyl-3-(N-methyltrifluoroacetamido)methyl-4-(2-oxopyrrolidin-1-yl)-2H-1-benzopyran;
6-pentafluoroethyl-2,2-dimethyl-3-(pentafluoropropionamido)methyl-4-(2-oxopyrrolidin-1-yl)-2H-1-benzopyran;

6-nitro-2,2-dimethyl-3-(acetamido)methyl-4-(1-oxo-isoindolin-2-yl)-2H-1-benzopyran;
6-nitro-2,2-dimethyl-3-(trifluoroacetamido)methyl-4-(1-oxo-isoindolin-2-yl)-2H-1-benzopyran;
6-nitro-2,2-dimethyl-3-(N-methyltrifluoroacetamido)-methyl-4-(1-oxo-isoindolin-2-yl)-2H-1-benzopyran;
6-nitro-2,2-dimethyl-3-(pentafluoropropionamido)-methyl-4-(1-oxo-isoindolin-2-yl)-2H-1-benzopyran;
6-cyano-2,2-dimethyl-3-(acetamido)methyl-4-(1-oxo-isoindolin-2-yl)-2H-1-benzopyran;
6-cyano-2,2-dimethyl-3-(trifluoroacetamido)methyl-4-(1-oxo-isoindolin-2-yl)-2H-1-benzopyran;
6-cyano-2,2-dimethyl-3-(N-methyltrifluoroacetamido)-methyl-4-(1-oxo-isoindolin-2-yl)-2H-1-benzopyran;
6-cyano-2,2-dimethyl-3-(pentafluoropropionamido)-methyl-4-(1-oxo-isoindolin-2-yl)-2H-1-benzopyran;
6-trifluoromethyl-2,2-dimethyl-3-(acetamido)methyl-4-(1-oxo-isoindolin-2-yl)-2H-1-benzopyran;
6-trifluoromethyl-2,2-dimethyl-3-(trifluoroacetamido)-methyl-4-(1-oxo-isoindolin-2-yl)-2H-1-benzopyran;
6-trifluoromethyl-2,2-dimethyl-3-(N-methyltrifluoroacetamido)methyl-4-(1-oxo-isoindolin-2-yl)-2H-1-benzopyran;
6-trifluoromethyl-2,2-dimethyl-3-(pentafluoropropionamido)methyl-4-(1-oxo-isoindolin-2-yl)-2H-1-benzopyran;
6-pentafluoroethyl-2,2-dimethyl-3-(acetamido)methyl-4-(1-oxo-isoindolin-2-yl)-2H-1-benzopyran;
6-pentafluoroethyl-2,2-dimethyl-3-(trifluoroacetamido)methyl-4-(1-oxo-isoindolin-2-yl)-2H-1-benzopyran;
6-pentafluoroethyl-2,2-dimethyl-3-(N-methyltrifluoroacetamido)methyl-4-(1-oxo-isoindolin-2-yl)-2H-1-benzopyran; and
6-pentafluoroethyl-2,2-dimethyl-3-(pentafluoropropionamido)methyl-4-(1-oxo-isoindolin-2-yl)-2H-1-benzopyran.

EXAMPLE 5

Preparation of Compounds of Formula (I) wherein $R^8$ is hydroxy and $R^9$ is $COR^{12}$, where $R^{12}$ is lower alkyl or fluoro lower alkyl A. Preparation of Formula (I) where $R^3$ is trifluoromethyl, $R^1$ and $R^2$ are methyl, $R^5$ and $R^6$ are hydrogen, $R^4$ is 2-oxo-1,2-dihydropyridin-1-yl, $R^8$ is hydroxy and $R^9$ is $COR^{12}$, where $R^{12}$ is trifluoromethyl A solution of 6-trifluoromethyl-2,2-dimethyl-3-(hydroxyamino)methyl-4-(2-oxo-1,2-dihydropyridin-1-yl)-2H-1-benzopyran (0.33 g, 0.9 mmol) in dichloromethane (9 ml) was cooled to 0° C. and treated with triethylamine (0.12 ml, 0.9 mmol) and trifluoroacetic anhydride (0.12 ml, 0.9 mmol) and stirred at 0° C. during 2.5 hours. Water was added, the organic layer separated, washed with water, and dried and evaporated to give crude product. Chromatography on silica gel eluting with dichloromethane/methanol (95/5) gave an oil which was crystallized from ether to give 0.21 g of 6-trifluoromethyl-2,2-dimethyl-3-(N-hydroxytrifluoroacetamido)methyl-4-(2-oxo-1,2-dihydropyridin-1-yl)-2H-1-benzopyran, m.p. 208° C.

B. Preparation of Formula (I) where $R^3$ is nitro, $R^1$ and $R^2$ are methyl, $R^5$ and $R^6$ are hydrogen, $R^4$ is 2-oxo-1,2-dihydropyridin-1-yl, $R^8$ is hydroxy and $R^9$ is $COR^{12}$, where $R^{12}$ is methyl In a similar manner, but replacing 6-trifluoromethyl-2,2-dimethyl-3-(hydroxyamino)methyl-4-(2-oxo-1,2-dihydropyridin-1-yl)-2H-1-benzopyran with the 6-nitro analog, and replacing trifluoroacetic anhydride with acetic anhydride, and following the procedure of Example 5A above, the following compound of Formula (I) was prepared:
6-nitro-2,2-dimethyl-3-(N-hydroxyacetamido)methyl-4-(2-oxo-1,2-dihydropyridin-1-yl)-2H-1-benzopyran, m.p. 245° C.

C. Preparation of Formula (I) where $R^1$ and $R^2$ are methyl, $R^5$ and $R^6$ are hydrogen, and $R^9$ is $COR^{12}$, varying $R^3$, $R^4$, $R^8$ and $R^{12}$ In a similar manner, but optionally replacing 6-trifluoromethyl-2,2-dimethyl-3-aminomethyl-4-(2-oxo-1,2-dihydropyridin-1-yl)-2H-1-benzopyran with an appropriate compound of Formula (15) or Formula (IA), prepared, for example, as shown in Preparation 17 or Examples 1 and 2, and optionally replacing trifluoroacetic anhydride with an acyl anhydride of the Formula $(R^{12}CO)_2O$, where $R^{12}$ is lower alkyl or fluoro lower alkyl, and following the procedure of Example 5A above, the following compounds of Formula (I) are prepared:
6-nitro-2,2-dimethyl-3-(pentafluoropropionamido)-methyl-4-(2-oxo-1,2-dihydropyridin-1-yl)-2H-1-benzopyran;
6-cyano-2,2-dimethyl-3-(N-methyltrifluoroacetamido)-methyl-4-(2-oxo-1,2-dihydropyridin-1-yl)-2H-1-benzopyran;
6-cyano-2,2-dimethyl-3-(pentafluoropropionamido)-methyl-4-(2-oxo-1,2-dihydropyridin-1-yl)-2H-1-benzopyran;
6-trifluoromethyl-2,2-dimethyl-3-(acetamido)methyl-4-(2-oxo-1,2-dihydropyridin-1-yl)-2H-1-benzopyran;
6-trifluoromethyl-2,2-dimethyl-3-(N-methyltrifluoroacetamido)methyl-4-(2-oxo-1,2-dihydropyridin-1-yl)-2H-1-benzopyran;
6-trifluoromethyl-2,2-dimethyl-3-(pentafluoropropionamido)methyl-4-(2-oxo-1,2-dihydropyridin-1-yl)-2H-1-benzopyran.
6-pentafluoroethyl-2,2-dimethyl-3-(acetamido)methyl-4-(2-oxo-1,2-dihydropyridin-1-yl)-2H-1-benzopyran;
6-pentafluoroethyl-2,2-dimethyl-3-(N-methyltrifluoroacetamido)methyl-4-(2-oxo-1,2-dihydropyridin-1-yl)-2H-1-benzopyran;
6-pentafluoroethyl-2,2-dimethyl-3-(pentafluoropropionamido)methyl-4-(2-oxo-1,2-dihydropyridin-1-yl)-2H-1-benzopyran;
6-nitro-2,2-dimethyl-3-(acetamido)methyl-4-(2-oxopyrrolidin-1-yl)-2H-1-benzopyran;
6-nitro-2,2-dimethyl-3-(trifluoroacetamido)methyl-4-(2-oxopyrrolidin-1-yl)-2H-1-benzopyran;
6-nitro-2,2-dimethyl-3-(N-methyltrifluoroacetamido)-methyl-4-(2-oxopyrrolidin-1-yl)-2H-1-benzopyran;
6-nitro-2,2-dimethyl-3-(pentafluoropropionamido)-methyl-4-(2-oxopyrrolidin-1-yl)-2H-1-benzopyran;
6-cyano-2,2-dimethyl-3-(acetamido)methyl-4-(2-oxopyrrolidin-1-yl)-2H-1-benzopyran;
6-cyano-2,2-dimethyl-3-(trifluoroacetamido)methyl-4-(2-oxopyrrolidin-1-yl)-2H-1-benzopyran;
6-cyano-2,2-dimethyl-3-(N-methyltrifluoroacetamido)-methyl-4-(2-oxopyrrolidin-1-yl)-2H-1-benzopyran;
6-cyano-2,2-dimethyl-3-(pentafluoropropionamido)-methyl-4-(2-oxopyrrolidin-1-yl)-2H-1-benzopyran;
6-trifluoromethyl-2,2-dimethyl-3-(acetamido)methyl-4-(2-oxopyrrolidin-1-yl)-2H-1-benzopyran;
6-trifluoromethyl-2,2-dimethyl-3-(trifluoroacetamido)-methyl-4-(2-oxopyrrolidin-1-yl)-2H-1-benzopyran;
6-trifluoromethyl-2,2-dimethyl-3-(N-methyltrifluoroacetamido)methyl-4-(2-oxopyrrolidin-1-yl)-2H-1-benzopyran;

6-trifluoromethyl-2,2-dimethyl-3-(pentafluoropropionamido)methyl-4-(2-oxopyrrolidin-1-yl)-2H-1-benzopyran;

6-pentafluoroethyl-2,2-dimethyl-3-(acetamido)methyl-4-(2-oxopyrrolidin-1-yl)-2H-1-benzopyran;

6-pentafluoroethyl-2,2-dimethyl-3-(trifluoroacetamido)methyl-4-(2-oxopyrrolidin-1-yl)-2H-1-benzopyran;

6-pentafluoroethyl-2,2-dimethyl-3-(N-methyltrifluoroacetamido)methyl-4-(2-oxopyrrolidin-1-yl)-2H-1-benzopyran;

6-pentafluoroethyl-2,2-dimethyl-3-(pentafluoropropionamido)methyl-4-(2-oxopyrrolidin-1-yl)-2H-1-benzopyran;

6-nitro-2,2-dimethyl-3-(acetamido)methyl-4-(1-oxo-isoindolin-2-yl)-2H-1-benzopyran;

6-nitro-2,2-dimethyl-3-(trifluoroacetamido)methyl-4-(1-oxo-isoindolin-2-yl)-2H-1-benzopyran;

6-nitro-2,2-dimethyl-3-(N-methyltrifluoroacetamido)methyl-4-(1-oxo-isoindolin-2-yl)-2H-1-benzopyran;

6-nitro-2,2-dimethyl-3-(pentafluoropropionamido)methyl-4-(1-oxo-isoindolin-2-yl)-2H-1-benzopyran;

6-cyano-2,2-dimethyl-3-(acetamido)methyl-4-(1-oxo-isoindolin-2-yl)-2H-1-benzopyran;

6-cyano-2,2-dimethyl-3-(trifluoroacetamido)methyl-4-(1-oxo-isoindolin-2-yl)-2H-1-benzopyran;

6-cyano-2,2-dimethyl-3-(N-methyltrifluoroacetamido)methyl-4-(1-oxo-isoindolin-2-yl)-2H-1-benzopyran;

6-cyano-2,2-dimethyl-3-(pentafluoropropionamido)methyl-4-(1-oxo-isoindolin-2-yl)-2H-1-benzopyran;

6-trifluoromethyl-2,2-dimethyl-3-(acetamido)methyl-4-(1-oxo-isoindolin-2-yl)-2H-1-benzopyran;

6-trifluoromethyl-2,2-dimethyl-3-(trifluoroacetamido)methyl-4-(1-oxo-isoindolin-2-yl)-2H-1-benzopyran;

6-trifluoromethyl-2,2-dimethyl-3-(N-methyltrifluoroacetamido)methyl-4-(1-oxo-isoindolin-2-yl)-2H-1-benzopyran;

6-trifluoromethyl-2,2-dimethyl-3-(pentafluoropropionamido)methyl-4-(1-oxo-isoindolin-2-yl)-2H-1-benzopyran;

6-pentafluoroethyl-2,2-dimethyl-3-(acetamido)methyl-4-(1-oxo-isoindolin-2-yl)-2H-1-benzopyran;

6-pentafluoroethyl-2,2-dimethyl-3-(trifluoroacetamido)methyl-4-(1-oxo-isoindolin-2-yl)-2H-1-benzopyran;

6-pentafluoroethyl-2,2-dimethyl-3-(N-methyltrifluoroacetamido)methyl-4-(1-oxo-isoindolin-2-yl)-2H-1-benzopyran; and 6-pentafluoroethyl-2,2-dimethyl-3-(pentafluoropropionamido)methyl-4-(1-oxo-isoindolin-2-yl)-2H-1-benzopyran.

EXAMPLE 6

Alternative Preparation of Compounds of Formula (I) wherein $R^8$ is hydrogen, lower alkyl or lower alkoxy and $R^9$ is $COR^{12}$, where $R^{12}$ is lower alkyl A. Preparation of Formula (I) where $R^3$ is trifluoromethyl, $R^1$ and $R^2$ are methyl, $R^5$ and $R^6$ are hydrogen, $R^4$ is 2-oxo-1,2-dihydropyridin-1-yl, $R^8$ is hydrogen and $R^9$ is $COR^{12}$, where $R^{12}$ is methyl To a solution containing 6-trifluoromethyl-2,2-dimethyl-3-aminomethyl-4-(2-oxo-1,2-dihydropyridin-1-yl)-2H-1-benzopyran (0.68 g, 1.82 mmol) and triethylamine (0.3 ml, 2.18 mmol) in dichloromethane (18 ml), acetyl chloride (0.15 ml, 2.18 mmol) was added at room temperature. The solution was stirred for 6 hours and then water added. The organic layer was separated, dried and evaporated, to give crude product which was chromatographed on silica gel. Elution with dichloromethane/methanol (95/5) gave a product which was crystallized from ether to afford 0.3 g of 6-trifluoromethyl-2,2-dimethyl-3-(acetamido)methyl-4-(2-oxo-1,2-dihydropyridin-1-yl)2H-1-benzopyran, m.p. 174° C.

B. Preparation of Formula (I) where $R^1$ and $R^2$ are methyl, $R^5$ and $R^6$ are hydrogen, $R^4$ is 2-oxo-1,2-dihydropyridin-1-yl, $R^8$ is hydrogen and $R^9$ is $COR^{12}$, where $R^{12}$ is methyl, varying $R^3$ In a similar manner, replacing 6-trifluoromethyl-2,2-dimethyl-3-aminomethyl-4-(2-oxo-1,2-dihydropyridin-1-yl)-2H-1-benzopyran. with an appropriate compound of Formula (15), and following the procedure of Example 6A above, the following compounds of Formula (I) were prepared:

6-nitro-2,2-dimethyl-3-(acetamido)methyl-4-(2-oxo-1,2-dihydropyridin-1-yl)-2H-1-benzopyran, m.p. 218° C.;

6-nitro-2,2-dimethyl-3-(propanamido)methyl-4-(2-oxo-1,2-dihydropyridin-1-yl)-2H-1-benzopyran, m.p. 175° C.;

6-nitro-2,2-dimethyl-3-(isobutanamido)methyl-4-(2-oxo-1,2-dihydropyridin-1-yl)-2H-1-benzopyran, m.p. 180° C.; and 6-cyano-2,2-dimethyl-3-(acetamido)methyl-4-(2-oxo-1,2-dihydropyridin-1-yl)-2H-1-benzopyran, m.p. 160° C.

C. Preparation of Formula (I) where $R^1$ and $R^2$ are methyl, $R^5$ and $R^6$ are hydrogen, and $R^9$ is $COR^{12}$, varying $R^3$, $R^4$, $R^8$, and $R^{12}$ In a similar manner, optionally replacing 6-trifluoromethyl-2,2-dimethyl-3-aminomethyl-4-(2-oxo-1,2-dihydropyridin-1-yl)-2H-1-benzopyran with an appropriate compound of Formula (15) or (IA), prepared, for example, as shown in Preparation 17 or Examples 1 and 2, and optionally replacing acetyl chloride by the appropriate acyl halide of the formula $R^{12}COCl$ or $R^{12}COBr$, where $R^{12}$ is lower alkyl, and following the procedure of Example 6A above, those compounds of Formula (I) where $R^{12}$ is lower alkyl as set forth in Example 4 are obtained.

EXAMPLE 7

Alternative Preparation of Compounds of Formula (I) wherein $R^8$ is hydroxy and $R^9$ is $COR^{12}$, where $R^{12}$ is lower alkyl A. Preparation of Formula (I) where $R^3$ is trifluoromethyl, $R^1$ and $R^2$ are methyl, $R^5$ and $R^6$ are hydrogen, $R^4$ is 2-oxo-1,2-dihydropyridin-1-yl, $R^8$ is hydroxy and $R^9$ is $COR^{12}$, where $R^{12}$ is methyl A solution of 6-trifluoromethyl-2,2-dimethyl-3-(hydroxyamino)methyl-4-(2-oxo-1,2-dihydropyridin-1-yl)-2H-1-benzopyran (0.48 g, 1.31 mmol) in dichloromethane (13 ml) was cooled to 0° C. and treated with triethylamine (0.18 ml, 1.31 mmol) and acetyl chloride (0.1 ml, 1.31 mmol), and stirred at 0° C. for 45 minutes. Water was added, and the organic layer separated, washed with water and dried, and evaporated to give a crude product. Chromatography on silica gel eluting with dichloromethane/methanol (95/5) gave an oil which was crystallized from ether to give 0.24 g of 6-trifluoromethyl-2,2-dimethyl-3-(N-hydroxyacetamido)methyl-4-(2-oxo-1,2-dihydropyridin-1-yl)-2H-1-benzopyran, m.p. 188° C.

B. Preparation of Formula (I) where $R^1$ and $R^2$ are methyl, $R^5$ and $R^6$ are hydrogen, $R^4$ is 2-oxo-1,2-dihydropyridin-1-yl, $R^8$ is hydroxy and $R^9$ is $COR^{12}$, where $R^{12}$ is alkyl, varying $R^3$ In a similar manner, but replacing 6-trifluoromethyl-2,2-dimethyl-3-(hydroxyamino)methyl-4-(2-oxo-1,2-dihydropyridin-1-yl)-2H-1-benzopyran with an appropriate compound of Formula (IA), prepared, for example, as shown in Examples 1 and 2, and optionally replacing acetyl chloride by the appropriate acyl halide of the formula $R^{12}COCl$, where $R^{12}$ is lower alkyl, and following the procedure of Example 7A above, the following compounds of Formula (I) were prepared:

6-nitro-2,2-dimethyl-3-(N-hydroxyacetamido)methyl-4-(2-oxo-1,2-dihydropyridin-1-yl)-2H-1-benzopyran, m.p. 245° C.;

6-cyano-2,2-dimethyl-3-(N-hydroxyacetamido)methyl-4-(2-oxo-1,2-dihydropyridin-1-yl)-2H-1-benzopyran, m.p. 220° C.;

6-pentafluoroethyl-2,2-dimethyl-3-(N-hydroxyacetamido)methyl-4-(2-oxo-1,2-dihydropyridin-1-yl)-2H-1-benzopyran, m.p. 152° C.;

6-bromo-2,2-dimethyl-3-(N-hydroxyacetamido)methyl-4-(2-oxo-1,2-dihydropyridin-1-yl)-2H-1-benzopyran, m.p. 218° C.;

6-chloro-2,2-dimethyl-3-(N-hydroxyacetamido)methyl-4-(2-oxo-1,2-dihydropyridin-1-yl)-2H-1-benzopyran, m.p. 191° C.;

2,2-dimethyl-3-(N-hydroxyacetamido)methyl-4-(2-oxo-1,2-dihydropyridin-1-yl)-2H-1-benzopyran, m.p. 184° C.; and 6-bromo-2,2-dimethyl-3-(N-hydroxypropionamido)methyl-4-(2-oxo-1,2-dihydropyridin-1-yl)-2H-1-benzopyran, m.p. 218° C.

C. Preparation of Formula (I) where $R^1$ and $R^2$ are methyl, $R^5$ and $R^6$ are hydrogen, and $R^9$ is $COR^{12}$, varying $R^3$, $R^4$, $R^8$, and $R^{12}$ In a similar manner, optionally replacing 6-tri fluoromethyl-2,2-dimethyl-3-(hydroxyamino)methyl-4-(2-oxo-1,2-dihydropyridin-1-yl)-2H-1-benzopyran with an appropriate compound of Formula (IA), prepared, for example, as shown in Examples 1 and 2, and optionally replacing acetyl chloride by the appropriate acyl halide of the formula $R^{12}COCl$ or $R^{12}COBr$, where $R^{12}$ is lower alkyl, and following the procedure of Example 7A above, those compounds of Formula (I) where $R^{12}$ is lower alkyl as set forth in Example 5 are obtained.

EXAMPLE 8

Preparation of Compounds of Formula (I) wherein $R^9$ is $CO_2R^{10}$

A. Preparation of Formula (I) where $R^3$ is nitro, $R^1$ and $R^2$ are methyl, $R^5$ and $R^6$ are hydrogen, $R^4$ is 2-oxo-1,2-dihydropyridin-1-yl, $R^8$ is hydrogen and $R^9$ is $CO_2R^{10}$, where $R^{10}$ is methyl To a solution of 6-nitro-2,2-dimethyl-3-aminomethyl-4-(2-oxo-1,2-dihydropyridin-1-yl)-2H-1-benzopyran (0.53 g, 1.53 mmol) and triethylamine (0.25 ml, 1.80 mmol) in dichloromethane (10 ml) at room temperature was added methyl chloroformate (0.14 ml, 1.80 mmol). The solution was stirred for 2 hours and then water added. The organic layer was separated, dried and evaporated to give a crude product, which was crystallized from ether. The crystalline material was then purified by chromatography on silica gel, eluting with acetone/dichloromethane (20/80) to give 0.33 g of 6-nitro-2,2-dimethyl-3-(methoxycarbonylamino)methyl-4-(2-oxo-1,2-dihydropyridin-1-yl)-2H-1-benzopyran, m.p. 199° C.

B. Preparation of Formula (I) where $R^1$ and $R^2$ are methyl, $R^5$ and $R^6$ are hydrogen, $R^3$ is bromo, $R^8$ is hydroxy, $R^9$ is $CO_2R^{10}$, and $R^{10}$ is methyl In a similar manner, but optionally replacing 6-nitro-2,2-dimethyl-3-aminomethyl-4-(2-oxo-1,2-dihydropyridin-1-yl)-2H-1-benzopyran with an appropriate compound of formula Formula (IA), prepared as shown in Example 2, and following the procedure of Example 8A above, the following compound of Formula (I) was prepared:

6-bromo-2,2-dimethyl-3-(methoxycarbonylamino)-methyl-4-(2-oxo-1,2-dihydropyridin-1-yl)-2H-1-benzopyran, m.p. 229° C.

C. Preparation of Formula (I) where $R^1$ and $R^2$ are methyl, $R^5$ and $R^6$ are hydrogen, $CO_2R^{10}$, varying $R^3$, $R^4$, $R^8$, $R^9$ and $R^{10}$ In a similar manner, but optionally replacing 6-nitro-2,2-dimethyl-3-aminomethyl-4-(2-oxo-1,2-dihydropyridin-1-yl)-2H-1-benzopyran with an appropriate compound of Formula (15) or Formula (IA), prepared, for example, as shown in Preparation 17 or Examples 1 and 2, and optionally replacing methyl chloroformate with a lower alkyl chloroformate of formula $ClCO_2R^{10}$, and following the procedure of Example 8A above, the following compounds of Formula (I) are prepared:

6-nitro-2,2-dimethyl-3-(ethoxycarbonylamino)methyl-4-(2-oxo-1,2-dihydropyridin-1-yl)-2H-1-benzopyran;

6-nitro-2,2-dimethyl-3-(N-methylmethoxycarbonylamino)methyl-4-(2-oxo-1,2-dihydropyridin-1-yl)-2H-1-benzopyran;

6-cyano-2,2-dimethyl-3-(methoxycarbonylamino)methyl-4-(2-oxo-1,2-dihydropyridin-1-yl)-2H-1-benzopyran;

6-cyano-2,2-dimethyl-3-(ethoxycarbonylamino)methyl-4-(2-oxo-1,2-dihydropyridin-1-yl)-2H-1-benzopyran;

6-cyano-2,2-dimethyl-3-(N-methylmethoxycarbonylamino)methyl-4-(2-oxo-1,2-dihydropyridin-1-yl)-2H-1-benzopyran;

6-trifluoromethyl-2,2-dimethyl-3-(methoxycarbonylamino)methyl-4-(2-oxo-1,2-dihydropyridin-1-yl)-2H-1-benzopyran;

6-trifluoromethyl-2,2-dimethyl-3-(ethoxycarbonylamino)methyl-4-(2-oxo-1,2-dihydropyridin-1-yl)-2H-1-benzopyran;

6-trifluoromethyl-2,2-dimethyl-3-(N-methylmethoxycarbonylamino)methyl-4-(2-oxo-1,2-dihydropyridin-1-yl)-2H-1-benzopyran;

6-pentafluoroethyl-2,2-dimethyl-3-(methoxycarbonylamino)methyl-4-(2-oxo-1,2-dihydropyridin-1-yl)-2H-1-benzopyran;

6-pentafluoroethyl-2,2-dimethyl-3-(ethoxycarbonylamino)methyl-4-(2-oxo-1,2-dihydropyridin-1-yl)-2H-1-benzopyran;

6-pentafluoroethyl-2,2-dimethyl-3-(N-methylmethoxycarbonylamino)methyl-4-(2-oxo-1,2-dihydropyridin-1-yl)-2H-1-benzopyran;

6-nitro-2,2-dimethyl-3-(methoxycarbonylamino)methyl-4-(2-oxopyrrolidin-1-yl)-2H-1-benzopyran;

6-nitro-2,2-dimethyl-3-(ethoxycarbonylamino)methyl-4-(2-oxopyrrolidin-1-yl)-2H-1-benzopyran;

6-nitro-2,2-dimethyl-3-(N-methylmethoxycarbonylamino)methyl-4-(2-oxopyrrolidin-1-yl)-2H-1-benzopyran;

6-cyano-2,2-dimethyl-3-(methoxycarbonylamino)methyl-4-(2-oxopyrrolidin-1-yl)-2H-1-benzopyran;

6-cyano-2,2-dimethyl-3-(ethoxycarbonylamino)methyl-4-(2-oxopyrrolidin-1-yl)-2H-1-benzopyran;

6-cyano-2,2-dimethyl-3-(N-methylmethoxycar-
   bonylamino)methyl-4-(2-oxopyrrolidin-1-yl)-2H-1-
   benzopyran;
6-trifluoromethyl-2,2-dimethyl-3-(methoxycar-
   bonylamino)methyl-4-(2-oxopyrrolidin-1-yl)-2H-1-
   benzopyran;
6-trifluoromethyl-2,2-dimethyl-3-(ethoxycar-
   bonylamino)methyl-4-(2-oxopyrrolidin-1-yl)-2H-1-
   benzopyran;
6-trifluoromethyl-2,2-dimethyl-3-(N-methylmethox-
   ycarbonylamino)methyl-4-(2-oxopyrrolidin-1-yl)-2H-
   1-benzopyran;
6-pentafluoroethyl-2,2-dimethyl-3-(methoxycar-
   bonylamino)methyl-4-(2-oxopyrrolidin-1-yl)-2H-1-
   benzopyran;
6-pentafluoroethyl-2,2-dimethyl-3-(ethoxycar-
   bonylamino)methyl-4-(2-oxopyrrolidin-1-yl)-2H-1-
   benzopyran;
6-pentafluoroethyl-2,2-dimethyl-3-(N-methylmethox-
   ycarbonylamino)methyl-4-(2-oxopyrrolidin-1-yl)-2H-
   1-benzopyran;
6-nitro-2,2-dimethyl-3-(methoxycarbonylamino)meth-
   yl-4-(1-oxo-isoindolin-2-yl)-2H-1-benzopyran;
6-nitro-2,2-dimethyl-3-(ethoxycarbonylamino)methyl-
   4-(1-oxo-isoindolin-2-yl)-2H-1-benzopyran;
6-nitro-2,2-dimethyl-3-(N-methylmethoxycar-
   bonylamino)methyl-4-(1-oxo-isoindolin-2-yl)-2H-1-
   benzopyran;
6-cyano-2,2-dimethyl-3-(methoxycarbonylamino)meth-
   yl-4-(1-oxo-isoindolin-2-yl)-2H-1-benzopyran;
6-cyano-2,2-dimethyl-3-(ethoxycarbonylamino)methyl-
   4-(1-oxo-isoindolin-2-yl)-2H-1-benzopyran;
6-cyano-2,2-dimethyl-3-(N-methylmethoxycar-
   bonylamino)methyl-4-(1-oxo-isoindolin-2-yl)-2H-1-
   benzopyran;
6-trifluoromethyl-2,2-dimethyl-3-(methoxycar-
   bonylamino)methyl-4-(1-oxo-isoindolin-2-yl)-2H-1-
   benzopyran;
6-trifluoromethyl-2,2-dimethyl-3-(ethoxycar-
   bonylamino)methyl-4-(1-oxo-isoindolin-2-yl)-2H-1-
   benzopyran;
6-trifluoromethyl-2,2-dimethyl-3-(N-methylmethox-
   ycarbonylamino)methyl-4-(1-oxo-isoindolin-2-yl)-
   2H-1-benzopyran;
6-pentafluoroethyl-2,2-dimethyl-3-(methoxycar-
   bonylamino)methyl-4-(1-oxo-isoindolin-2-yl)-2H-1-
   benzopyran;
6-pentafluoroethyl-2,2-dimethyl-3-(ethoxycar-
   bonylamino)methyl-4-(1-oxo-isoindolin-2-yl)-2H-1-
   benzopyran; and
6-pentafluoroethyl-2,2-dimethyl-3-(N-methylmethox-
   ycarbonylamino)methyl-4-(1-oxo-isoindolin-2-yl)-
   2H-1-benzopyran.

EXAMPLE 9

Preparation of Compounds of Formula (I) wherein $R^9$ is $CONHR^{12}$

A. Preparation of Formula (I) where $R^3$ is nitro, $R^1$ and $R^2$ are methyl, $R^5$ and $R^6$ are hydrogen, $R^4$ is 2-oxo-1,2-dihydropyridin-1-yl, $R^8$ is hydrogen and $R^9$ is $CONHR^{12}$, where $R^{12}$ is ethyl A solution of 6-nitro-2,2-dimethyl-3-aminomethyl-4-(2-oxo-1,2-dihydropyridin-1-yl)-2H-1-benzopyran (0.5 g, 1.53 mmol) in dichloromethane (10 ml) was stirred with ethyl isocyanate (0.12 ml, 1.53 mmol) at room temperature for two hours. Water was added and the organic phase separated, dried and evaporated to give crude product, which was chromatographed on silica gel, eluting with dichloromethane/methanol (95/5) to give 0.34 g of 6-nitro-2,2-dimethyl-3-(N'-ethylureido)-methyl-4-(2-oxo-1,2-dihydropyridin-1-yl)-2H-1-benzopyran, m.p. 197° C.

B. Preparation of Formula (I) where $R^3$ is bromo, $R^1$ and $R^2$ are methyl, $R^5$ and $R^6$ are hydrogen, $R^4$ is 2-oxo-1,2-dihydropyridin-1-yl, $R^8$ is hydroxy and $R^9$ is $CONHR^{12}$, where $R^{12}$ is hydrogen To a solution of 6-bromo-2,2-dimethyl-3-(hydroxyamino)methyl-4-(2-oxo-1,2-dihydropyridin-1-yl)-2H-1-benzopyran (0.300 g, 0.0795 mol) in tetrahydrofuran was added dropwise trimethylsilyl isocyanate (0.22 ml, 0.18 g, 0.0016 mol) at room temperature under nitrogen. The reaction mixture was stirred overnight at room temperature. Water and dichloromethane were added. The organic layer was separated, dried and evaporated to give crude product which was chromatographed on silica gel, eluting with dichloromethane/methanol (90/10) to afford 0.24 g (72%) of 6-bromo-2,2-dimethyl-3-(N-hydroxyureido)methyl-4-(2-oxo-1,2-dihydropyridin-1-yl)-2H-1-benzopyran, m.p. 216° C.

C. Preparation of Formula (I) where $R^1$ and $R^2$ are methyl, $R^5$ and $R^6$ are hydrogen, and $R^9$ is $CONHR^{12}$, varying $R^3$, $R^4$, $R^8$ and $R^{12}$ In a similar manner as described in Example 9A, but optionally replacing 6-nitro-2,2-dimethyl-3-aminomethyl-4-(2-oxo-1,2-dihydropyridin-1-yl)-2H-1-benzopyran with an appropriate compound of Formula (15) or Formula (IA), prepared, for example, as shown in Preparation 17 or Examples 1 and 2, and optionally replacing ethyl isocyanate with an appropriate lower alkyl isocyanate of the formula $R^{12}NCO$, and following the procedure of Example 9A above, the following compounds of Formula (I) are obtained:
6-nitro-2,2-dimethyl-3-(N'-methylureido)methyl-4-(2-
   oxo-1,2-dihydropyridin-1-yl)-2H-1-benzopyran;
6-nitro-2,2-dimethyl-3-(N-methyl-N'-ethylureido)meth-
   yl-4-(2-oxo-1,2-dihydropyridin-1-yl)-2H-1-benzopy-
   ran;
6-cyano-2,2-dimethyl-3-(N'-methylureido)methyl-4-(2-
   oxo-1,2-dihydropyridin-1-yl)-2H-1-benzopyran;
6-cyano-2,2-dimethyl-3-(N'-ethylureido)methyl-4-(2-
   oxo-1,2-dihydropyridin-1-yl)-2H-1-benzopyran;
6-cyano-2,2-dimethyl-3-(N-methyl-N'-ethylureido)-
   methyl-4-(2-oxo-1,2-dihydropyridin-1-yl)-2H-1-ben-
   zopyran;
6-trifluoromethyl-2,2-dimethyl-3-(N'-methylureido)-
   methyl-4-(2-oxo-1,2-dihydropyridin-1-yl)-2H-1-ben-
   zopyran;
6-trifluoromethyl-2,2-dimethyl-3-(N'-ethylureido)meth-
   yl-4-(2-oxo-1,2-dihydropyridin-1-yl)-2H-1-benzopy-
   ran;
6-trifluoromethyl-2,2-dimethyl-3-(N-methyl-N'-
   ethylureido)methyl-4-(2-oxo-1,2-dihydropyridin-1-
   yl)-2H-1-benzopyran;
6-pentafluoroethyl-2,2-dimethyl-3-(N'-methylureido)-
   methyl-4-(2-oxo-1,2-dihydropyridin-1-yl)-2H-1-ben-
   zopyran;
6-pentafluoroethyl-2,2-dimethyl-3-(N'-ethylureido)-
   methyl-4-(2-oxo-1,2-dihydropyridin-1-yl)-2H-1-ben-
   zopyran;
6-pentafluoroethyl-2,2-dimethyl-3-(N-methyl-N'-
   ethylureido)methyl-4-(2-oxo-1,2-dihydropyridin-1-
   yl)-2H-1-benzopyran;
6-nitro-2,2-dimethyl-3-(N'-methylureido)methyl-4-(2-
   oxopyrrolidin-1-yl)-2H-1-benzopyran;
6-nitro-2,2-dimethyl-3-(N'-ethylureido)methyl-4-(2-
   oxopyrrolidin-1-yl)-2H-1-benzopyran;

6-nitro-2,2-dimethyl-3-(N-methyl-N'-ethylureido)methyl-4-(2-oxopyrrolidin-1-yl)-2H-1-benzopyran;
6-cyano-2,2-dimethyl-3-(N'-methylureido)methyl-4-(2-oxopyrrolidin-1-yl)-2H-1-benzopyran;
6-cyano-2,2-dimethyl-3-(N'-ethylureido)methyl-4-(2-oxopyrrolidin-1-yl)-2H-1-benzopyran;
6-cyano-2,2-dimethyl-3-(N-methyl-N'-ethylureido)methyl-4-(2-oxopyrrolidin-1-yl)-2H-1-benzopyran;
6-trifluoromethyl-2,2-dimethyl-3-(N'-methylureido)methyl-4-(2-oxopyrrolidin-1-yl)-2H-1-benzopyran;
6-trifluoromethyl-2,2-dimethyl-3-(N'-ethylureido)methyl-4-(2-oxopyrrolidin-1-yl)-2H-1-benzopyran;
6-trifluoromethyl-2,2-dimethyl-3-(N-methyl-N'-ethylureido)methyl-4-(2-oxopyrrolidin-1-yl)-2H-1-benzopyran;
6-pentafluoroethyl-2,2-dimethyl-3-(N'-methylureido)methyl-4-(2-oxopyrrolidin-1-yl)-2H-1-benzopyran;
6-pentafluoroethyl-2,2-dimethyl-3-(N'-ethylureido)methyl-4-(2-oxopyrrolidin-1-yl)-2H-1-benzopyran;
6-pentafluoroethyl-2,2-dimethyl-3-(N-methyl-N'-ethylureido)methyl-4-(2-oxopyrrolidin-1-yl)-2H-1-benzopyran;
6-nitro-2,2-dimethyl-3-(N'-methylureido)methyl-4-(1-oxo-isoindolin-2-yl)-2H-1-benzopyran;
6-nitro-2,2-dimethyl-3-(N'-ethylureido)methyl-4-(1-oxo-isoindolin-2-yl)-2H-1-benzopyran;
6-nitro-2,2-dimethyl-3-(N-methyl-N'-ethylureido)methyl-4-(1-oxo-isoindolin-2-yl)-2H-1-benzopyran;
6-cyano-2,2-dimethyl-3-(N'-methylureido)methyl-4-(1-oxo-isoindolin-2-yl)-2H-1-benzopyran;
6-cyano-2,2-dimethyl-3-(N'-ethylureido)methyl-4-(1-oxo-isoindolin-2-yl)-2H-1-benzopyran;
6-cyano-2,2-dimethyl-3-(N-methyl-N'-ethylureido)methyl-4-(1-oxo-isoindolin-2-yl)-2H-1-benzopyran;
6-trifluoromethyl-2,2-dimethyl-3-(N'-methylureido)methyl-4-(1-oxo-isoindolin-2-yl)-2H-1-benzopyran;
6-trifluoromethyl-2,2-dimethyl-3-(N'-ethylureido)methyl-4-(1-oxo-isoindolin-2-yl)-2H-1-benzopyran;
6-trifluoromethyl-2,2-dimethyl-3-(N-methyl-N'-ethylureido)methyl-4-(1-oxo-isoindolin-2-yl)-2H-1-benzopyran;
6-pentafluoroethyl-2,2-dimethyl-3-(N'-methylureido)methyl-4-(1-oxo-isoindolin-2-yl)-2H-1-benzopyran;
6-pentafluoroethyl-2,2-dimethyl-3-(N'-ethylureido)methyl-4-(1-oxo-isoindolin-2-yl)-2H-1-benzopyran; and
6-pentafluoroethyl-2,2-dimethyl-3-(N-methyl-N'-ethylureido)methyl-4-(1-oxo-isoindolin-2-yl)-2H-1-benzopyran.

EXAMPLE 10

Preparation of Compounds of Formula (I) wherein $R^9$ is $CSNHR^{12}$

A. Preparation of Formula (I) where $R^3$ is nitro, $R^1$ and $R^2$ are methyl, $R^5$ and $R^6$ are hydrogen, $R^4$ is 2-oxo-1,2-dihydropyridin-1-yl, $R^8$ is hydrogen and $R^9$ is $CSNHR^{12}$, where $R^{12}$ is methyl A solution of 6-nitro-2,2-dimethyl-3-aminomethyl-4-(2-oxo-1,2-dihydropyridin-1-yl)-2H-1-benzopyran (0.5 g, 1.53 mmol) in dichloromethane (10 ml) and methyl isothiocyanate (0.11 g, 1.5 mmol) was stirred at room temperature for twenty six hours. The solvent was evaporated, and the residue washed with diethyl ether to give 0.34 g of 6-nitro-2,2-dimethyl-3-(N'-methylthioureido)-methyl-4-(2-oxo-1,2-dihydropyridin-1-yl)-2H-1-benzopyran, m.p. 225° C.

B. Preparation of Formula (I) where $R^3$ is bromo, $R^1$ and $R^2$ are methyl, $R^5$ and $R^6$ are hydrogen, $R^4$ is 2-oxo-1,2-dihydropyridin-1-yl, $R^8$ is hydroxy and $R^9$ is $CSNHR^{12}$, where $R^{12}$ is hydrogen To a solution of 6-bromo-2,2-dimethyl-3-(hydroxyamino)methyl-4-(2-oxo-1,2-dihydropyridin-1-yl)-2H-1-benzopyran in tetrahydrofuran was added dropwise trimethylsilyl isothiocyanate at room temperature. The reaction mixture was stirred at room temperature for two hours. Water was added, and the organic layer separated, dried and evaporated. The residue was triturated with diethyl ether to give 0.18 g of 6-bromo-2,2-dimethyl-3-(N-hydroxythioureido)methyl-4-(2-oxo-1,2-dihydropyridin-1-yl)-2H-1-benzopyran, m.p. 219° C.

C. Preparation of Formula (I) where $R^1$ and $R^2$ are methyl, $R^5$ and $R^6$ are hydrogen, and $R^9$ is $CSNHR^{12}$, varying $R^3$, $R^4$, $R^8$ and $R^{12}$ In a similar manner as described in Example 10A, but optionally replacing 6-nitro-2,2-dimethyl-3-aminomethyl-4-(2-oxo-1,2-dihydropyridin-1-yl)-2H-1-benzopyran with an appropriate compound of Formula (15) or Formula (IA), prepared, for example, as shown in Preparation 17 or Examples 1 and 2, and optionally replacing methyl isothiocyanate with an appropriate lower alkyl isothiocyanate of the formula $R^{12}NCS$, and following the procedure of Example 10A above, the following compounds of Formula (I) are obtained:

6-nitro-2,2-dimethyl-3-(N'-methylthioureido)methyl-4-(2-oxo-1,2-dihydropyridin-1-yl)-2H-1-benzopyran;
6-nitro-2,2-dimethyl-3-(N-methyl-N'-ethylthioureido)-methyl-4-(2-oxo-1,2-dihydropyridin-1-yl)-2H-1-benzopyran;
6-cyano-2,2-dimethyl-3-(N'-methylthioureido)methyl-4-(2-oxo-1,2-dihydropyridin-1-yl)-2H-1-benzopyran;
6-cyano-2,2-dimethyl-3-(N'-ethylthioureido)methyl-4-(2-oxo-1,2-dihydropyridin-1-yl)-2H-1-benzopyran;
6-cyano-2,2-dimethyl-3-(N-methyl-N'-ethylthioureido)-methyl-4-(2-oxo-1,2-dihydropyridin-1-yl)-2H-1-benzopyran;
6-trifluoromethyl-2,2-dimethyl-3-(N'-methylthioureido)methyl-4-(2-oxo-1,2-dihydropyridin-1-yl)-2H-1-benzopyran;
6-trifluoromethyl-2,2-dimethyl-3-(N'-ethylthioureido)-methyl-4-(2-oxo-1,2-dihydropyridin-1-yl)-2H-1-benzopyran;
6-trifluoromethyl-2,2-dimethyl-3-(N-methyl-N'-ethylthioureido)methyl-4-(2-oxo-1,2-dihydropyridin-1-yl)-2H-1-benzopyran;
6-pentafluoroethyl-2,2-dimethyl-3-(N'-methylthioureido)methyl-4-(2-oxo-1,2-dihydropyridin-1-yl)-2H-1-benzopyran;
6-pentafluoroethyl-2,2-dimethyl-3-(N'-ethylthioureido)methyl-4-(2-oxo-1,2-dihydropyridin-1-yl)-2H-1-benzopyran;
6-pentafluoroethyl-2,2-dimethyl-3-(N-methyl-N'-ethylthioureido)methyl-4-(2-oxo-1,2-dihydropyridin-1-yl)-2H-1-benzopyran;
6-nitro-2,2-dimethyl-3-(N'-methylthioureido)methyl-4-(2-oxopyrrolidin-1-yl)-2H-1-benzopyran;
6-nitro-2,2-dimethyl-3-(N'-ethylthioureido)methyl-4-(2-oxopyrrolidin-1-yl)-2H-1-benzopyran;
6-nitro-2,2-dimethyl-3-(N-methyl-N'-ethylthioureido)-methyl-4-(2-oxopyrrolidin-1-yl)-2H-1-benzopyran;
6-cyano-2,2-dimethyl-3-(N'-methylthioureido)methyl-4-(2-oxopyrrolidin-1-yl)-2H-1-benzopyran;
6-cyano-2,2-dimethyl-3-(N'-ethylthioureido)methyl-4-(2-oxopyrrolidin-1-yl)-2H-1-benzopyran;
6-cyano-2,2-dimethyl-3-(N-methyl-N'-ethylthioureido)-methyl-4-(2-oxopyrrolidin-1-yl)-2H-1-benzopyran;

6-trifluoromethyl-2,2-dimethyl-3-(N'-methylthioureido)methyl-4-(2-oxopyrrolidin-1-yl)-2H-1-benzopyran;
6-trifluoromethyl-2,2-dimethyl-3-(N'-ethylthioureido)methyl-4-(2-oxopyrrolidin-1-yl)-2H-1-benzopyran;
6-trifluoromethyl-2,2-dimethyl-3-(N-methyl-N'-ethylthioureido)methyl-4-(2-oxopyrrolidin-1-yl)-2H-1-benzopyran;
6-pentafluoroethyl-2,2-dimethyl-3-(N'-methylthioureido)methyl-4-(2-oxopyrrolidin-1-yl)-2H-1-benzopyran;
6-pentafluoroethyl-2,2-dimethyl-3-(N'-ethylthioureido)methyl-4-(2-oxopyrrolidin-1-yl)-2H-1-benzopyran;
6-pentafluoroethyl-2,2-dimethyl-3-(N-methyl-N'-ethylthioureido)methyl-4-(2-oxopyrrolidin-1-yl)-2H-1-benzopyran;
6-nitro-2,2-dimethyl-3-(N'-methylthioureido)methyl-4-(1-oxo-isoindolin-2-yl)-2H-1-benzopyran;
6-nitro-2,2-dimethyl-3-(N'-ethylthioureido)methyl-4-(1-oxo-isoindolin-2-yl)-2H-1-benzopyran;
6-nitro-2,2-dimethyl-3-(N-methyl-N'-ethylthioureido)methyl-4-(1-oxo-isoindolin-2-yl)-2H-1-benzopyran;
6-cyano-2,2-dimethyl-3-(N'-methylthioureido)methyl-4-(1-oxo-isoindolin-2-yl)-2H-1-benzopyran;
6-cyano-2,2-dimethyl-3-(N'-ethylthioureido)methyl-4-(1-oxo-isoindolin-2-yl)-2H-1-benzopyran;
6-cyano-2,2-dimethyl-3-(N-methyl-N'-ethylthioureido)methyl-4-(1-oxo-isoindolin-2-yl)-2H-1-benzopyran;
6-trifluoromethyl-2,2-dimethyl-3-(N'-methylthioureido)methyl-4-(1-oxo-isoindolin-2-yl)-2H-1-benzopyran;
6-trifluoromethyl-2,2-dimethyl-3-(N'-ethylthioureido)methyl-4-(1-oxo-isoindolin-2-yl)-2H-1-benzopyran;
6-trifluoromethyl-2,2-dimethyl-3-(N-methyl-N'-ethylthioureido)methyl-4-(1-oxo-isoindolin-2-yl)-2H-1-benzopyran;
6-pentafluoroethyl-2,2-dimethyl-3-(N'-methylthioureido)methyl-4-(1-oxo-isoindolin-2-yl)-2H-1-benzopyran;
6-pentafluoroethyl-2,2-dimethyl-3-(N'-ethylthioureido)methyl-4-(1-oxo-isoindolin-2-yl)-2H-1-benzopyran; and
6-pentafluoroethyl-2,2-dimethyl-3-(N-methyl-N'-ethylthioureido)methyl-4-(1-oxo-isoindolin-2-yl)-2H-1-benzopyran.

EXAMPLE 11

Preparation of Compounds of Formula (I) wherein $R^9$ is $SO_2R^{10}$

A. Preparation of Formula (I) where $R^3$ is nitro, $R^1$ and $R^2$ are methyl, $R^5$ and $R^6$ are hydrogen, $R^4$ is 2-oxo-1,2-dihydropyridin-1-yl, $R^8$ is hydrogen and $R^9$ is $SO_2R^{10}$, where $R^{10}$ is methyl To a solution of 6-nitro-2,2-dimethyl-3-aminomethyl-4-(2-oxo-1,2-dihydropyridin-1-yl)-2H-1-benzopyran (0.43 g, 1.31 mmol) and triethylamine (0.22 ml, 1.58 mmol) in dichloromethane (15 ml) was added methanesulfonylchloride (0.12 ml, 1.55 mol). The solution was stirred at room temperature for four hours, and then water was added. The organic phase was separated and evaporated under reduced pressure. The residue was washed with diethyl ether, affording 0.3 g of 6-nitro-2,2-dimethyl-3-(methanesulfonamido)methyl-4-(2-oxo-1,2-dihydropyridin-1-yl)-2H-1-benzopyran, m.p. 195° C.

B. Preparation of Formula (I) where $R^1$ and $R^2$ are methyl, $R^5$ and $R^6$ are hydrogen, and $R^9$ is $SO_2R^{10}$, varying $R^3$, $R^4$, $R^8$ and $R^{10}$ In a similar manner, but optionally replacing 6-nitro-2,2-dimethyl-3-aminomethyl-4-(2-oxo-1,2-dihydropyridin-1-yl)-2H-1-benzopyran with an appropriate compound of Formula (15) or Formula (IA), prepared, for example, as shown in Preparation 17 or Examples 1 and 2, and optionally replacing methanesulfonyl chloride with a compound of the formula $R^{10}SO_2Cl$ or $R^{10}SO_2Br$, where $R^{10}$ is lower alkyl, and following the procedure of Example 11A above, the following compounds of Formula (I) are prepared:

6-cyano-2,2-dimethyl-3-(methanesulfonamido)methyl-4-(2-oxo-1,2-dihydropyridin-1-yl)-2H-1-benzopyran;
6-trifluoromethyl-2,2-dimethyl-3-(methanesulfonamido)methyl-4-(2-oxo-1,2-dihydropyridin-1-yl)-2H-1-benzopyran;
6-pentafluoroethyl-2,2-dimethyl-3-(methanesulfonamido)methyl-4-(2-oxo-1,2-dihydropyridin-1-yl)-2H-1-benzopyran;
6-nitro-2,2-dimethyl-3-(methanesulfonamido)methyl-4-(2-oxopyrrolidin-1-yl)-2H-1-benzopyran;
6-cyano-2,2-dimethyl-3-(methanesulfonamido)methyl-4-(2-oxopyrrolidin-1-yl)-2H-1-benzopyran;
6-trifluoromethyl-2,2-dimethyl-3-(methanesulfonamido)methyl-4-(2-oxopyrrolidin-1-yl)-2H-1-benzopyran;
6-pentafluoroethyl-2,2-dimethyl-3-(methanesulfonamido)methyl-4-(2-oxopyrrolidin-1-yl)-2H-1-benzopyran;
6-nitro-2,2-dimethyl-3-(methanesulfonamido)methyl-4-(1-oxo-isoindolin-2-yl)-2H-1-benzopyran;
6-cyano-2,2-dimethyl-3-(methanesulfonamido)methyl-4-(1-oxo-isoindolin-2-yl)-2H-1-benzopyran;
6-trifluoromethyl-2,2-dimethyl-3-(methanesulfonamido)methyl-4-(1-oxo-isoindolin-2-yl)-2H-1-benzopyran; and
6-pentafluoroethyl-2,2-dimethyl-3-(methanesulfonamido)methyl-4-(1-oxo-isoindolin-2-yl)-2H-1-benzopyran.

EXAMPLE 12

Alternative Preparation of compounds of Formula (I) wherein $R^9$ is $CO_2R^{10}$, $CONR^{11}R^{12}$ or $COR^{12}$ A. Preparation of Formula (I) where $R^3$ is nitro, $R^1$ and $R^2$ are methyl, $R^5$ and $R^6$ are hydrogen, $R^4$ is 2-oxo-1,2-dihydropyridin-1-yl, $R^8$ is hydrogen and $R^9$ is $COR^{12}$, where $R^{12}$ is trifluoromethyl A solution of 6-nitro-2,2-dimethyl-3-hydroxy-3,4-dihydro-3-(trifluoroacetamido)methyl-4-(2-oxo-1,2-dihydropyridin-1-yl)-2H-1-benzopyran (0.5 g, 1.13 mmol) in tetrahydrofuran (20 ml) containing sodium hydride (80%, 0.034 g, 1.13 mol) was refluxed for one hour. Water and ethyl acetate were added to the cooled solution and the organic phase was separated and evaporated under reduced pressure. The residue was chromatographed on silica gel, eluting with dichloromethane/acetone (95/5), to give 0.13 g of 6-nitro-2,2-dimethyl-3-(trifluoroacetamido)methyl-4-(2-oxo-1,2-dihydropyridin-1-yl)-2H-1-benzopyran, m.p. 189° C.

B. Preparation of Formula (I) where $R^1$ and $R^2$ are methyl, $R^5$ and $R^6$ are hydrogen, and $R^9$ is $CO_2R^{10}$, $CONR^{11}R^{12}$ or $COR^{12}$, varying $R^3$, $R^4$, $R^8$, $R^{10}$, $R^{11}$ and $R^{12}$ In a similar manner, optionally replacing 6-nitro-2,2-dimethyl-3-hydroxy-3,4-dihydro-3-(trifluoroacetamido)methyl-4-(2-oxo-1,2-dihydropyridin- 1-yl)-2H-1-benzopyran with an appropriate compound of Formula (19), prepared, for example, as shown in Preparation 21, and following the procedure of Example 12A above, the compounds of Formula (I) as set forth in Examples 1–9 are obtained.

EXAMPLE 13

Preparation of Compounds of Formula (I) wherein $R^4$ is (2-oxopyrrolidin-1-yl) or (1-oxo-isoindolin-2-yl) and $R^9$ is $CO_2R^{10}$, $CONR^{11}R^{12}$ or $COR^{12}$ A. Preparation of Formula (I) where $R^3$ is nitro, $R^1$ and $R^2$ are methyl, $R^5$ and $R^6$ are hydrogen, $R^4$ is 2-oxopyrrolidin-1-yl, $R^8$ is hydrogen and $R^9$ is $COR^{12}$, where $R^{12}$ is methyl A solution containing 6-nitro-3-acetamidomethyl-3,4-dihydro-3,4-epoxy-2,2-dimethyl-2H-1-benzopyran (0.5 g, 1.72 mmol), 2-pyrrolidinone (0.3 g, 3.48 mmol) and Triton B (40% in ethanol, 0.1 ml) in dioxane (10 ml) was heated at 50° C. for eighteen hours. Water and ethyl acetate were added, and the organic phase separated and evaporated under reduced pressure. The residue was chromatographed on silica gel, eluting with dichloromethane/methanol (95/5), to give crude product which on triturating with diethyl ether afforded 0.14 g of 6-nitro-2,2-dimethyl-3-acetamidomethyl-4-(2-oxopyrrolidin-1-yl)-2H-1-benzopyran, m.p. 205° C.

B. Preparation of Formula (I) where $R^3$ is nitro, $R^1$ and $R^2$ are methyl, $R^5$ and $R^6$ are hydrogen, $R^4$ is 1-oxo-isoindolin-2-yl, $R^8$ is hydrogen and $R^9$ is $COR^{12}$, where $R^{12}$ is methyl In a similar manner, replacing 2-pyrrolidinone with 1-oxoisoindole, and following the procedure of Example 13A above, the following compound of Formula (I) was prepared:

6-nitro-2,2-dimethyl-3-acetamidomethyl-4-(1-oxo-isoindolin-2-yl)-2H-1-benzopyran, m.p. 220° C.

C. Preparation of Formula (I) where $R^1$ and $R^2$ are methyl, $R^5$ and $R^6$ are hydrogen, $R^4$ is (2-oxopyrrolidin-1-yl) or (1-oxoisoindolin-2-yl), and $R^9$ is $CO_2R^{10}$, $CONR^{11}R^{12}$, or $COR^{12}$, varying $R^3$, $R^4$, $R^8$, $R^{10}$, $R^{11}$ and $R^{12}$ In a similar manner, optionally replacing 6-nitro-2,2-dimethyl-3-hydroxy-3,4-dihydro-3-(trifluoroacetamido)methyl-4-(2-oxo-1,2-dihydropyridin-1-yl)-2H-1-benzopyran with an appropriate compound of Formula (18), prepared, for example, as shown in Preparation 20, and following the procedure of Example 13A above, the compounds of Formula (I) as set forth in Examples 1–9 are obtained.

EXAMPLE 14

Conversion of Compounds of Formula (I) to a Salt

A. A solution of 6-nitro-2,2-dimethyl-3-(2-hydroxyethylamino)methyl-4-(2-oxo-1,2-dihydropyridin-1-yl)-2H-1-benzopyran (0.44 g, 1.18 mmol) in diethylether was treated with excess ethanolic hydrochloric acid (2M) and the resulting precipitate isolated by filtration, to give 0.36 g of 6-nitro-2,2-dimethyl-3-(2-hydroxyethylamino)methyl-4-(2-oxo-1,2-dihydropyridin-1-yl)-2H-1-benzopyran hydrochloride, m.p. 225° C.

B. Similarly, replacing 6-nitro-2,2-dimethyl-3-(2-hydroxyethylamino)methyl)-4-(2-oxo-1,2-dihydropyridin-1-yl)-2H-1-benzopyran with an appropriate free base of a compound of Formula (I), the corresponding hydrochloride salts are prepared.

EXAMPLE 15

This example illustrates the preparation of representative pharmaceutical compositions for oral administration containing a compound of Formula (I), or a pharmaceutically acceptable salt thereof, e.g. 6-nitro-2,2-dimethyl-3-(acetamido)methyl-4-(2-oxo-1,2-dihydropyridin-1-yl)-2H-1-benzopyran:

| A. Ingredients | % wt./wt. |
| --- | --- |
| Compound of Formula (I) | 20.0% |
| Lactose | 79.5% |
| Magnesium stearate | 0.5% |

The above ingredients are mixed and dispensed into hard-shell gelatin capsules containing 100 mg each, one capsule would approximate a total daily dosage.

| B. Ingredients | % wt./% wt. |
| --- | --- |
| Compound of Formula (I) | 20.0% |
| Magnesium stearate | 0.9% |
| Starch | 8.6% |
| Lactose | 69.6% |
| PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. Ingredients | |
| --- | --- |
| Compound of Formula (I) | 0.1 g |
| Propylene glycol | 20.0 g |
| Polyethylene glycol 400 | 20.0 g |
| Polysorbate 80 | 1.0 g |
| Water | q.s. 100 mL |

The compound of Formula (I), is dissolved in propylene glycol, polyethylene glycol 400 and polysorbate 80. A sufficient quantity of water is then added with stirring to provide 100 mL of the solution which is filtered and bottled.

| D. Ingredients | % wt/wt. |
| --- | --- |
| Compound of Formula (I) | 20.0% |
| Peanut Oil | 78.0% |
| Span 60 | 2.0% |

The above ingredients are melted, mixed and filled into soft elastic capsules.

EXAMPLE 16

This example illustrates the preparation of a representative pharmaceutical formulation for parenteral administration containing a compound of Formula (I), or a pharmaceutically acceptable salt thereof, e.g. 6-nitro-2,2-dimethyl-3-(N-hydroxyacetamido)methyl-4-(2-oxo-1,2-dihydropyridin-1-yl)-2H-1-benzopyran:

| Ingredients | |
| --- | --- |
| Compound of Formula (I) | 0.02 g |
| Propylene glycol | 20.0 g |
| Polyethylene glycol 400 | 20.0 g |
| Polysorbate 80 | 1.0 g |
| 0.9% Saline solution | qs 100 mL |

The compound of Formula (I), e.g., 6-nitro-2,2-dimethyl-3-(N-hydroxyacetamido)methyl-4-(2-oxo-1,2-dihydropyridin-1-yl)-2H-1-benzopyran, is dissolved in propylene glycol, polyethylene glycol 400 and polysorbate 80. A sufficient quantity of 0.9% saline solution is then added with stirring to provide 100 mL of the I.V. solution which is filtered through a 0.2μ membrane filter and packaged under sterile conditions.

EXAMPLE 17

This example illustrates the preparation of a representative pharmaceutical composition in suppository form containing a compound of Formula (I), or a pharmaceutically acceptable salt thereof, e.g. 6-cyano-2,2-dimethyl-3-(N-hydroxyacetamido)methyl-4-(2-oxo-1,2-dihydropyridin-1-yl)-2H-1-benzopyran:

| Ingredients | % wt./wt. |
|---|---|
| Compound of Formula (I) | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 18

This example illustrates the preparation of a representative pharmaceutical formulation for insufflation containing a compound of Formula (I), or a pharmaceutically acceptable salt thereof, e.g. 6-pentafluoro-2,2-dimethyl-3-(N-hydroxyacetamido)methyl-4-(2-oxo-1,2-dihydropyridin-1-yl)-2H-1-benzopyran:

| Ingredients | % wt/wt. |
|---|---|
| Micronized compound of Formula (I) | 1.0% |
| Micronized lactose | 99.0% |

The ingredients are milled, mixed, and packaged in an insufflator equipped with a dosing pump.

EXAMPLE 19

This example illustrates the preparation of a reprensative pharmaceutical formulation in nebulized form containing a compound of Formula (I), or a pharmaceutically acceptable salt thereof, e.g. 6-nitro-2,2-dimethyl-3-(formamido)methyl-4-(2-oxo-1,2-dihydropyridin-1-yl)-2H-1-benzopyran:

| Ingredients | % wt/wt |
|---|---|
| Compound of Formula (I) | 0.005% |
| Water | 89.995% |
| Ethanol | 10.000% |

The compound of Formula (I) is dissolved in ethanol and water. The formulation is then packaged in a nebulizer equipped with a dosing pump.

EXAMPLE 20

This example illustrates the preparation of a representative pharmaceutical formulation in aerosol form containing a compound of Formula (I), or a pharmaceutically acceptable salt thereof, e.g., 6-trifluoromethyl-2,2-dimethyl-3-(N-hydroxyacetamido)methyl-4-(2-oxo-1,2-dihydropyridin-1-yl)-2H-1-benzopyran:

| Ingredients | % wt/wt |
|---|---|
| Compound of Formula (I) | 0.10% |
| Propellant 11/12 | 98.90% |
| Oleic acid | 1.00% |

The compound of Formula (I) is dispersed in oleic acid and the propellants. The resulting mixture is then introduced into an aerosol container fitted with a metering valve.

EXAMPLE 21

This example illustrates the preparation of a representative pharmaceutical formulation for topical application in the eye containing a compound of Formula (I), or a pharmaceutically acceptable salt thereof, e.g., 6-cyano-2,2-dimethyl-3-(N-hydroxyacetamido)methyl-4-(2-oxo-1,2-dihydropyridin-1-yl)-2H-1-benzopyran:

| Ingredients | |
|---|---|
| Compound of Formula (I) | 0.10 g |
| Benzalkonium chloride | 0.01 g |
| Polyethylene glycol 400 | 5.00 g |
| Glycerol | 5.00 g |
| $PO_4H_2Na$ | 1.00 g |
| $PO_4HNa_2$ | 1.00 g |
| NaOH | q.s.p. |
| 0.9% Saline solution | q.s.100 mL |

Benzalkonium chloride, polyethylene glycol 400, $PO_4H_2Na$, $PO_4HNa_2$ are dissolved in 0.9% saline solution. The compound of Formula (I), e.g. 6-cyano-2,2-dimethyl-3-(N-hydroxyacetamido)methyl-4-(2-oxo-1,2-dihydropyridin-1-yl)-2H-1-benzopyran is added to the solution. The solution is neutralized by addition of aqueous solution of sodium hydroxide to obtain an isotonic pH. The solution is filtered through a 0.2μ membrane filter and packaged under sterile conditions. Finally, the preparation is filled in suitable containers for dispensing and autoclaved at 120° C.

EXAMPLE 22

Determination of Smooth Muscle Relaxant Properties (In Vitro Assay)

The smooth muscle relaxant properties of the compounds were evaluated in-vitro, using vascular preparations previously contracted with an appropriate spasmogen, in the following manner:

A. Aortas were quickly removed from rats killed by a blow to the head. The tissue was cleared of connective tissue and cut into rings after removing endothelium by gently rubbing with forceps. These strips were then bathed in Krebs physiological solution at 37° C., and gassed with a mixture of 95% oxygen/5% carbon dioxide under 2 g tension. Sustained contractions were evoked with potassium chloride (20 mM final bath concentration). Contractile tension of the muscle strips was recorded isometrically. Test compounds were added at cumulatively increasing concentrations ($10^{-10}$ to $10^{-5}$M) in water or water with 2-3 drops Tween 80 or 1% alcohol. The maximum reduction in potassium chloride induced-tension was compared for each differing concentration of test compounds used. Results for the compounds of Formula (I) in this assay are evaluated in terms of their $pIC_{50}$ values ($pIC_{50}$ = negative $Log_{10}$[M] compound to cause 50% inhibition of contraction induced by KCl, M being the concentration of the test compound). The results are summarized in the following table:

The compounds of Formula (I) demonstrated positive smooth muscle relaxant properties in this assay.

B. In a similar experiment, compounds of Formula (I) failed to relax rat aortic rings which had been contracted with potassium chloride (40 mM), results thus obtained were consistent with a physiological mechanism involving potassium channel activation.

EXAMPLE 23

Interaction with the Potassium Channel Antagonist Glibenclamide

Aortic rings, free of functional endothelium, from male Spague-Dawley rats (250-300 g) were suspended under a resting tension of 2 g in a Krebs bicarbonate solution maintained at 37° C. and gassed with 95% $O_2$ and 5% $CO_2$ using a modified version of the methods described in *J. Pharm. Exp. Ther.* (1989), vol. 248, pp. 1261-1268. Preparations were contracted by increasing the concentration of $K^+$ ions in the bathing medium to 20 mM by addition of potassium chloride. When the contractile response was stable, the potassium channel antagonist, glibenclamide, or the relevant vehicle (control) was added to the bathing medium and tension recorded during the following 30 minutes. After this incubation period, the tested compounds of Formula (I) were added in increasing cumulative concentrations to obtain concentration-relaxation curves, each successive concentration reaching an apparent maximum before addition of subsequent concentrations. Separate groups of 4-6 preparations were used for each treatment.

The concentration of compound required to evoke a relaxant response equivalent to 50% of the maximum, $pIC_{50}$ (where 100% is equal to return to precontraction baseline) in the presence or absence of glibenclamide and the concentration ratio (CR) were calculated. The antagonistic affinity constants ($pK_B$) for different concentrations of glibenclamide were calculated by the method described by R. F. Furchgott in "The Classification of Adrenoceptors (adrenergic receptors). An evaluation from the standpoint of receptor theory," *Handbook of Experimental Pharmacology* (1972), Vol. 33, pp. 282-335.

The compounds of Formula (I) exhibited smooth muscle relaxant properties which were antagonized by glibenclamide when tested in this assay, and therefore have potassium channel activating properties.

EXAMPLE 24

Determination of Antihypertensive Activity (In Vivo Assay)

The antihypertensive effects of the compounds of Formula (I) were evaluated in spontaneously hypertensive rats (Iffa Credo, aged 18–20 weeks)). The rats were anesthetized with pentobarbital (50 mg/Kg i.p.), and a catheter was implanted into the descending aorta via a femoral artery. The catheter was exteriorized at the back of the neck and sealed with a pin. After surgery the rats were housed in individual cages, and pulsatile aortic blood pressure was measured directly 1-3 days later in groups of 4-8 conscious animals, using a Statham P50 pressure tranducer connected to a Gould S8000 chart recorder. Heart rate was determined by using the pulse pressure to trigger a ratemeter. Rats with mean blood pressure greater than 145 mmHg were considered to be hypertensive.

The test compounds were suspended in 2% Tween 80 vehicle for oral administration. A control group received vehicle (0.5 ml/Kg p.o.) alone. Cardiovascular parameters were recorded at 15, 30, 45 and 60 minutes, and thereafter at hourly intervals for the first 7 hours, then at 24 hours post dosing. Maximum changes in systolic, diastolic and mean blood pressure were measured, as was change in heart rate. Calculations were made of the percentage changes in blood pressure and heart rate with respect to the initial values and vehicle-treated time controls. The duration of the antihypertensive effect was calculated as the time during which the blood pressure value remains significantly lower than the vehicle-treated group. The compounds of Formula (I) demonstrated positive antihypertensive activity in this assay.

EXAMPLE 25

Histamine-induced Bronchospasms in Anesthetised Guinea-pigs (In-Vivo Assay)

The tests were performed on male tricolor guinea-pigs weighing 330–450 g (Cob lab.) using a modified method of Dixon and Brodie (1). The animals were anesthetized with ethyl-carbamate (1-2 g/kg i.p. in two separate injections). Animals received gallamine (1 mg/kg i.v.) to prevent skeletal muscular contractions. A tracheal cannula was inserted and connected to a small animal ventilator (Harvard pump) in order to maintain artificial respiration of the animals. The pump was set at a constant flow rate and frequency (1 ml/100 g, 80 strokes/minute). The variation in airway pressure (equal to airway resistance at constant flow) was monitored by an electromagnetic pressure transducer (Gould, France) fitted to a shunt in the ventilation circuit and connected via an amplifier to a potentiometric recorder (Gould). Bolus doses of histamine (10 mcg/kg) were injected in separate groups of animals via a catheterized jugular vein, at 5 minute intervals until repeatable increases in airway pressure occurred. The compounds to be tested were then administered either:

intravenously at one dose level only and the agonist challenges repeated at 5 minute intervals for 30 minutes, starting 1 minute post-treatment, or directly into the airways in the form of an aerosol.

Following a series of histamine tests, the ventilatory system was connected directly to a medical nebulizer (Devilhiss Pulmo-aid) containing a solution of the test compound. The animals thus received an aerosol of the solution (mean particle size 0.6 mcm) directly into the airways, for a period of 1 to 5 minutes.

The agonist (histamine) challenge was then repeated at 5 minutes intervals for 30 minutes, starting 1 minute post treatment.

The amount of compound administered to the animals is expressed as a given concentration of solution nebulized for a given time (i.e., 125 mcg/ml for 5 minutes).

The inhibition of the bronchospasm induced by the compounds were estimated from the average inflation pressure of the three histamine challenges prior to the compound injection or nebulisation and the inflation pressure obtained thereafter.

The compounds of Formula (I) demonstrated bronchodilating activity in this assay.

EXAMPLE 26

Intraocular Pressure in Rabbits (In-Vivo Assay)

These studies are conducted using young New Zealand albino rabbits (2.0–3.0 kg), according to the method described by L. David Waterbury in *Investigative Ophtalmology and Visual Science* (1990), Vol. 31, pp. 2560–2567. The rabbits should not have previously received topical drugs of any kind. The intraocular pressure (IOP) is measured with a pneumotonometer (Digilab, Bio-Rad) calibrated at the beginning and end of each study by a Digilab calibrator equipped with a membrane sensor. Before the studies, the rabbits are acclimatized to study conditions by removing them from their cages and taking unrecorded measurements after topical administration of the corneal anesthetic proparacaine monohydrochloride (Allergan, Irvine). The rabbits are them randomly assigned into treatment groups of seven animals each. During initial tonometry readings, rabbits with more than a 3 mm Hg IOP difference between eyes are excluded. The basal IOP of the animals used is in a range of 19–25 mm Hg. Compounds are administered (50 μl volume) to one eye, and an equivalent volume of vehicle administered to the contralateral eye, which acts as a control. An additional group of animals receive vehicle in both eyes. The effects of compounds of Formula (I) are compared with both intraocular pressure effects in vehicle-treated rabbits and in animals in which vehicle is administered to the contralateral eye. This second parameter allows assessment of the potential systemic effects. The IOP measurements are made one minute before compound administration and at intervals 1–8 hours thereafter.

In all studies ocular irritation, defined by lid closure and hyperemia are recorded. Dose-response curves are constructed with each synthetic compound. Analysis of variance is done to test for significant effects of treatment. At each time paired data are compared between IOP pressure effect in compound-treated eyes and vehicle-treated controlateral eyes. In addition, the IOP of vehicle-treated eyes of the control group is also compared with the treated eyes. All statistics are analyzed using general linear models.

The compounds of Formula (I) induce a lowering effect on intraocular pressure in this assay, and therefore have antiglaucoma properties.

EXAMPLE 27

Rat model of peripheral vascular ischemia (In-vivo Assay)

This assay is performed on Sprague-Dawley rats, weighing 140–150 g. The rats are anesthetized with pentobarbital (50 mg/kg i.p.), and a silk ligature tied around the left femoral artery at the circumflex iliac artery level using a modification of the methods of Angersbach and Nicholson described in *Naunyn-Schmiedeberg's Arch. Pharmacol* (1988), Vol. 337, pp. 341–346. The animals are allowed to recover for 6 weeks during which time collateral blood vessels develop in the ligated leg. At 6 weeks post-ligature, animals are re-anesthetized with pentobarbital (55 mg/kg i.p.), anesthesia being maintained by addition of pentobarbital (1 mg/kg/hour i.v.), and their temperature kept constant at 37° C. An arterial catheter is inserted in a carotid artery to record blood pressure and heart rate, and a second catheter is positioned in a jugular vein for drugs injection. The skin is cleared from the internal surface of the left and right hind legs and laser doppler probes (Moor Instruments) placed on the internal side of the right and left gastrocnemius muscles to monitor local skeletal muscle red blood cell flux.

Compounds of Formula (I) when infused by the i.v. route of administration in this model induce a progressive increase in flux in the ligated leg.

EXAMPLE 28

Determination of 5-Lipoxygenase Inhibitory Activity (In-Vitro Assay)

This assay was performed on human whole blood.

A mixture of freshly drawn heparinized blood (1 ml) and a solution of the test sample in 2 μl of dimethylsulfoxide (0.01 to 100 μg of test sample per ml) was prepared. The mixture was preincubated at 37° C. for 15 minutes. Calcium ionophore A23187 (2 μl, 25 mM) was added to start the reaction. After incubation at 37° C. for 30 minutes, plasma was separated and analyzed for leukotriene B4 ($LTB_4$) by radioimmune assay, comparing the results to the mean dimethylsulfoxide vehicle control. All assays were performed in duplicate.

The compounds of Formula (I) demonstrated 5-lipoxygenase inhibitory activity in this assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula:

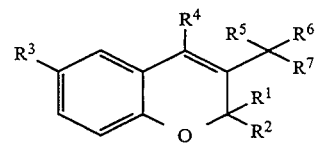

wherein:

$R^1$ and $R^2$ are independently hydrogen or lower alkyl, or when taken together with the carbon to which they are attached are cycloalkyl of 3 to 8 carbon atoms;

$R^3$ is hydrogen, or halo;

$R^4$ is

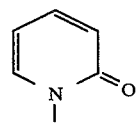

$R^5$ and $R^6$ are independently hydrogen or lower alkyl; and $R^7$ is $-NR^8R^9$, wherein:

$R^8$ is hydrogen; lower alkyl; lower alkoxy; hydroxy; or hydroxy lower alkyl; and $R^9$ is hydrogen; lower alkyl; hydroxy lower alkyl; $-SO_2R^{10}$; $-CO_2R^{10}$; $-C(O)NR^{11}R^{12}$; $-C(S)NR^{11}R^{12}$; or $-C(O)R^{12}$;

wherein:

$R^{10}$ is lower alkyl;

$R^{11}$ is hydrogen or lower alkyl; and $R^{12}$ is hydrogen, lower alkyl, or fluoro lower alkyl;

with the proviso that $R^8$ and $R^9$ cannot both be hydrogen; or a pharmaceutically acceptable salt thereof.

2. The compound of claim 1, wherein $R^5$ and $R^6$ are both hydrogen, or a pharmaceutically acceptable salt thereof.

3. The compound of claim 2, wherein $R^1$ and $R^2$ are both methyl, or a pharmaceutically acceptable salt thereof.

4. The compound of claim 3, wherein $R^8$ is hydroxy, or a pharmaceutically acceptable salt thereof.

5. The compound of claim 4, wherein $R^9$ is hydrogen, lower alkyl, or —C(O)$R^{12}$, or a pharmaceutically acceptable salt thereof.

6. The compound of claim 5, wherein $R^3$ and $R^9$ are both hydrogen, namely 2,2-dimethyl-3-(N-hydroxyamino)methyl-4-(2-oxo-1,2-dihydropyridin-1-yl)-2H-1-benzopyran, or a pharmaceutically acceptable salt thereof.

7. The compound of claim 5, wherein $R^3$ is hydrogen, and $R^9$ is —C(O)$R^{12}$, where $R^{12}$ is methyl, namely 2,2-dimethyl-3-(N-hydroxyacetamido)methyl-4-(2-oxo-1,2-dihydropyridin-1-yl)-2H-1-benzopyran, or a pharmaceutically acceptable salt thereof.

8. The compound of claim 5, wherein $R^3$ is chloro, and $R^9$ is hydrogen, namely 6-chloro-2,2-dimethyl-3-(N-hydroxyamino)methyl-4-(2-oxo-1,2-dihydropyridin-1-yl)-2H-1-benzopyran, or a pharmaceutically acceptable salt thereof.

9. The compound of claim 5, wherein $R^3$ is chloro, and $R^9$ is —C(O)$R^{12}$, where $R^{12}$ is methyl, namely 6-chloro-2,2-dimethyl-3-(N-hydroxyacetamido)methyl-4-(2-oxo-1,2-dihydropyridin-1-yl)-2H-1-benzopyran, or a pharmaceutically acceptable salt thereof.

10. The compound of claim 5, wherein $R^3$ is bromo, and $R^9$ is hydrogen, namely 6-bromo-2,2-dimethyl-3-(N-hydroxyamino)methyl-4-(2-oxo-1,2-dihydropyridin-1-yl)-2H-1-benzopyran, or a pharmaceutically acceptable salt thereof or a pharmaceutically acceptable salt thereof.

11. The compound of claim 5, wherein $R^3$ is bromo, and $R^9$ is —C(O)$R^{12}$, where $R^{12}$ is methyl, namely 6-bromo-2,2-dimethyl-3-(N-hydroxyacetamido)methyl-4-(2-oxo-1,2-dihydropyridin-1-yl)-2H-1-benzopyran, or a pharmaceutically acceptable salt thereof.

12. The compound of claim 5, wherein $R^3$ is bromo, and $R^9$ is —C(O)$R^{12}$, where $R^{12}$ is ethyl, namely 6-bromo-2,2-dimethyl-3-(N-hydroxypropionamido)-methyl-4-(2-oxo-1,2-dihydropyridin-1-yl)-2H-1-benzopyran, or a pharmaceutically acceptable salt thereof.

13. The compound of claim 5, wherein $R^3$ is bromo, and $R^9$ is —C(O)O$R^{10}$, where $R^{10}$ is methyl, namely 6-bromo-2,2-dimethyl-3-(methoxycarbonylamino)-methyl-4-(2-oxo-1,2-dihydropyridin-1-yl)-2H-1-benzopyran, or a pharmaceutically acceptable salt thereof.

14. The compound of claim 5, wherein $R^3$ is bromo, and $R^9$ is —C(O)NR$^{11}$R$^{12}$, where $R^{11}$ and $R^{12}$ are both hydrogen, namely 6-bromo-2,2-dimethyl-3-(N-hydroxyureido)methyl-4-(2-oxo-1,2-dihydropyridin-1-yl)-2H-1-benzopyran, or a pharmaceutically acceptable salt thereof.

15. The compound of claim 5, wherein $R^3$ is bromo, and $R^9$ is —C(S)NR$^{11}$R$^{12}$, where $R^{11}$ and $R^{12}$ are both hydrogen namely 6-bromo-2,2-dimethyl-3-(N-hydroxythioureido)methyl-4-(2-oxo-1,2-dihydropyridin-1-yl)-2H-1-benzopyran, or a pharmaceutically acceptable salt thereof.

16. A pharmaceutical composition comprising a therapeutically effective amount of a compound of claim 1, or a pharmaceutically acceptable salt thereof, in admixture with one or more pharmaceutically acceptable non-toxic carriers.

* * * * *